US011254922B2

(12) United States Patent
Oja et al.

(10) Patent No.: US 11,254,922 B2
(45) Date of Patent: Feb. 22, 2022

(54) ISOPRENE SYNTHASE AND METHOD OF PREPARING ISOPRENE USING THEREOF

(71) Applicant: SK Innovation Co., Ltd., Seoul (KR)

(72) Inventors: Merja Oja, Espoo (FI); Anne Huuskonen, Helsinki (FI); Marja Ilmén, Helsinki (FI); Jae Hoon Jo, Seoul (KR); Simon MoonGeun Jung, Daejeon (KR); Outi Koivistoinen, Espoo (FI); Sang Min Lee, Seoul (KR); Laura Ruohonen, Helsinki (FI)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 16/354,321

(22) Filed: Mar. 15, 2019

(65) Prior Publication Data

US 2019/0203193 A1 Jul. 4, 2019

Related U.S. Application Data

(62) Division of application No. 15/329,343, filed as application No. PCT/KR2015/007851 on Jul. 28, 2015, now Pat. No. 10,287,565.

(30) Foreign Application Priority Data

Jul. 28, 2014 (KR) ........................ 10-2014-0095972

(51) Int. Cl.

| | |
|---|---|
| ***C12N 9/88*** | (2006.01) |
| ***C12P 5/02*** | (2006.01) |
| ***C12N 15/74*** | (2006.01) |
| ***C12P 5/00*** | (2006.01) |

(52) U.S. Cl.

CPC ............... *C12N 9/88* (2013.01); *C12N 15/74* (2013.01); *C12P 5/007* (2013.01); *C12P 5/026* (2013.01); *C12Y 402/03027* (2013.01)

(58) Field of Classification Search

CPC . C12N 9/88; C12N 15/74; C12P 5/007; C12P 5/026; C12Y 402/03027

See application file for complete search history.

(56) References Cited

U.S. PATENT DOCUMENTS

| | | | |
|---|---|---|---|
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter et al. |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 5,264,618 | A | 11/1993 | Felgner et al. |
| 5,849,970 | A | 12/1998 | Fall et al. |
| 5,990,279 | A | 11/1999 | Carter et al. |
| 8,133,708 | B2 | 3/2012 | Melis |
| 8,609,385 | B2 | 12/2013 | Anderson |
| 9,453,244 | B2 | 9/2016 | Marlière et al. |
| 9,994,869 | B2 | 6/2018 | Song et al. |
| 2009/0226989 | A1 | 9/2009 | Suominen et al. |
| 2011/0045563 | A1 | 2/2011 | Melis |
| 2013/0330709 | A1 | 12/2013 | Beatty et al. |
| 2014/0030785 | A1 | 1/2014 | Kallas et al. |
| 2015/0232884 | A1 | 8/2015 | Duehring |

FOREIGN PATENT DOCUMENTS

| | | | |
|---|---|---|---|
| KR | 1020110020234 | A | 3/2011 |
| WO | 9116024 | A1 | 10/1991 |
| WO | 9117424 | A1 | 11/1991 |
| WO | 9324641 | A2 | 12/1993 |
| WO | 2013166320 | A1 | 11/2013 |
| WO | 2014001517 | A1 | 1/2014 |
| WO | 2014037050 | A1 | 3/2014 |

OTHER PUBLICATIONS

Whisstock et al. Quaterly Reviews of Biophysics, 2003, “Prediction of protein function from protein sequence and structure”, 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36): 11643-50.*

Ahmad et al.; “Antibody-mediated Specific Binding and Cytotoxicity of Liposome-entrapped Doxorubicin to Lung Cancer Cells in Vitro”; Cancer Research; 1992; pp. 4817-4820; vol. 52.

Behr; “Gene Transfer with Synthetic Cationic Amphiphiles: Prospects for Gene Therapy”; Bioconjugate Chem; 1994; pp. 382-389; vol. 5.

Bentley et al.; “Diffusion-Based Process for Carbon Dioxide Uptake and Isoprene Emission in Gaseous/Aqueous Two-Phase Photobioreactors by Photosynthetic Microorganisms”; Biotechnology and Bioengineering; 2012; pp. 100-109; vol. 109:1.

Blaese et al.; “T Lymphocyte-Directed Gene Therapy for ADA SCID: Initial Trial Results After 4 Years”; Science; 1995; pp. 475-480; vol. 270.

(Continued)

*Primary Examiner* — Iqbal H Chowdhury

(74) *Attorney, Agent, or Firm* — The Webb Law Firm

(57) ABSTRACT

Provided are a novel isoprene synthase derived from sweet potato and a method of preparing isoprene using the same, and more specifically, a novel isoprene synthase derived from sweet potato, a gene encoding the isoprene synthase, a host cell transformed with the gene, and a method of preparing isoprene using the same. The isoprene synthase of the present invention may have higher isoprene productivity as compared to isoprene synthases known in the related art to thereby be effectively used in isoprene biosynthesis and preparation of an isoprene polymer using the same.

3 Claims, 21 Drawing Sheets

Specification includes a Sequence Listing.

(56) References Cited

OTHER PUBLICATIONS

Buchschacher, Jr. et al.; "Human Immunodeficieny Virus Vectors for Inducible Expression of Foreign Genes"; Journal of Virology; 1992; pp. 2731-2739; vol. 66:5.
Chica et al. "Semi-rational approaches to engineering enzyme activity: combining the benefits of directed evolution and rational design"; Curr. Opi. Biotechnol; 2005; pp. 378-384; vol. 16.
Crystal; "Transfer of Genes to Humans: Early Lessons and Obstacles to Success"; Science; 1995; pp. 404-410; vol. 270.
Devereux et al.; "A comprehensive set of sequence analysis programs for the VAX"; Nucleic Acids Research; 1984; pp. 387-395; vol. 12:1.
Dranoff et al.; "A Phase I Study of Vaccination with Autologous, Irradiated Melanoma Cells Engineered to Secrete Human Granulocyte-Macrophage Colony Stimulating Factor"; Human Gene Therapy; 1997; pp. 111-123; vol. 7.
Dunbar et al.; "Retrovirally Marked CD34-Enriched Peripheral Blood and Bone Marrow Cells Contribute to Long-Term Engraftment After Autologous Transplantation"; Blood; 1995; pp. 3048-3057; vol. 85:11.
Ellem et al.; "A case report: Immune responses and clinical course of the first human use of granulocyte/macrophage-colony-stimulating-factor-transduced autologous melanoma cells for immunotherapy"; Cancer Immunol Immunother; 1997; pp. 10-20; vol. 44.
Gietz et al.; "[4] Transformation of Yeast by Lithium Acetate/Single-Stranded Carrier DNA/Polyethylene Glycol Method"; Methods in Enzymology; 2002; pp. 87-96; vol. 350.
Gietz et al.; "Improved method for high efficiency transformation of intact yeast cells"; Nucleic Acids Research; 1992; pp. 1425; vol. 20:6.
Gray et al.; "Biochemical Characterization and Homology Modeling of Methylbutenol Synthase and Implications for Understanding Hemiterpene Synthase Evolution in Plants"; The Journal of Biological Chemistry; 2011; pp. 20582-20590; vol. 286:23.
Hakkinen et al.; "Functional characterisation of genes involved in pyridine alkaloid biosynthesis in tobacco"; Phytochemistry; 2007; pp. 2773-2785; vol. 68.
Hermonat et al.; "Use of adeno-associated virus as a mammalian DNA cloning vector: Transduction of neomycin resistance into mammalian tissue culture cells"; Proc. Natl. Acad. Sci. USA; 1984; pp. 6466-6470; vol. 81.
Johann et al.; "GLVR1, a Receptor for Gibbon Ape Leukemia Virus, Is Homologous to a Phosphate Permease of Neurospora crassa and Is Expressed at High Levels in the Brain and Thymus"; Journal of Virology; 1992; pp. 1635-1640; vol. 66:3.
Jouhikainen et al.; "Enhancement of scopolamine production in *Hyoscyamus muticus* L. hairy root cultures by genetic engineering"; Planta; 1999; pp. 545-551; vol. 208.
Julsing et al.; "Functional analysis of genes involved in the biosynthesis of isoprene in Bacillus subtilis"; Appl Microbiol Biotechnol; 2007; pp. 1377-1384; vol. 75.
Kohn et al.; "Engraftment of gene-modified umbilical cord blood cells in neonates with adenosine deaminase deficiency"; Nat Med.; 1995; pp. 1017-1023; vol. 1:10.
Kotin; "Review: Prospects for the Use of Adeno-Associated Virus as a Vector for Human Gene Therapy"; Human Gene Therapy; 1994; pp. 793-801; vol. 5.
Kuzma et al.; "Bacteria Produce the Volatile Hydrocarbon Isoprene"; Current Microbiology; 1995; pp. 97-103; vol. 30.
Malech et al.; "Prolonged production of NADPH oxidase-corrected granulocytes after gene therapy of chronic granulomatous disease"; Proc. Natl. Acad. Sci. USA; 1997; pp. 12133-12138; vol. 94.
Miller et al.; "Construction and Properties of Retrovirus Packaging Cells Based on Gibbon Ape Leukemia Virus"; Journal of Virology; 1991; pp. 2220-2224; vol. 65:5.
Muzyczka; "Adeno-associated Virus (AAV) Vectors: Will They Work?"; J. Clin. Invest.; 1994; pp. 1351; vol. 94.
NCBI; "unnamed protein product [Coffea canephora]"; GenBank accession No. CDP11842.1; Jun. 27, 2014.
Needleman et al.; "A General Method Applicable to the Search for Similarities in the Amino Acid Sequence of Two Proteins"; J. Mol. Biol.; 1970; pp. 443-453; vol. 48.
Pearson et al.; "Improved tools for biological sequence comparison"; Proc. Natl. Acad. Sci. USA; 1988; pp. 2444-2448; vol. 85.
Penttilä et al., "A versatile transformation system for the cellulolytic filamentous fungus Trichoderma reesei", Gene, 1987, pp. 155-164, vol. 61, Elsevier.
Peranen et al.; "T7 Vectors with a Modified T7 lac Promoter for Expression of Proteins in *Escherichia coli*"; Analytical Biochemistry; 1996; pp. 371-373; vol. 236.
Polakowski et al.; "Overexpression of a cytosolic hydroxymethylglutaryl-CoA reductase leads to squalene accumulation in yeast"; Appl Microbiol Biotechnol; 1998; pp. 66-71; vol. 49.
Remy et al.; "Gene Transfer with a Series of Lipophilic DNA-Binding Molecules"; Bioconjugate Chem.; 1994; pp. 647-654; vol. 5.
Samulski et al.; "Helper-Free Stocks of Recombinant Adeno-Associated Viruses: Normal Integration Does Not Require Viral Gene Expression"; Journal of Virology; 1989; pp. 3822-3828; vol. 63:9.
Sharkey et al.; "Isoprene Synthase Genes Form a Monophyletic Clade of Acyclic Terpene Synthases in the TPS-B Terpene Synthase Family"; Evolution; 2012; pp. 1026-1040; vol. 67:4.
Silver et al.; "Characterization of Aspen Isoprene Synthase, an Enzyme Responsible for Leaf Isoprene Emission to the Atmosphere"; The Journal of Biological Chemistry; 1995; pp. 13010-13016; vol. 270:22.
Silver et al.; "Enzymatic Synthesis of Isoprene from Dimethylallyl Diphosphate in Aspen Leaf Extracts"; Plant Physiol.; 1991; pp. 1588-1591; vol. 97.
Smith; "Comparison of Biosequences"; Advances in Applied Mathematics; 1981; pp. 482-489; vol. 2.
Sommerfelt et al.; "Receptor Interference Groups of 20 Retroviruses Plating on Human Cells"; Virology; 1990; pp. 58-69; vol. 176.
Tratschin et al.; "Adeno-Associated Virus Vector for High-Frequency Integration, Expression, and Rescue of Genes in Mammalian Cells"; Molecular and Cellular Biology; 1985; pp. 3251-3260; vol. 5:11.
Tratschin et al.; "A Human Parvovirus, Adeno-Associated Virus, as a Eucaryotic Vector: Transient Expression and Encapsidation of the Procaryotic Gene for Chloramphenicol Acetyltransferase"; Molecular and Cellular Biology; 1984; pp. 2072-2081; vol. 4:10.
Wagner et al.; "Efficient and persistent gene transfer of AAV-CFTR in maxillary sinus"; The Lancet; 1998; pp. 1702-1703; vol. 351.
Wagner et al.; "Three Distinct Phases of Isoprene Formation during Growth and Sporulation of Bacillus subtilis"; Journal of Bacteriology; 1999; pp. 4700-4703; vol. 181:15.
Weissermel et al.; "5.2: Isoprene"; Industrial Organic Chemistry: Fourth, Completely Revised Edition; 2003; pp. 117-122.
West et al.; "Gene Expression in Adeno-Associated Virus Vectors: The Effects of Chimeric mRNA Structure, Helper Virus, and Adenovirus VA RNA"; Virology; 1987; pp. 38-47; vol. 160.
Whisstock et al.; "Prediction of protein function from protein sequence and structure"; Quarterly Reviews of Biophysics; 2003; pp. 307-340; vol. 36; No. 3.
Wilkins; "Volatile Metabolites From Actinomycetes"; Chemosphere; 1996; pp. 1427-1434; vol. 32:7.
Wilson et al.; "Formation of Infectious Hybrid Virions with Gibbon Ape Leukemia Virus and Human T-Cell Leukemia Virus Retroviral Envelope Glycoproteins and the gag and pol Proteins of Moloney Murine Leukemia Virus"; Journal of Virology; 1989; pp. 2374-2378; vol. 63:5.
Winston et al.; "Construction of a Set of Convenient *Saccharomyces cerevisiae* Strains that are Isogenic to S288C"; Yeast; 1995; pp. 53-55; vol. 11.
Witkowski et al.; "Conversion of a beta-ketoacyl synthase to a malonyl decarboxylase by replacement of the active-site cysteine with glutamine"; Biochemistry; 1999; pp, 11643-50; vol. 38; No. 36.
Becker et al., "Quantitative prediction of cellular metabolism with constraint-based models: the COBRA Toolbox", Nature Protocols, 2007, pp. 727-738, vol. 2, No. 3.

(56) References Cited

OTHER PUBLICATIONS

Bentley et al., "Heterologous Expression of the Mevalonic Acid pathway in Cyanobacteria Enhances Endogenous Carbon Partitioning to Isoprene", Molecular Plant, 2014, pp. 71-86, vol. 7, No. 1.
Gründel et al., "Impaired glycogen synthesis causes metabolic overflow reactions and affects stress responses in the cyanobacterium *Synechocystis* sp. PCC 6803", Microbiology, 2012, pp. 3032-3043, vol. 158, Issue 12.
Hess et al., "Coregulation of Terpenoid Pathway Genes and Prediction of Isoprene Production in Bacillus subtilis Using Transcriptomics", PLoS One, 2013, 14 pages, vol. 8, No. 6, Article No. e66104.
Knoop et al., "Flux Balance Analysis of Cyanobacterial Metabolism: The Metabolic Network of *Synechocystis* sp. PCC 6803", PLoS Computational Biology, 2013, 16 pages, vol. 9, No. 6, Article No. e1003081.
Kudoh et al., "Prerequisite for highly efficient isoprenoid production by cyanobacteria discovered through the over-expression of 1-deoxy-d-xylulose 5-phosphate synthase and carbon allocation analysis", Journal of Bioscience and Bioengineering, 2014, pp. 20-28, vol. 118, No. 1.
Lindberg et al., "Engineering a platform for photosynthetic isoprene production in cyanobacteria, using Synechocystis as the model organism", Metabolic Engineering, 2010, pp. 70-79, vol. 12, No. 1.
Mahadevan et al., "The effects of alternate optimal solutions in constraint-based genome-scale metabolic models", Metabolic Engineering, 2003, pp. 264-276, vol. 5, No. 4.
Shastri et al., "Flux Balance Analysis of Photoautotrophic Metabolism", Biotechnology Progress, 2005, pp. 1617-1626, vol. 21, No. 6.
Young et al., "Mapping photoautotrophic metabolism with isotopically nonstationary (13)C flux analysis", Metabolic Engineering, 2011, pp. 656-665, vol. 13, No. 6.
Hong et al., "Isoprene hydrocarbons production upon heterologous transformation of Saccharomyces cerevisiae", Journal of Applied Microbiology, 2012, pp. 52-65, vol. 113.

* cited by examiner

1. Tricyclene_Medicago_truncatula_sp|Q5UB07|TPS4_MEO
2. Medicago_sativa_gi|585498871|gb|GAFF01118088.1|_0
3. Tricyclene_Lotus_japonicus_sp|Q672F7|TPS2_LOTJA_0
4. S13_Qpetraea_IpsS
5. Fragaria_vesca_gi|470140811|ref|XP_004306033.1|_0_N
6. Morus_notabilis_gi|587936327|gb|EXC23171.1|_0_NA_s
7. Elaeocarpus
8. Elaeocarpus_photiniifolius_gi|388282537|dbj|FX134022
9. Populus_trichocarpa_tr|B9HE95|B9HE95_POPTR_0__sc
10. Ocimene_Vitis_vinifera_tr|A5BLS5|A5BLS5_VITVI_0__sc
11. sp|Q50L36|ISPS_POPAL 1
12. CAC35696/3N0G/Q9AR86
13. Sha_Salix_IspS_AEK70970.1
14. Sha_Maltemifolia_IspS_AAP40638.1
15. Sha_Eglobulus_IspS_BAF02831.1
16. Eucalyptus_grandis_gi|629080625|gb|KCW47070.1|_0_
17. Sha_Wistera_IspS_AEK70969.1
18. Sha_Rpseudoacacia_IspS_AEK70968.1|
19. S3_Ahypogaea_IpsS
20. S7_Gmax_IpsS
21. sp|Q6EJ97|ISPS_PUEML 1
22. S9_Mpruriens_IpsS
23. S5_Gmax_IpsS
24. S11_Ccajans_IpsS
25. Mangifera_indica_gi|617864104|gb|GBCV01019870.1|_
26. I.batatas

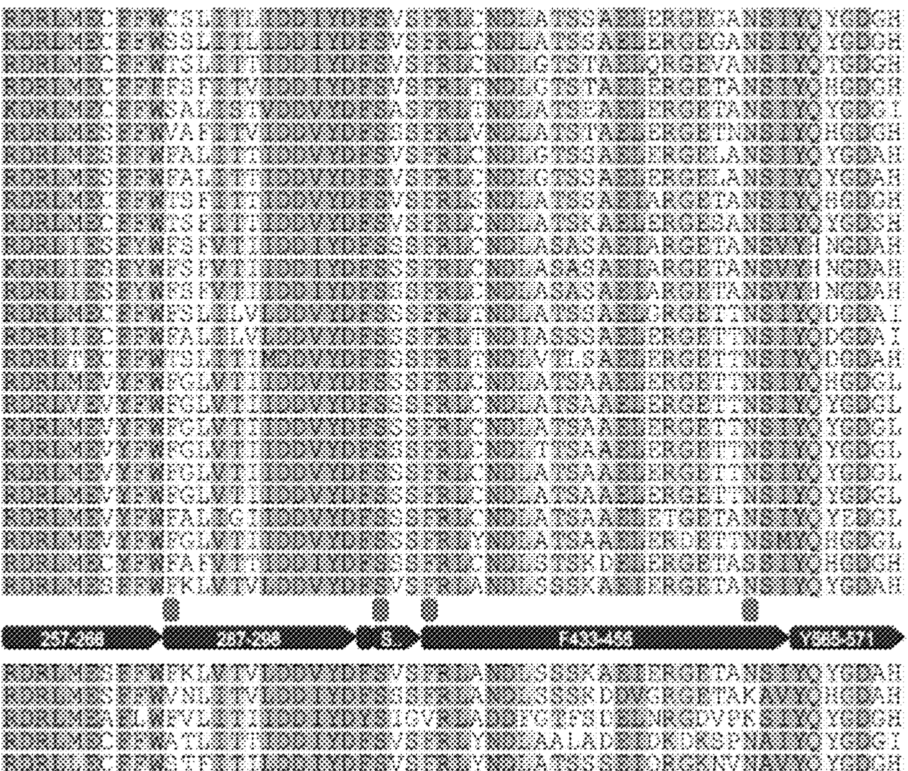

27. Ipomoea_batatas_gi|345720078|gb|JP105673.1|_0_NA
28. Sesamum_indicum_gi|357338539|gb|JP645798.1|_0_
29. Sha_Hlupulus_Mts2_ACI32638.1
30. Ocimene_Matricaria_recutita_sp|6RE61|TPS4_MATRE_
31. Dahlia_pinnata_gi|629159945|gb|GBDN01008783.1|_1_

Fig. 3

ISOPRENE SYNTHASE AND METHOD OF PREPARING ISOPRENE USING THEREOF

CROSS-REFERENCE TO RELATED APPLICATIONS

This application is a divisional application of U.S. patent application Ser. No. 15/329,343, filed Jan. 26, 2017, which was the United States national phase of International Application No. PCT/KR2015/007851 filed Jul. 28, 2015, which claims priority to Korean Patent Application No. 10-2014-0095972 filed Jul. 28, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1700617_ST25.txt. The size of the text file is 167,544 bytes, and the text file was created on Jan. 26, 2017.

TECHNICAL FIELD

The present invention relates to a novel isoprene synthase and a method of preparing isoprene using the same, and more specifically, to a polynucleotide encoding the novel isoprene synthase, a recombinant host cell having the polynucleotide introduced, and a method of preparing isoprene using the same.

BACKGROUND ART

Isoprenoids are isoprene polymers that find use in pharmaceuticals, neutraceuticals, flavors, fragrances, and rubber products. Supplies of natural isoprenoid, however, are restricted due to ecological concerns. For this reason, and in order to provide isoprenoid compositions having less impurities and greater uniformity, isoprenoids such as rubber are often produced synthetically. Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, $4^{th}$ ed., Wiley-VCH, pp. 117-122, 2003). The C5 skeleton can also be synthesized from smaller subunits.

It would be desirable, however, to have a commercially viable method of producing isoprene that was independent of nonrenewable resources. Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent and increase with the association to leaf development.

An isoprene-producing enzyme, isoprene synthase, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, Chemosphere, 32:1427-1434, 1996), and it varies in amount according to the phase of bacterial growth and the nutrient content of the culture medium (U.S. Pat. No. 5,849,970 to Fall et al.; and Wagner et al., J Bacteriol, 181:4700-4703, 1999).

The levels of isoprene obtainable through bacterial systems of the prior art, however, are insufficient for commercial uses. Thus, what the art needs is an effective and large scaled bacterial or microbial isoprene production process to provide feedstock for the manufacture of isoprene.

Accordingly, as a result of an effort for developing a method of preparing isoprene using a novel isoprene synthase gene having excellent isoprene productivity, the present inventors performed mining on a novel isoprene synthase gene, and confirmed that a recombinant microorganism transformed with the isoprene synthase gene has more excellent isoprene productivity than that of a host cell transformed with the isoprene synthase gene known in the art, thereby completing the present invention.

SUMMARY OF THE INVENTION

Technical Problem

An object of the present invention is to provide an isoprene synthase having excellent isoprene productivity and a gene encoding the isoprene synthase.

Another object of the present invention is to provide a recombinant host cell expressing an isoprene synthase and a method of preparing isoprene by culturing the recombinant host cell.

Solution to Problem

In order to achieve the foregoing objects, the present invention provides an isoprene synthase comprising an amino acid sequence of SEQ ID NO: 1; or an amino acid sequence having 70% or more sequence homology to the amino acid sequence of SEQ ID NO: 1.

In addition, the present invention provides a polynucleotide encoding the isoprene synthase as described above and a recombinant vector into which the polynucleotide is operably introduced.

Further, the present invention provides a recombinant host cell into which the polynucleotide or the recombinant vector as described above is introduced.

In addition, the present invention provides a polynucleotide comprising a nucleotide sequence of SEQ ID NO: 3 optimized by codon optimization of the polynucleotide sequence encoding the isoprene synthase for blue-green algae (cyanobacteria); and a recombinant vector into which the polynucleotide is operably introduced.

In addition, the present invention provides a polynucleotide comprising a nucleotide sequence of SEQ ID NO: 33 optimized by codon optimization of the polynucleotide sequence encoding the isoprene synthase for yeast; and a recombinant vector into which the polynucleotide is operably introduced.

Further, the present invention provides recombinant blue-green alga (cyanobacteria) or recombinant filamentous fungi; into which the polynucleotide comprising the nucleic acid sequence of SEQ ID NO: 3 as described above or the recombinant vector comprising the polynucleotide as described above is introduced.

Further, the present invention provides recombinant yeast; into which the polynucleotide comprising the nucleic acid sequence of SEQ ID NO: 33 as described above or the recombinant vector comprising the polynucleotide as described above is introduced.

In addition, the present invention provides a method of preparing isoprene including: (a) culturing the recombinant host cell as described above to prepare isoprene; and (b) obtaining the prepared isoprene.

Further, the present invention provides a method of preparing isoprene including: (a) culturing the recombinant blue-green algae (cyanobacteria), filamentous fungi or yeast as described above to prepare isoprene; and (b) obtaining the prepared isoprene.

BRIEF DESCRIPTION OF THE DRAWINGS

FIG. 3 shows a multiple sequence alignment (MSA) result to around the substrate-binding amino acid sequence (SEQ ID NOS: 67-96).

DESCRIPTION OF THE INVENTION

Unless defined otherwise, all the technical and scientific terms used herein have the same meanings as those generally understood by persons skilled in the art to which the present invention pertains. Generally, the nomenclature used herein are well known and commonly employed in the art.

In a first aspect of the present invention, the present invention provides an isoprene synthase comprising an amino acid sequence of SEQ ID NO: 1 or an amino acid sequence having at least 70%, preferably at least 75%, more preferably at least 80%, still more preferably at least 85%, still more preferably at least 90%, still more preferably at least 95%, more and more preferably at least 98%, most preferably at least 99% sequence homology to the amino acid sequence of SEQ ID NO: 1.

The isoprene synthase belongs to a terpene synthase (TPS)-B family, and has an amino acid sequence specifically conserved in isoprene synthase, referred to as an "isoprene score" (Sharkey et al., Evolution, 67:1026, 2013). Important amino acids in the isoprene synthase are F338, 5445, F485 and N505 based on amino acid sequences of the *Populus alba*- and *Populus canescens*-derived isoprene synthases, and phenylalanine of F338 and F485 are important amino acids to decrease the size of a substrate-binding site so that large substrates such as geranyl diphosphate, farnesyl diphosphate, geranylgeranyl diphosphate, and the like, are not allowed to enter into an active site of an enzyme.

Therefore, the isoprene synthase of the present invention is characterized by comprising an amino acid sequence having 90% or more sequence homology to sequences at positions corresponding to RDRLMESFFW at position Nos. 257-266, FKLVTVLDDVYD at position Nos. 287-298, F369, SVS at position Nos. 394-396, FRLANDLSSS-KAEIERGETANSI at position Nos. 433-455, and YQYG-DAH at position Nos. 515-521 in an amino acid sequence of SEQ ID NO: 1. In addition, the isoprene synthase of the present invention is characterized by having at positions corresponding to the positions in SEQ ID NO: 1 at least one, preferably at least two, more preferably at least three, still more preferably at least four of the amino acids W266, F287, F369, F433, N453 and Y515.

The isoprene synthase of SEQ ID NO: 1 of the present invention comprises an amino acid sequence derived from sweet potato (*Ipomoea batatas*).

Figure 1A:
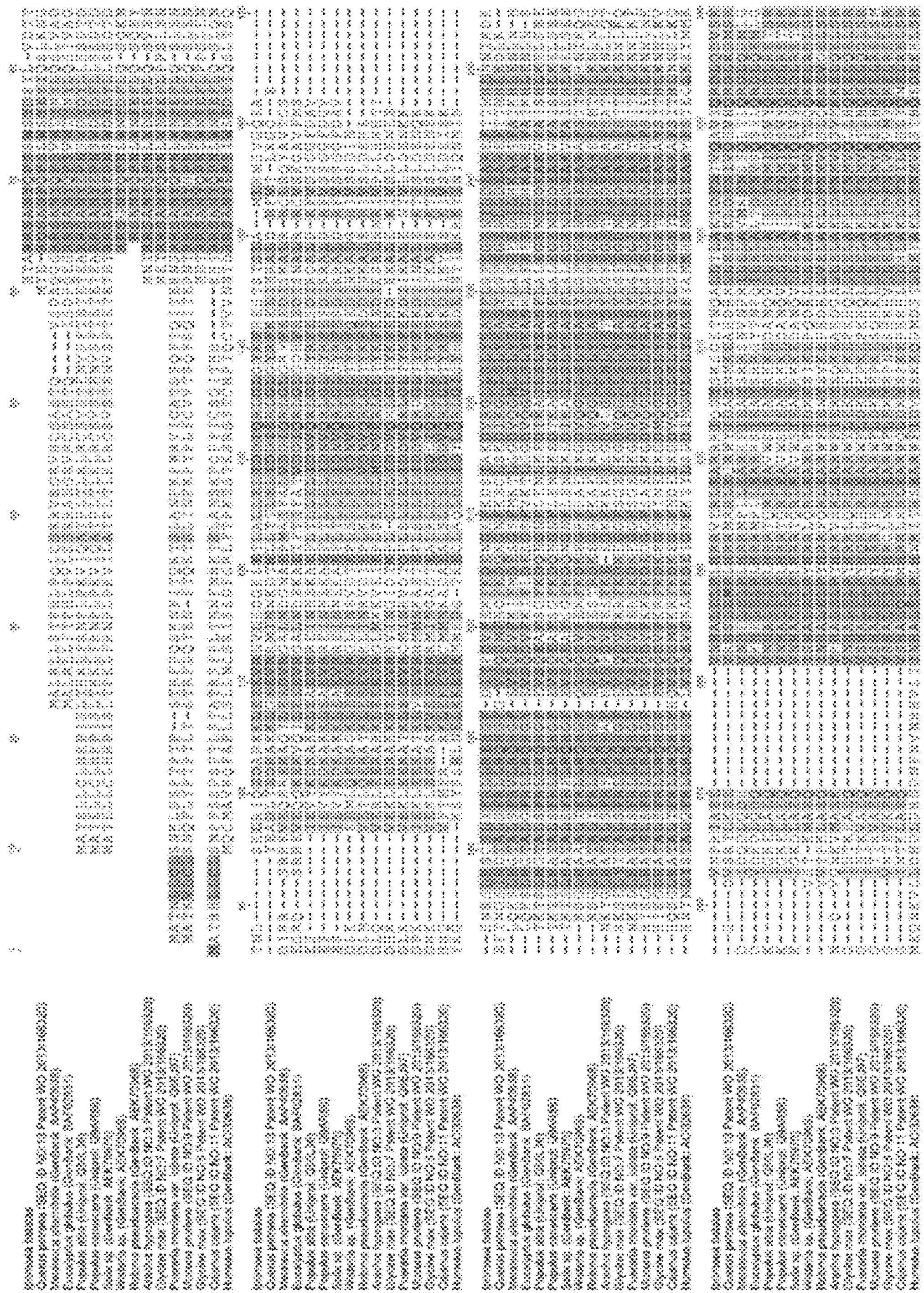
FIG. 1*a* and FIG. 1*b* show an amino acid sequence alignment result of *I. batatas*—derived isoprene synthase with known isoprene synthases (SEQ ID NOS: 37-51).
Figure 1B:
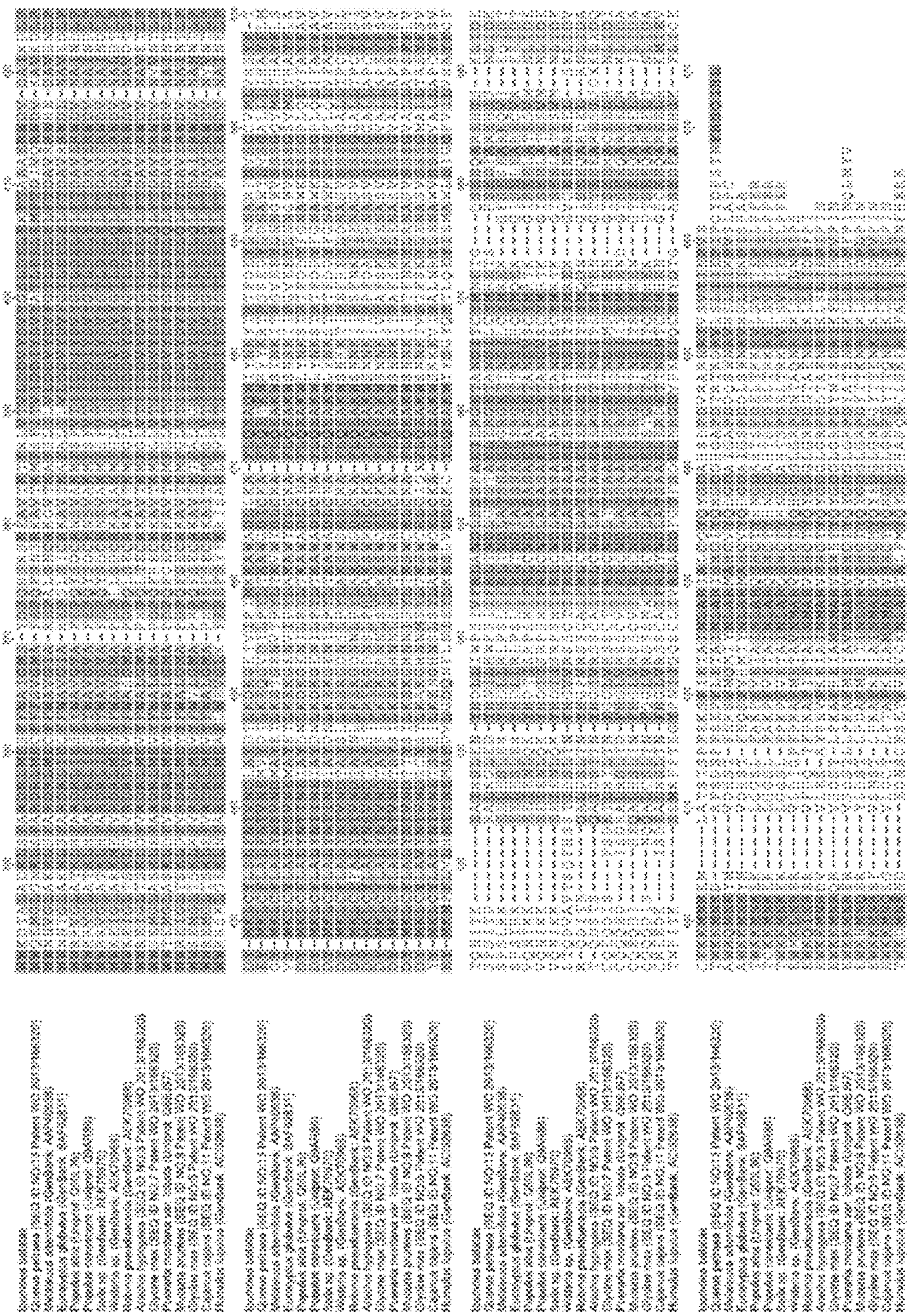
Figure 2:
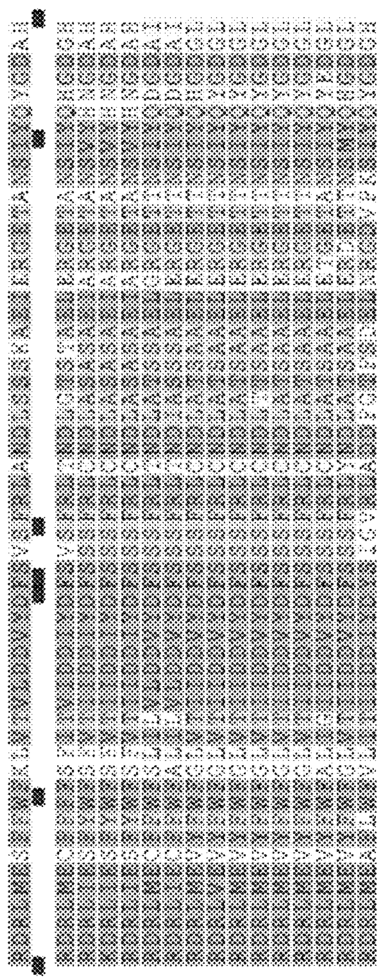
FIG. 2 is directed to multiple sequence alignment (MSA) result showing the sequence around the substrate binding amino acids in isoprene synthase (SEQ ID NOS: 52-66).

An amino acid sequence alignment result of *I. batatas*-derived isoprene synthase is shown in FIG. 1*a* and FIG. 1*b*, and an amino acid sequence alignment result of isoprene synthase candidates including *P. alba*-, *A. hypogaea*-derived isoprene synthases which are two known isoprene synthases, as a reference is shown in FIG. 2.

As a result of searching patent sequence database based on *I. batatas*-derived isoprene synthase having an amino acid sequence of SEQ ID NO: 1 according to the present invention, it was confirmed that the isoprene synthase derived from sweet potato of the present invention has 56% sequence homology to *Quercus petraea*-derived isoprene synthase (U.S. Patent Application Publication No. 2013/0330709) and has low sequence homology to the isoprene synthase known in the related art.

In a second aspect of the present invention, the present invention provides a polynucleotide encoding the isoprene synthase.

In the present invention, the polynucleotide may be codon-optimized for microorganisms selected from the group consisting of *E. coli, bacillus genus* strain, blue-green algae (cyanobacteria), yeast and filamentous fungi. Also the introns may be removed from the original gene. In the present invention the term "polynucleotide" is used to mean the gene in its original or modified form or the coding sequence in its original or modified form.

The codon optimization in the present invention means that a codon having an average codon frequency less than 12% on the microorganism is substituted with a codon having an average codon frequency more than 12% on the microorganism.

In an exemplary embodiment of the present invention, with a target of a isoprene synthase polynucleotide of SEQ ID NO: 2, the codon optimization was performed to enable expression in either *Synechocystis* sp. (strain PCC6803), which is blue-green algae cyanobacteria, or *E. coli* (SEQ ID NO: 3). This same codon optimized nucleotide sequence for bacteria can be used also for filamentous fungi. In an exemplary embodiment of the present invention SEQ ID NO:3 was used for the filamentous fungus *Trichoderma.*

In another exemplary embodiment of the present invention, with a target of an isoprene synthase polynucleotide of SEQ ID NO: 2, the codon usage was optimized for *S. cerevisiae* (SEQ ID NO:33) to enable expression either in *S. cerevisiae* or *Pichia* (*P. kudriavzevii*).

Therefore, in a preferred embodiment of the present disclosure, the polynucleotide encoding the isoprene synthase might comprise any one nucleotide sequence of SEQ ID NOs: 2, 3 or 33, but the present invention is not limited thereto.

In a third aspect of the present invention, the present invention provides a polynucleotide encoding an isoprene synthase comprising a nucleotide sequence of SEQ ID NO: 3 by codon optimization of the polynucleotide encoding the isoprene synthase for blue-green algae (cyanobacteria), and *E. coli*, useful also for other bacteria and filamentous fungi, in particular *Trichoderma* and *Aspergillus.*

In a fourth aspect of the present invention, the present invention provides a polynucleotide encoding an isoprene synthase comprising a nucleotide sequence of SEQ ID NO: 33 by codon optimization of the polynucleotide encoding the isoprene synthase for *Saccharomyces cerevisiae*, useful also for *Saccharomyces, Pichia* and other yeasts.

In a fifth aspect of the present invention, the present invention provides a recombinant vector into which the polynucleotide is operably introduced; and a recombinant host cell into which the polynucleotide or the recombinant vector is introduced.

The recombinant vector in the present invention may contain a promoter for expressing the polynucleotide.

Examples of the promoter contained in the recombinant vector could include psbA2, trc, rbcL, petJ, psaA, psaB, tac, cpcB, petC or lac promoters for expression in blue-green algae (cyanobacteria), PGK1, TPI1, TDH, PDC1, FBA1, ENO1, ENO2, PYK1, ADH1, or TEF1 promoters for expression in yeast, preferably the promoter is selected from the group consisting of PGK1, TPI1 and TEF1 for expressing in yeast., cbh1, gpdA, glaA, pdc or exlA promoters for expression in filamentous fungi, and a CMV35S promoter for expression in a plant cell, but the present invention is not limited thereto.

In a preferred embodiment of the present invention, a polynucleotide sequence is contained in plasmids. In another preferred embodiment of the present invention, a polynucleotide sequence is incorporated into the genome of a host cell. In some preferred embodiments of the present invention, a host is selected from the group consisting of gram-positive bacterial cells, gram-negative bacterial cells, filamentous fungal cells, and yeast cells, but the present invention is not limited thereto.

In some preferred embodiments of the present invention, *escherichia* species (*E. coli*), *pantoea* species (*Pantoea citrea*), *bacillus* species (*Bacillus subtilis*), *yarrowia* species (*Yarrowia lipolytica*), and *trichoderma* species (*Trichoderma reesei*), but the present invention is not limited thereto. In some preferred embodiments, the host cell is cultured in a medium containing carbon sources selected from the group consisting of $CO_2$, bicarbonate, glucose, glycerol, glycerine, dihydroxyacetone, yeast extract, biomass, molasses, sucrose, galactose, sorbose, sorbitol, xylose, arabinose, cellulose, xylan, lactose and oil, but not limited thereto.

Preferably, the host cell of the present invention may be blue-green algae (cyanobacteria), yeast, filamentous fungi, or plant cells.

In a preferred embodiment of the present invention, the filamentous fungi may be *Trichoderma* genus, *Mucor* genus, *Mortierella* genus, *Neurospora* genus or *Aspergillus* genus, advantageously the filamentous fungi is *Trichoderma* or *Aspergillus* genus and the plant cell may be *Nicotiana* genus, *Catharantus* genus or *Hyroscyamus* genus plant cells.

In a sixth aspect of the present invention, the present invention provides a polynucleotide comprising a nucleotide sequence of SEQ ID NO: 3 by codon optimization of the polynucleotide encoding the isoprene synthase on blue-green algae (cyanobacteria), useful also for other bacteria and filamentous fungi, and a recombinant vector into which the polynucleotide is operably introduced; and a recombinant blue-green algae (cyanobacteria), bacteria or filamentous fungi into which the polynucleotide or the recombinant vector is introduced.

In a seventh aspect of the present invention, the present invention provides a polynucleotide comprising a nucleotide sequence of SEQ ID NO:33 by codon optimization of the polynucleotide encoding the isoprene synthase on *Saccharomyces cerevisiae* useful for *Saccharomyces, Pichia* and other yeasts, and a recombinant vector into which the polynucleotide is operably introduced; and a recombinant yeast into which the polynucleotide or the recombinant vector is introduced.

In the present invention, the recombinant vector may comprise psbA2, trc, rbcL, petJ, psaA, psaB, tac, cpcB, petC or lac promoter for expression in blue-green algae (cyanobacteria).

Preferably, the blue-green algae may be unicellular blue-green algae or multicellular blue-green algae. The unicellular blue-green algae may be *Synechocystis* genus or *Synechococcus* genus strain, and the multicellular blue-green algae may be *Gloeocapsa* genus or filamentous cyanobacteria.

In a preferred embodiment of the present invention, the filamentous cyanobacteria may be *Nostoc* genus, *Anabaena* genus or *Arthospira* genus, and the yeast may be *Saccharomyces* genus, *Pichia* genus, *Candida* genus, *Kazachstania* genus, *Kluyveromyces* genus, *Hansenula* genus, *Rhodosporidium* genus, *Cryptococcus* genus or *Yarrowia* genus.

The polynucleotide is operably linked when being disposed with other nucleic acid sequences in a functional relationship. This may be polynucleotide and a regulatory sequence(s) linked in the manner of enabling polynucleotide expression when appropriate molecules (for example, transcriptional activation protein) are bound to the regulatory sequence(s). For example, nucleotide sequence for a pre-sequence or a secretion leader is operably linked to nucleotide sequence for a polypeptide when being expressed as a pre-protein participating in secretion of polypeptide; a promoter or an enhancer is operably linked to a coding sequence when having an influence on transcription of sequence; or a ribosome binding site is operably linked to a coding sequence when having an influence on transcription of sequence; or a ribosome binding site is operably linked to a coding sequence when being disposed so that translation is easily performed. In general, term: 'operably linked' means that the linked nucleotide sequences are contacted with each other, or in the case of the secretion leader, contacted with the nucleotide sequence and present within a leading frame. However, the enhancer does not need to have a contact. The link of the sequences is performed by ligation (linkage) in a convenient restriction enzyme site. When the site does not exist, a synthetic oligonucleotide adaptor or a linker according to general method is used.

A method of inserting the polynucleotide into the genome of a host cell may be a generally known genetic engineering method, and a non-viral transfer method may include electroporation, lipofection, microinjection, biolistic, virosome, liposome, immuno-liposome, multivalent cation or lipid: nucleic acid conjugate, naked DNA, artificial virion and chemical-enhanced uptake of DNA. Sonoporation, for example, a method using a sonitron 2000 system (Rich-Mar) may be used for transfer of nucleic acids, and other representative nucleic acid transfer systems include Amaxa Biosystems (Cologne, Germany), Maxcyte, Inc. (Rockville, Md.) and BTX Molesular Syetem (Holliston, Mass.). The lipofection method is disclosed in U.S. Pat. Nos. 5,049,386, 4,946,787, and 4,897,355, and lipofection reagent is commercially available, for example, Transfectam™ and Lipofectin™. Cationic and neutral lipids that are suitable for efficient receptor-recognition lipofection of polynucleotides include those of Feigner (WO 91/17424 and WO 91/16024), and may be transferred to cells via ex-vivo administration or to target tissues via in-vivo administration. A method of preparing lipid:nucleic acid complex, containing targeted liposomes such as immunolipid complexes, is well known in the art (Crystal, *Science.,* 270:404-410, 1995; Blaese et al., *Cancer Gene Ther.,* 2:291-297, 1995; Behr et al., *Bioconjugate Chem.,* 5:382389, 1994; Remy et al., *Bioconjugate Chem.,* 5:647-654, 1994; Gao et al., *Gene Therapy.,* 2:710-722, 1995; Ahmad et al., *Cancer Res.,* 52:4817-4820, 1992; U.S. Pat. Nos. 4,186,183; 4,217,344; 4,235,871; 4,261,975; 4,485,054; 4,501,728; 4,774,085; 4,837,028; 4,946,787).

The tropism of a retrovirus may be altered by unification with foreign envelope proteins and thereby expand kinds of target cells. A lentiviral vector is a type of retroviral vector that is able to transduce or infect non-dividing cells and produce high viral titers. A retroviral gene transfer system is determined depends on the target tissue. The retroviral vector includes cis-acting long terminal repeats with packaging capacity for 6-10 kb of foreign sequence. The minimum cis-acting LTRs which are sufficient for replication and packaging of the vectors may be used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (Buchscher et al., *J. Virol.,* 66:2731-2739, 1992; Johann et al., J. *Virol.,* 66:1635-1640, 1992; Sommerfelt et al., *Virol.,* 176:58-59, 1990; Wilson et al., *J. Virol.,* 63:2374-2378, 1989; Miller et al., *J. Virol.,* 65:2220-2224, 1991).

In a case of temporarily expressing a sucrose phosphorylase protein, an adenoviral based system may be frequently used. Adenoviral based vectors are capable of very high transduction efficiency in many cell types and do not require cell division. When using the vectors, high titer and high levels of expression may be obtained and a mass-production is possible with a relatively simple system. In addition, Adeno-associated virus ("AAV") vectors are also used to transduce cells with target nucleic acids, for example, for in vitro production of nucleic acids and peptides, and for in vivo and ex vivo gene therapy (West et al., *Virology.,* 160:38-47, 1987; U.S. Pat. No. 4,797,368; WO 93/24641; Kotin, *Human Gene Therapy.,* 5:793-801, 1994; Muzyczka, *J. Clin. Invest.,* 94:1351, 1994), and a construction of recombinant AAV vectors were already known (U.S. Pat. No. 5,173,414; Tratschin et al., *Mol. Cell. Biol.,* 5:3251-3260, 1985; Tratschin, et al., *Mol. Cell. Biol.,* 4:20722081, 1984; Hermonat & Muzyczka, *PNAS.,* 81:6466-6470, 1984; Samulski et al., *J Virol.,* 63:3822-3828, 1989). In clinical trials, at least six viral vector approaches are currently available for gene transfer, which utilize approaches that involve complementation of defective vectors by genes inserted into helper cell lines to generate the transducing agent. pLASN and MFG-S are examples of retroviral vectors that have been used in clinical trials (Dunbar et al., *Blood.,* 85:3048, 1995; Kohn et al., *Nat. Med.,* 1:1017, 1995; Malech et al., *PNAS.,* 94:12133, 1997), and PA317/pLASN is the first therapeutic vector used in a gene therapy trial (Blaese et al., *Science.,* 270:475-480, 1995), and transduction efficiencies of 50% or greater have been observed for MFG-S packaged vectors (Ellem et al., *Immunol Immunother.,* 44(1):10-20, 1997; Dranoff et al., *Hum. Gene Ther.,* 1:111-2, 1997).

Recombinant adeno-associated virus vectors (rAAV) are a promising alternative gene delivery systems based on the defective and nonpathogenic parvovirus adeno-associated type 2 virus. All vectors are derived from a plasmid that retains the AAV 145 bp inverted terminal repeats flanking the transgene expression cassette. Efficient gene transfer and stable transgene delivery due to integration into the genomes of the transduced cell are key features for this vector system (Wagner et al., *Lancet.,* 351:9117, 1998; Kearns et al., *Gene Ther.,* 9:748-55, 1996).

In an eighth aspect of the present invention, the present invention provides a method of preparing isoprene including: (a) culturing the recombinant host cell as described above to prepare isoprene; and (b) obtaining the prepared isoprene.

The culturing of the step (a) may be performed in a medium containing carbon sources selected from the group consisting of $CO_2$, bicarbonate, glucose, glycerol, glycerine, dihydroxyacetone, yeast extract, biomass, molasses, sucrose, galactose, sorbose, sorbitol, xylose, arabinose, cellulose, xylan, lactose and oil.

In a ninth aspect of the present invention, the present invention provides a method of preparing isoprene including: (a) culturing the recombinant blue-green algae (cyanobacteria), bacteria, recombinant filamentous fungi or yeast as described above to prepare isoprene; and (b) obtaining the prepared isoprene.

The methods may additionally include (c) polymerizing isoprene.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987).

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, N.Y. (1991) provides those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

In combination with isoprene synthase expression of other genes contributing to isoprene production can be introduced into blue green algae (cyanobacteria), bacteria, filamentous fungi or yeast, cells. For example, the idi gene coding for isopentenyl-diphosphate delta-isomerase (EC 5.3.3.2) can be introduced to enhance conversion of isopentenyl diphosphate (IPP) to dimethylallyl diphosphate (DMAPP) that is the substrate of isoprene synthase. Also one or more genes coding for the mevalonate pathway components, mevalonate kinase (EC2.7.1.36), phosphomevalonate kinase (EC2.7.4.2), pyrophoshomevalonate decarboxylase (EC 4.1.1.33), acetoacetyl-CoA thiolase (EC2.3.1.9), HMG-CoA synthase (EC2.3.3.10) or HMG-CoA reductase (EC1.1.1.34) can be cloned under a suitable cyanobacteria, bacteria, filamentous fungi or yeast promoter that allow expression in these hosts. Two or more genes are expressed as a transcriptional fusion under the control or under the transcriptional control of a cyanobacteria or bacteria promoter. When two or more genes are expressed in, filamentous fungi or yeast, each gene is expressed under the control of an individual filamentous fungal or yeast promoter. Advantageous for expression of isoprene synthase is for example a combination of IDI and HMG reductase in filamentous fungi and in yeast, in particular in *Pichia* and *Saccharomyces*.

As used herein, the term 2-methyl-1,3-butadiene (CAS #78-79-5) ("isoprene") refers to the direct and final volatile C5 hydrocarbon product from the elimination of pyrophosphate from 3,3-dimethylallyl pyrophosphate (DMAPP), and does not involve the linking or polymerization of [an] IPP molecule(s) to [a] DMAPP molecule(s).

As used herein, the terms "isoprene synthase," and "IspS," refer to the enzymes that catalyze the elimination or pyrophosphate from diemethylallyl diphosphate (DMAPP) to form isoprene.

In some embodiments, the term "IspS" refers to a naturally occurring mature enzyme or portion thereof.

The present invention comprises proteins comprising an amino acid sequence having 70% or more identity with the amino acid sequence of Isoprene synthase from sweet potato, the proteins comprise "variant proteins".

In some preferred embodiments, variant proteins differ from a parent protein (e.g., set forth as SEQ ID NO:1) by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

In present invention, the proteins comprising an amino acid sequence having 70% identity with amino acid sequence set forth as SEQ ID NO:1 of Isoprene synthase can be generated with several methods including but not limited to site-saturation mutagenesis, scanning mutagenesis, insertional mutagenesis, random mutagenesis, site-directed mutagenesis, and directed-evolution, as well as various other recombinatorial approaches.

As used herein the term "gene" refers to a polynucleotide (e.g., a DNA segment) that encodes a polypeptide and includes regions preceding and following the coding regions as well as intervening sequences (introns) between individual coding segments (exons). Polynucleotides introduced into host cells may comprise the coding region without introns and with or without the preceding or following regions of the original gene. Furthermore the codons may be modified to be more suitable for the host cell.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" is one wherein the function of the polynucleotide is essentially the same as the polynucleotide based on sweet potato isoprene synthase (IspS). Additionally, analogous polynucleotides include at least 45%, 50%, 55%, 60%, 65%, 70%, 75%, 80%, 85%, 90%, 95%, 97%, 98%, 99% or 100% sequence identity with the amino acid sequence of the batate isoprene synthase. In additional embodiments more than one of the above properties applies to the sequence. Analogous sequences are determined by known methods of sequence alignment. A commonly used alignment method is BLAST, although as indicated above and below, there are other methods that also find use in aligning sequences.

Thus, "percent (%) nucleic acid sequence identity" is defined as the percentage of nucleotide residues in a candidate sequence that is identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, "recombinant" includes reference to a cell or vector, that has been modified by the introduction of a heterologous nucleic acid sequence or that the cell is derived from a cell so modified. Thus, for example, recombinant cells expresses genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

As used herein, the terms "amplification" and "gene amplification" refer to a process by which specific polynucleotides are disproportionately replicated such that the amplified polynucleotide becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the terms "amplifiable marker," "amplifiable gene," and "amplification vector" refer to a polynucleotide or a vector comprising a polynucleotide, which permits the amplification of that polynucleotide under appropriate growth conditions.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, the term "heterologous protein" refers to a protein or polypeptide that does not naturally occur in the host cell. Examples of heterologous proteins include enzymes such as isoprene synthases. In some embodiments, the polynucleotides encoding the proteins are naturally occurring genes, while in other embodiments mutated and/or synthetic polynucleotides are used.

As used herein, "homologous protein" refers to a protein or polypeptide native or naturally occurring in a cell. In preferred embodiments, the cell is a Gram-negative cell, while in particularly preferred embodiments the cell is an *Escherichia* host cell.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

The term "mature" form of a protein or peptide refers to the final functional form of the protein or peptide. To exemplify, a mature form of sweet potato isoprene synthase includes the amino acid sequence of SEQ ID NO: 1.

The term "precursor" form of a protein or peptide refers to a mature form of the protein having a prosequence operably linked to the amino or carbonyl terminus of the protein. The precursor may also have a "signal sequence" operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score. "Percent sequence identity," "percent amino acid sequence identity," "percent gene sequence identity," and/or "percent nucleic acid/polynucleotide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "corresponding to," refers to a residue at the enumerated position in a protein or peptide, or a residue that is analogous, homologous, or equivalent to an enumerated residue in a protein or peptide. As used herein, "corresponding region," generally refers to an analogous position along related proteins or a parent protein.

As used herein, the terms "multiple sequence alignment" and "MSA" refer to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence obtained from a MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "headspace" refers to the vapor/air mixture trapped above a solid or liquid sample in a sealed vessel.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise.

EXAMPLES

Hereinafter, the present invention will be described in detail with reference to the following Examples. However, the following examples are only for exemplifying the present invention and it will be obvious to those skilled in the art that the scope of the present invention is not construed to be limited to these examples.

Example 1: Genome Mining for Novel Isoprene Synthase Genetic Search

The isoprene synthase belongs to a terpene synthase (TPS)-B family, and has an amino acid specifically conserved in isoprene synthase, referred to as an "isoprene score" (Sharkey et al., Evolution, 67: 1026, 2013). Important amino acids in the isoprene synthase are F338, 5445, F485 and N505 based on amino acid numbering of sequences of the *Populus alba*- and *Populus canescens*-derived isoprene synthases, and phenylalanines of F338 and F485 respectively are amino acids which have an important role to decrease a size of a substrate-binding site so that large substrates such as geranyl diphosphate, farnesyl diphosphate, geranylgeranyl diphosphate, and the like, are not allowed to enter into an active site of an enzyme.

Bi-functional myrcene synthase of *Humulus lupulus* having low activity as compared to other isoprene synthases lacks F485. N505 has a critical role to determine an ion requirement of terpene synthases, and terpene synthase without an ion requirement has cationic lysine, serine, or asparagine positioned at position No. 505. S445 is present at a first position of triple serine motif, and other TPS-b protein usually has valine (Val) and isoleucine (Ile) in the middle of the triple serine motif; however, S445 present at the first position of the triple serine motif is conserved in almost all Tps-b family and thus, it is judged that S446 positioned in the middle of the triple serine motif is not important in preparation of isoprene.

In addition, W317 and Y565, which are amino acids present in almost all TPS family sequences, are essential to define a size of a substrate-bound pocket.

In addition, N489 is conserved in isoprene/ocimene clade of the Tps-B

In order to determine isoprene Synthase candidates, a homology-based database search was conducted. Isoprene synthase sequences using Query sequence are as follows:

1) *Populus alba* (white poplar, Uniport: Q50L36), *Populus canescens* (grey poplar, Uniprot: Q9AR86, PDB: 3N0G) and *Pueraria montana* var. *lobata* (kudzu wine, Uniprot: Q6EJ97);
2) *Arachis hypogaea* (peanut, SEQ ID No: 3), Glycine max (soybean, SEQ ID No:5 and SEQ ID No:7), *Mucuna pruriens* (velvet bean, SEQ ID No:9), *Cajanus cajans* (pigeon pea, SEQ ID No:11) and *Quercus petraea* (oak, SEQ ID No:13) derived from WO 2013/166,320A1;
3) *Wisteria* sp. (GenBank: AEK70969), *Robinia pseudoacacia* (GenBank: AEK70968), *Melaleuca alternifolia* (GenBank: AAP40638), *Eucalyptus globulus* (GenBank: BAF02831), *Salix* sp. (GenBank: AEK70970) and a myrcene synthase from *Humulus lupulus* (GenBank: ACI32638) derived from Sharkey list (Sharkey et al., Evolution, 67: 1026, 2013); and
4) 2-methyl-3-buten-2-ol (MBO) synthase (GenBank: AEB53064)(Gray et al., *J Biol Chem,* 286: 20582, 2011) derived from *Pinus sabiniana.*

In addition, several sequences derived from poplar genus were included as a reference.

The homology-based search was performed in GenBank protein databases (nr, pat and env_nr) using Uniport(SwissProt and TrEMBL) and blastp, and was performed in GenBank nucleotide databases (tsa_nt, env_nt and pat) using tblastn, and extracted when E-value is less than 1e-30.

Additionally, Uniprot/SwisProt sequences with InterPro domain annotation of "Terpene synthase, metal binding domain" protein family (PFAM: PF03936, Interpro: IPR005630) were retrieved.

The searched nucleotide sequence was translated into an amino acid sequence by GeneWise program.

tsa_nt (GenBank TSA1) which is a database including cDNA sequence through Transcriptomic study was included in Query database, and in order to increase a usable coverage of a plant genome data, transcriptomic data on plant genomes of which sequences are determined up to date was included.

Accordingly, total 9123 sequences were searched, wherein 278 sequences were searched in Uniprot/SwissProt, 1,989 sequences were searched in Uniprot/TrEMBL, 3,953 sequences were searched in GenBank nucleotide databases, and 2,905 sequences were searched in GenBank protein databases. In order to remove the repeated sequences, sequences having 80% homology with each other clustered.

In order to confirm functional diversity among the searched terpene synthases, multiple sequence alignment (MAS) and phylogenetic tree were made by using script in a unix environment. Sequences were aligned with respect to PFAM domain (PF03936) of a protein family and phylogenetic tree was made based on the MSA using FASTTREE program.

The active site of the isoprene synthase determined based on the structure of *Populus canescens* IpsS (PDB:3n0g) was marked to the MSA. The sequences were aligned by ClustalW, and a conserved phylogenetic tree was constructed with resampling using Genious tree builder.

As the final candidates of the plant-derived sequences, *Ipomoea batatas*-derived sequence and *Elaeocarpus photiniifolius*-derived sequence were determined.

*Ipomoea batatas* sequence has the key amino acids of isoprene synthases W317 (W266 in *I. batatas*), F338 (F287 in *I. batatas*), 5445 (S394 in *I. batatas*), F485 (F433 in *I. batatas*), N505 (N453 in *I. batatas*) and Y565 (Y515 in *I. batatas*)

Multiple sequence alignment of *I. batatas* isoprene synthase sequence together with the reference sequences is shown in FIG. 1*a* and FIG. 1*b*. Alignment of the substrate binding amino acid positions is shown in FIG. 2.

Among the additional new candidates, *Medicago sativa, Fragaria vesca* subsp. *Vesca, Morus notabilis, Populus trichocarpa, Dahlia pinnata, Sesamum indicum* and *Eucalyptus grandis* lacked an amino acid at F338 position(amino acid numbering based on *Populus alba* isoprene synthase), and *Mangifera indica*-derived sequence had an important amino acid at F338, which seemed to have a function of the isoprene synthase.

A multiple sequence alignment (MSA) result to an active site sequence of the isoprene synthase candidates was shown in FIG. 3. Reference isoprene synthase sequences, and four sequences (tricyclene or beta-ocimene synthase) other than the reference isoprene synthases were also included as a reference, and identity % of the sequences was shown in FIG. 5.

Figure 4:
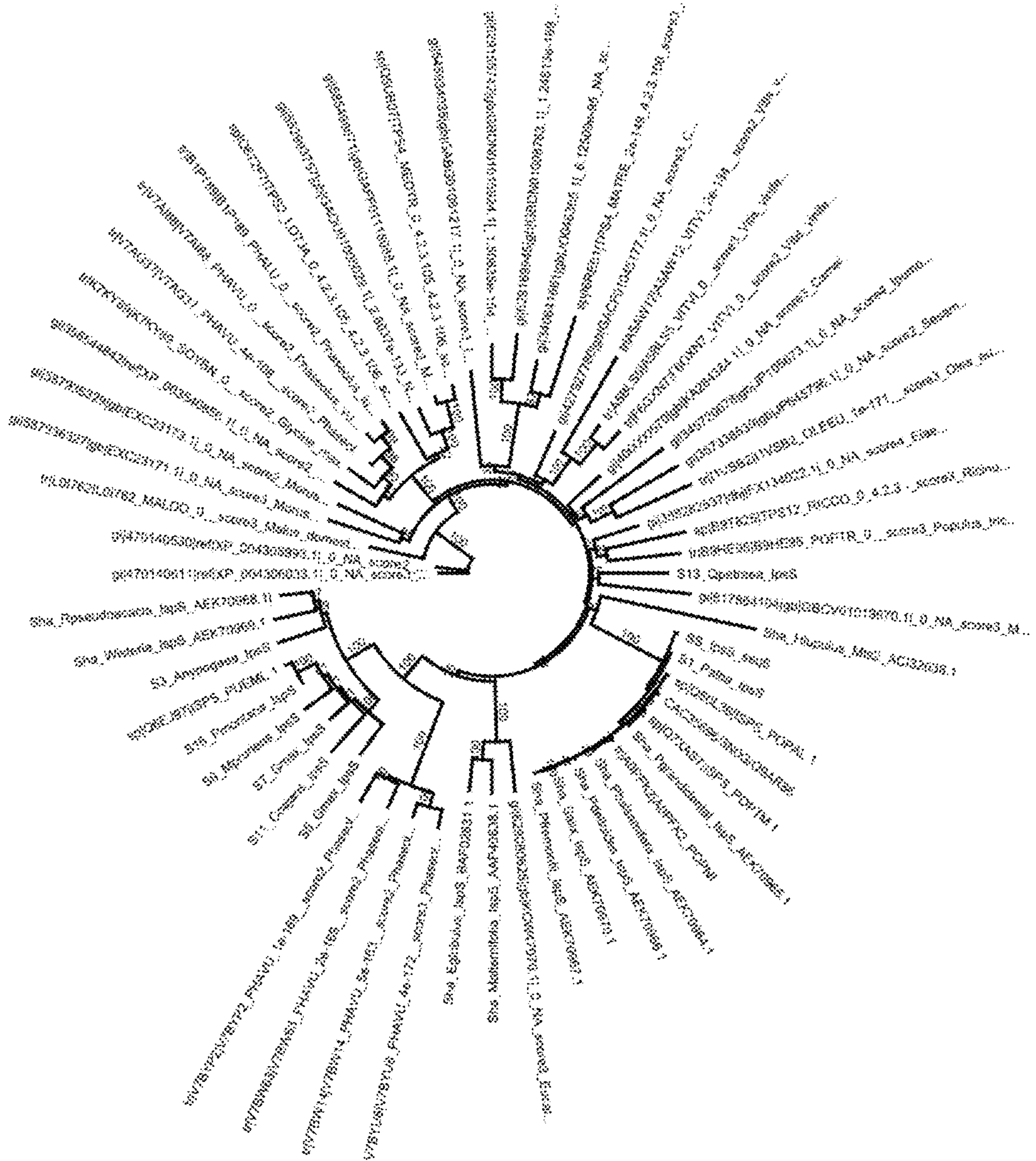
FIG. 4 shows a phylogenetic tree among isoprene synthase candidates.
Figure 5:
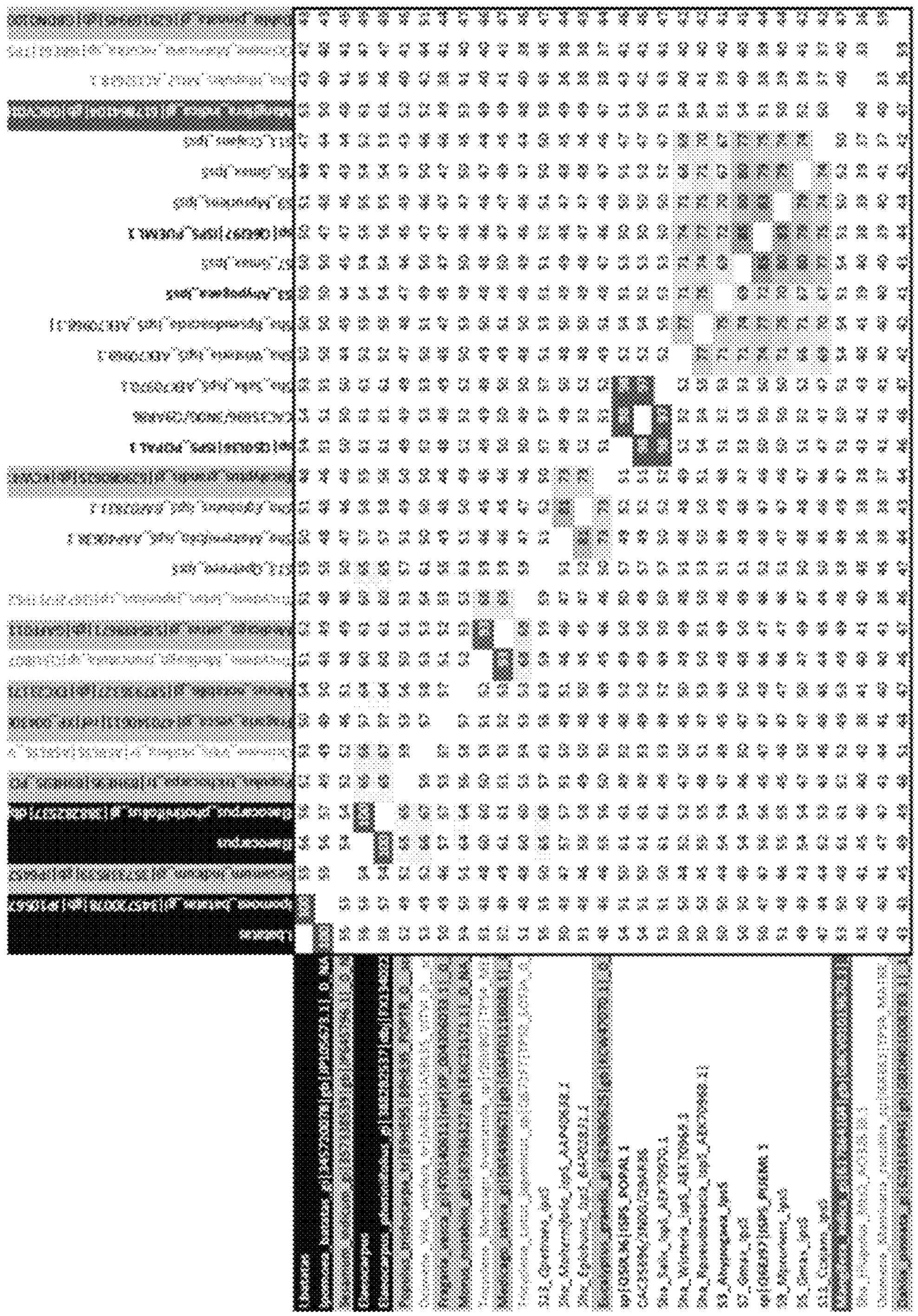
FIG. 5 shows a multiple sequence alignment (MSA) result of the isoprene synthase candidates.

In FIG. 5, the reference isoprene synthases were shown in bold black text, and sequences similar to the reference isoprene synthase were shown in black text, and the candidates known in the related art were shown in black text in italics. Isoprene synthase candidates (*Ipomoea batatas* and *Elaeocarpus photiniifolius*) having 4 points of isoprene scores were shown in white text with black background. Additional new candidate sequences were shown in black text with grey background, and candidates having F388 and 3 points of isoprene score were shown in white text with dark grey background. Sequences with confirmed other functions are shown in grey. The phylogenetic tree was provided with EC number, the biological name, and Blast E-values, and was visualized by Geneious software (FIG. 4).

Example 2: Cloning of Selected Isoprene Synthase Gene Candidate

Since *Ipomoea batatas*- and *Elaeocarpus photiniifolius*-derived nucleotide sequences selected in Example 1 above have a low homology to the known isoprene synthase encoding nucleotide sequences, the polynucleotides were cloned to measure an enzyme activity of protein to be expressed by the polynucleotides.

The isoprene synthase polynucleotide candidates were expressed in *E. coli*, isoprene prepared in a culture medium was measured to confirm an activity of the isoprene synthase, and the known isoprene synthase genes (*P. alba, P. montana* and *A. hypogaea*-derived isoprene synthase genes) were expressed in *E. coli* as a control group. Since cloning and culturing using cyanobacteria require quite a long time to work, they were conducted by selecting *E. coli.*

The genes for cloning were synthesized while removing a portion of encoding N-terminal sequence (N-terminal 40 aa of *E. Pho* and 48aa of *I. bat*) from the gene. In all genes, codon optimization was performed on *Synechocystis* sp. PCC6803 (SEQ ID NO: 3), and then codon optimization was performed on *E. coli*, by using GeneScript.

Figure 6:
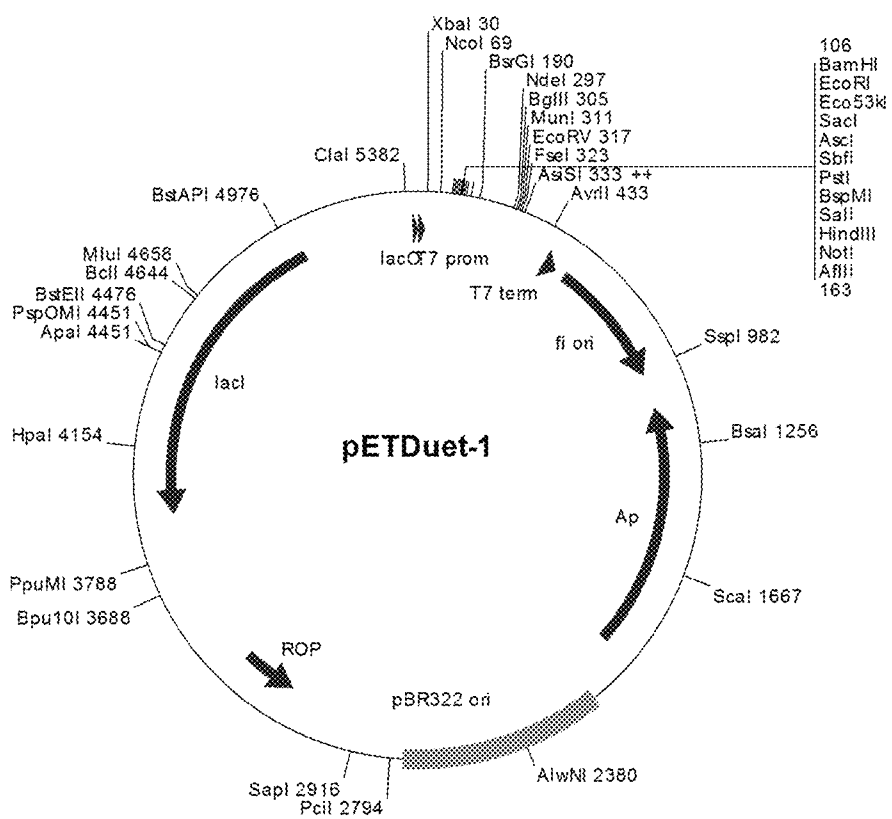
FIG. 6 shows a map of pETDuet-1 vector.

The fabricated construct was cloned in pBAT4 (Peränen J. et al, *Anal. Biochem.,* 236:371-373, 1996) having trc promoter added thereto and cloned in pETDuet-1 (Novagen, USA, FIG. 6) having T7 promoter added thereto, so as to appropriate for expression in cyanobacteria, and when pBAT4 is used as a vector, the *P. alba*-derived polynucleotide and the *I. batatas*-derived polynucleotide were successfully cloned, and when pETDuet-1 is used as a vector, the *I. batatas*-, *E. photiniifolius*-, *P. alba*-, *P. Montana*- and *A. hypogaea*-derived isoprene synthase polynucleotides were cloned.

Example 3: Preparation of Isoprene In Recombinant Microorganism Containing Isoprene Synthase Gene Candidates 3-1: Transformation and Culturing Plasmids containing isoprene synthase polynucleotide candidates cloned in Example 2 above were transformed into *E. coli* BL21, and expression of isoprene synthase was confirmed.

The selected transformants and parent strains were inoculated into an LB liquid medium containing 100 μg/mL ampicillin and cultured at 30° C. (or 37° C.). overnight, then the culture medium was diluted to 1:50, cultured until the OD600 at 30° C. is 0.6 to 0.7, and treated with IPTG so as to have a final concentration of 0.5 mM, thereby inducing an enzyme expression. The culturing was performed for 24 hours using a sealed 22 mL head-space bottle while inoculating the culture medium for 2 mL/bottle. At the same time, the culturing for protein analysis was performed using Erlenmeyer flask.

3-2: Detection and Quantification of Isoprene

Isoprene prepared in *E. coli* strain cloned with isoprene synthase was analyzed by solid-phase microexrction (SPME). An isoprene standard material containing 0.002% 4-tert-butylcatechcol as a stabilizer (Fluka nr529240 CAS 78-79-5) was used, and analyzed using divinylbenzene/carboxen/PDMS (DVB/CAR/PDMS) fiber (2 cm). CTC Combi PAL system (CTC Analytics AG, Switzerland) was used as a sampler, and the combination of Agilent 7890A gas chromatograph (GC, Agilent Technologies, USA) with a5975C mass selective detector (MSD Agilent Technologies, USA) was used. In order to separate isoprene from ethanol which is volatile occurred during the culturing, HP-5, HP-35 (30 m) and BPX5 (60 m) columns were used, and isoprene was eluted by Lipodex (50 m) and HP-Innowax (60 m).

The elution time was 20 minutes, desorption time was 8 minutes, temperature in GC oven was between 40° C. (4 mins) and 70° C. (5° C./min), and the total running time was 16.3 mins. Temperature of the injector was 250° C., MS data were collected in m/z 35 to 350, and mass spectrum of isoprene was confirmed by comparison with NIST08 library.

The basic peak was m/z 67 and the mass peak was m/z 68, and other main fragments had m/z 53, 40 and 39. Calibration curves were measured by spike of isoprene in three different media (LB, BG11 and BG11 without $Na_2CO_3$). The medium had a concentration area of 2~85 ng/2 mL, and the spike was performed on the sample with ethanol having the same amount (10 μl/bottle). The sample was put into a 22 mL head-space bottle used in both of the culturing and the analysis and was analyzed. The quantitative limit of the present invention was 0.5 ng/ml, and the detection limit was lower than the quantitative limit.

Figure 7:
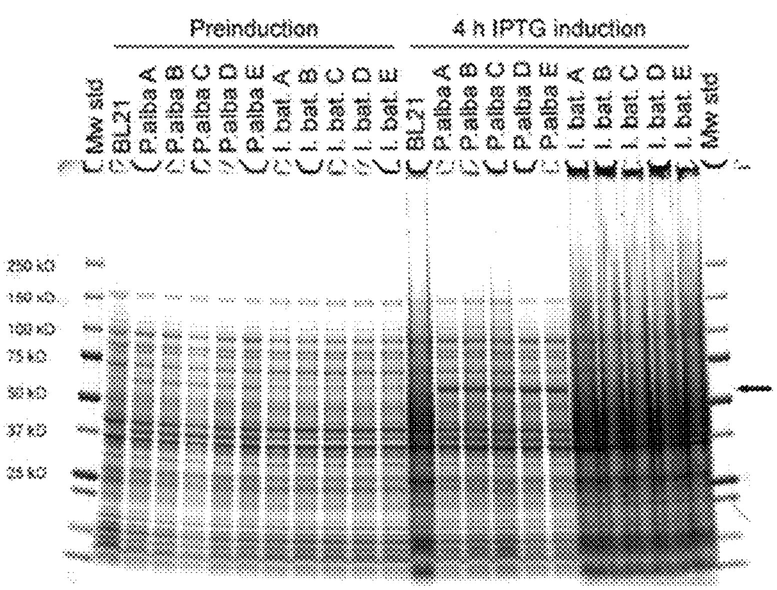
FIG. 7 shows an expression of an isoprene synthase of isoprene synthase clone comprising a pBAT4 construct (trc promoter) of *P. alba*- and *I. batatas*-derived isoprene synthase genes.
Figure 8:
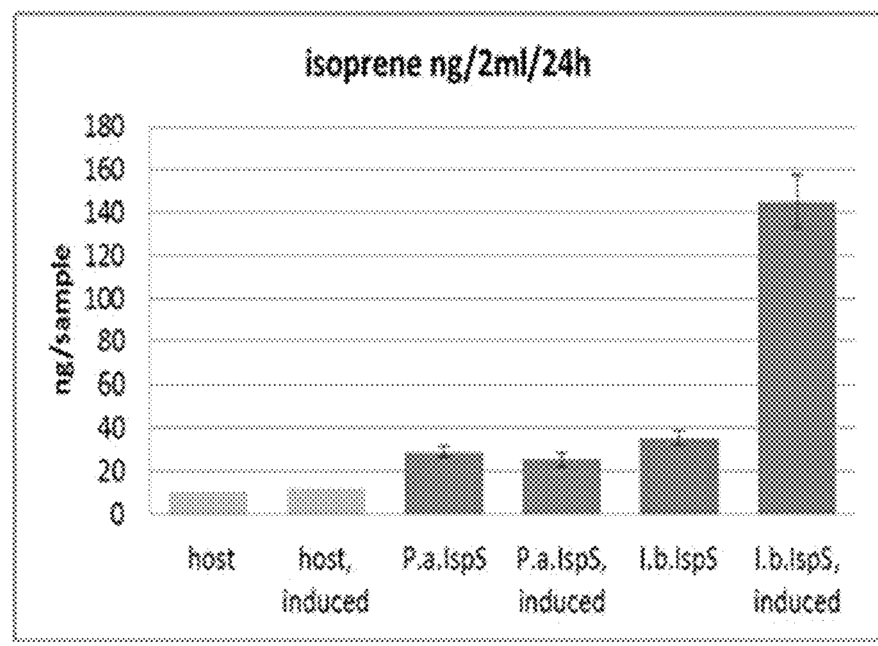
FIG. 8 shows isoprene productivity of the pBAT4 construct (trc promoter) comprising *P. alba*- and *I. batatas*-derived isoprene synthase genes.

Expression in the pBAT4 constructs (trc promoter) of the *P. alba*- and *I. batatas*-derived isoprene synthase genes before and after the induction of the isoprene synthase was shown in Criterion TGX 4-20 gel with GelCode Blue dye (FIG. 7). Expression of the isoprene synthase and preparation of isoprene were confirmed by culturing five clones (A to E) of two constructs. After the induction, preparation of *P. alba*-derived isoprene synthase (64 kDa) was clearly confirmed, but *I. batatas* lysate (62 kDa) was not clearly confirmed due to high viscosity. After 24 hours of the induction, the isoprene prepared by the recombinant *E. coli* was analyzed by SPME method. As a result, it could be confirmed from FIG. 8 that the recombinant *E. coli*-derived sample containing *I. batatas*-derived isoprene synthase had particularly high isoprene productivity.

Figure 9:
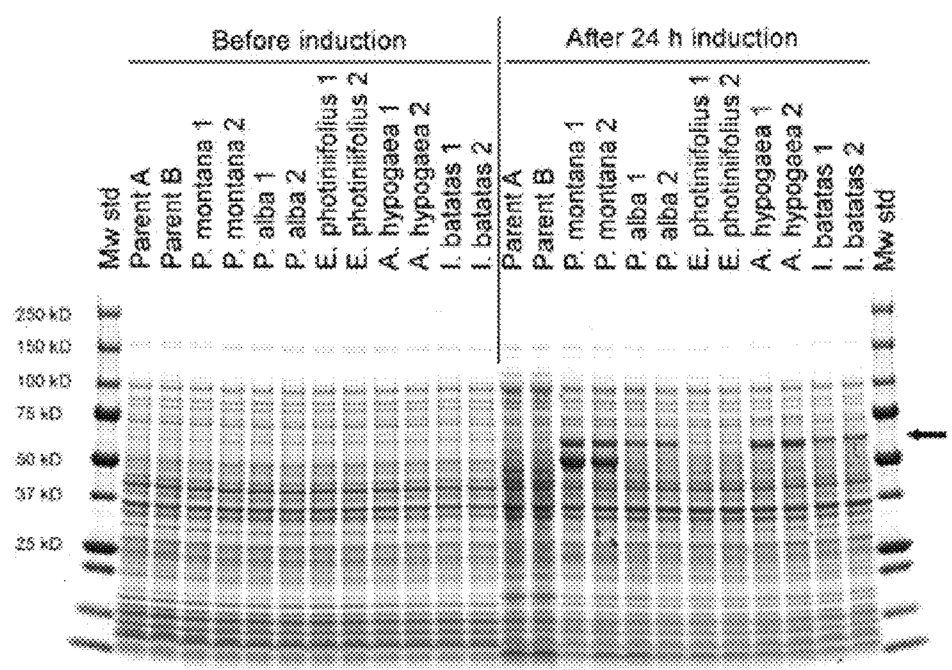
FIG. 9 shows an expression of an isoprene synthase of an *E. coli* strain transformed into a pETDuet-1 vector having five kinds of isoprene synthases (*I. batatas, E. photiniifolius, P. alba, P. montana* and *A. hypogaea*) introduced thereinto.

As a result of confirming expression of the isoprene synthase of the isoprene synthase clone of five kinds (*I. batatas, E. photiniifolius, P. alba, P. montana* and *A. hypogaea*) using pETDuet-1 vector, it could be confirmed from FIG. 9 that after 24 hours of the induction, all strains excluding *E. photiniifolius* showed clear isoprene synthase production.

Figure 10:
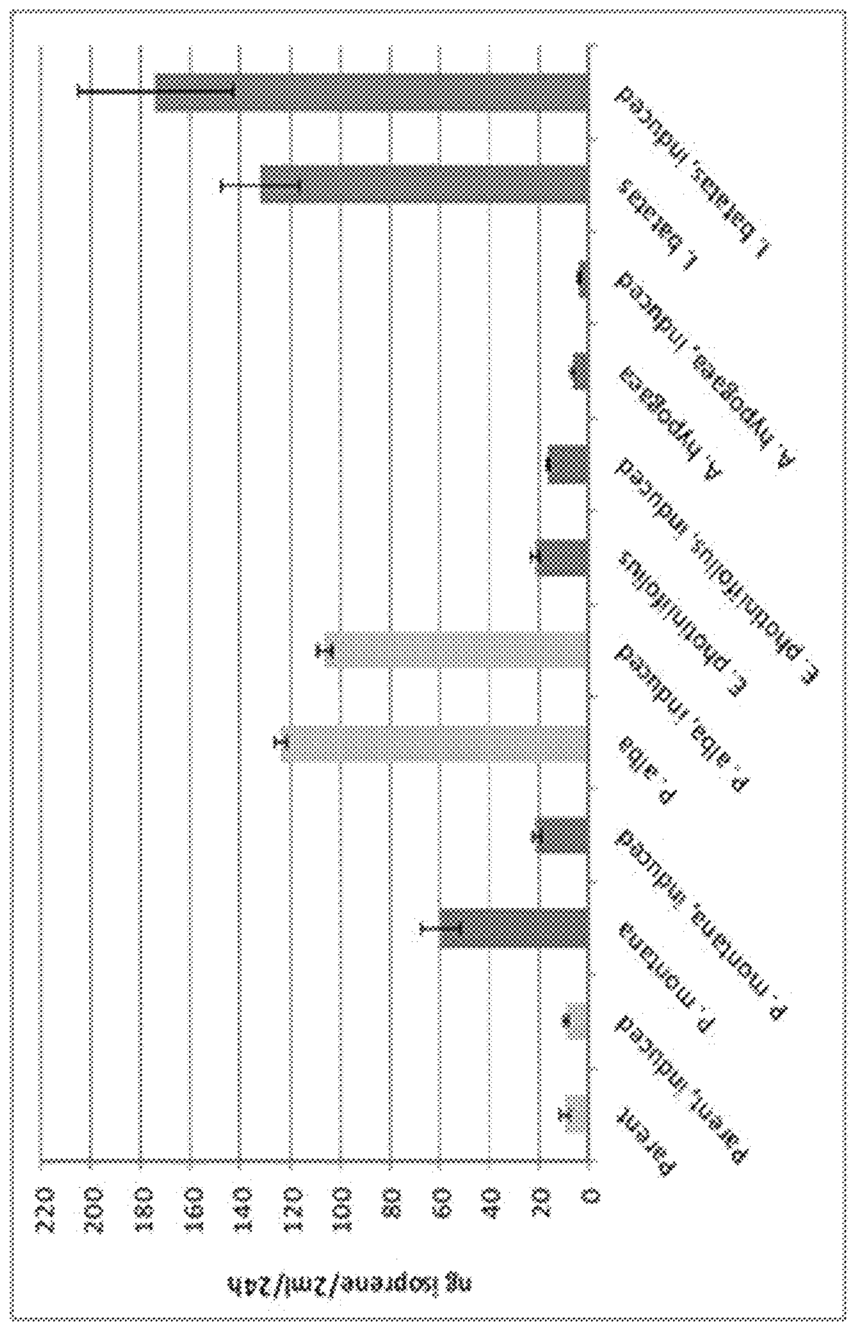
FIG. 10 shows isoprene productivity of an *E. coli* strain transformed into a pETDuet-1 vector, in which five kinds of isoprene synthases (*I. batatas, E. photiniifolius, P alba, P. montana* and *A. hypogaea*) are inserted.

As a result of analyzing the isoprene productivity in the five kinds of recombinant *E. coli*'s after 24 hours of the induction, it could be confirmed from FIG. 10 that high isoprene productivity was shown in *I. batatas*- and *P. alba*-derived isoprene synthases, in particular, the highest isoprene productivity was shown in *I. batatas*-derived isoprene synthase, and in *E. photiniifolius*, an enzyme production was not confirmed in Criterion TGX 4-20 gel, but isoprene was prepared. The preparation of isoprene was not confirmed in *A. hypogaea.*

Figure 11:
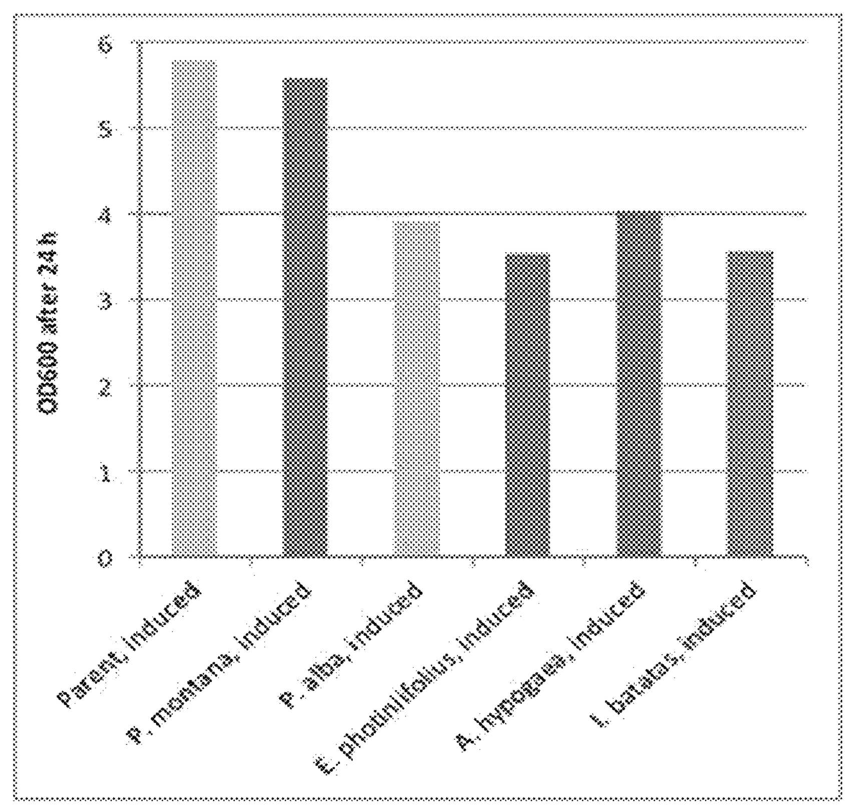
FIG. 11 shows inhibition in growth of an *E. coli* strain transformed into a pETDuet-1 vector, in which five kinds of isoprene synthases (*I. batatas, E. photiniifolius, P alba, P. montana* and *A. hypogaea*) are inserted.

In addition, as a result of confirming growth of each recombinant *E. coli* strain with $OD_{600}$ values, it was confirmed that the growth of each strain was slightly inhibited by expression of the recombinant enzyme (FIG. 11).

Figure 12:
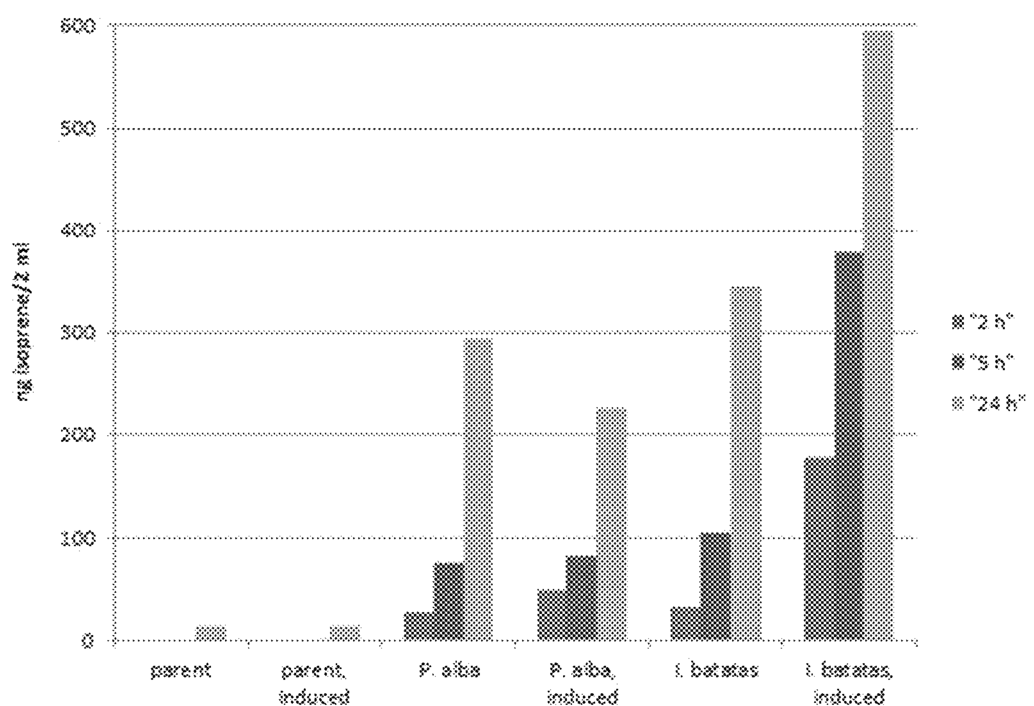
FIG. 12 shows time dependent isoprene productivity after expression of isoprene synthases in an *E. coli* strain transformed into a pETDuet-1 vector in which *I. batatas* of isoprene synthases and *P. alba* of isoprene synthases, respectably, are inserted.
Figure 13:
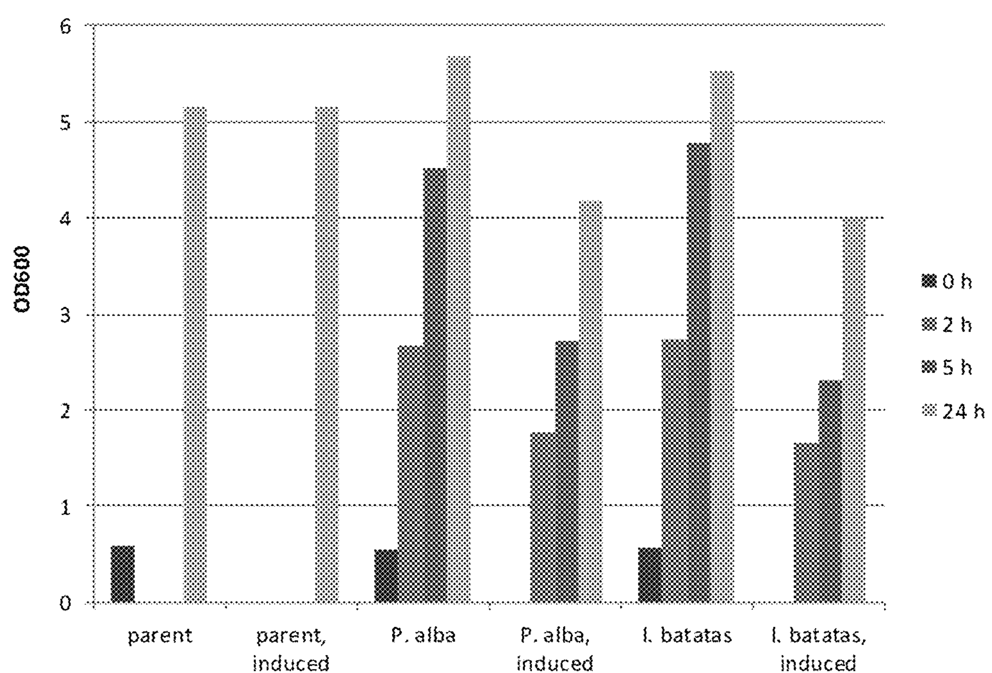
FIG. 13 shows time dependent growth inhibition in of an *E. coli* strain transformed into a pETDuet-1 vector, in which *I. batatas* of isoprene synthases and *P. alba* of isoprene synthases, respectably, are inserted.

Further, FIG. 12 shows time dependent isoprene productivity after expression of isoprene synthases in an *E. coli* strain transformed into a pETDuet-1 vector in which *I. batatas* of isoprene synthases and *P. alba* of isoprene synthases, respectably, are inserted. It could be confirmed that isoprene was accumulated steadily after expression of isoprene synthases and isoprene was also produced in an *E. coli* strain without inducing expression by using IPTG As a result of confirming time dependent growth of strain by using $OD_{600}$ value, after inducing expression by using IPTG in recombinant *E. coli* including IpS derived from *I. batatas* and recombinant *E. coli* including IpS derived from *P. alba*, growth of strain steadily decreases compared to strain without inducing treatment by using IPTG (FIG. 13).

Example 4: *Synechocystis* Sp. Cells Expressing Isoprene Synthase

*Synechocystis* sp. PCC6803 is used as the parent strain and is referred to as the wild type (wt). The wt strain and transformants are maintained on BG-11 agar and in BG-11 liquid medium buffered with Hepes to pH 7.5 and is supplemented with 10 mM bicarbonate and with the antibiotics kanamycin, spectinomycin or chloramphenicol as appropriate. Instead of or in addition to bicarbonate, $CO_2$ enriched cultivation conditions are used to provide the carbon source. *Synechocystis* is cultivated at 30° C. under illumination (10-300 μmol photons $m^{-2}s^{-1}$).

*Synechocystis* sp. is transformed by natural transformation using previously described methods. The presence of the transforming DNA is confirmed by PCR.

Constructs are designed for the expression of isoprene synthase in cyanobacteria. The isoprene synthase is expressed under the transcriptional control of an *E. coli* or a *Synechocystis* promoter, which allows expression of isoprene synthase in cyanobacteria. As an example, the *E. coli* trc or lac promoters or *Synechocystis* sp. psbA promoter and *Synechocystis* terminator or *E. coli* rrnB terminator or phage T7 terminator are used. The *I. batatas* isoprene synthase nucleotide sequence (SEQ ID: No. 2) was codon optimized for expression in *Synechocystis* sp. PCC6803 and synthesized by GenScript (Piscataway, N.J., USA). The expression cassettes for isoprene synthase and the antibiotic resistance marker are flanked by homologous sequences corresponding to a neutral site in the *Synechocystis* sp. genome to facilitate integration of the transforming DNA into the genome by homologous recombination.

Neutral sites e.g. between slr0168 and slr0338 in the *Synechocystis* sp. PCC6803 genome are suitable target loci for introducing the isoprene synthase. Other target sites can be chosen in order to knock out genes that potentially interfere with production of the desired product and its precursors. Genes required for biosynthesis of storage compounds such as glgA or glgC, involved in glycogen biosynthesis, are examples of such genes.

Example 5: *Synechocystis* Sp. Cells Expressing One or More Enzymes of the Mevalonate Pathway In combination with isoprene synthase expression other genes contributing to isoprene production are introduced into *Synechocystis* cells. For example, the idi gene coding for isopentenyl-diphosphate delta-isomerase (EC 5.3.3.2) is introduced to enhance conversion of isopentenyl diphosphate (IPP) to dimethylallyl diphosphate (DMAPP) that is the substrate of isoprene synthase. Optionally one or more genes coding for the mevalonate pathway components, mevalonate kinase (EC2.7.1.36), phosphomevalonate kinase (EC2.7.4.2), pyrophoshomevalonate decarboxylase (EC 4.1.1.33), acetoacetyl-CoA thiolase (EC2.3.1.9), HMG-CoA synthase (EC2.3.3.10) or HMG-CoA reductase (EC1.1.1.34) are cloned under an *E. coli* or *Synechocystis* promoter that allows expression in cyanobacteria. Two or more genes are expressed as a transcriptional fusion under the control of under the transcriptional control of an *E. coli* or a *Synechocystis* promoter. Each open reading frame is preceded by a ribosome binding site (RBS) to allow independent translation of the polypeptides. The above mentioned polynucleotides and the antibiotic resistance marker are flanked by homologous sequences corresponding to the target locus of choice in the *Synechocystis* sp. genome to allow integration of the transforming construct into the genome.

Example 6: *Synechocystis* Sp. Cells Over-Expressing One or More Polypeptides of the Non-Mevalonate Pathway Although cyanobacteria possess the non-mevalonate pathway for synthesising isoprenoid precursors, overexpression of selected pathway components from homologous or heterologous sources will benefit isoprene production. Constructs are designed for the overexpression of the non-mevalonate pathway genes, deoxyxylulose-5-phosphate synthase (DXP synthase; EC2.2.1.7), DXP reductioisomerase (EC1.1.1.267), MEP-cytidyltransferase (EC2.7.7.60), CPD-ME-kinase (EC2.7.1.148), MECDP synthase (1.17.7.1), HMBDP synthase (EC1.17.7.1), HMBDP reductase (EC1.17.1.2), and isopentenyl-diphosphate delta-isomerase (EC 5.3.3.2) in *Synechocystis* sp. are designed using the same principle as described for the mevalonate pathway genes. One or more non-mevalonate pathway genes are introduced into *Synechocystis* sp. in combination with isoprene synthase expression.

Example 7: Production of Isoprene by Recombinant *Synechocystis* Cells Expressing Isoprene Synthase

*Synechocystis* transformants expressing isoprene synthase and optional other genetic modifications are tested for isoprene production using an in vivo assay. Wild type cells are studied in parallel as controls. As an example, cells are grown for 4 days at 30° C. with 100 rpm shaking under continuous illumination in BG11 liquid medium supplemented with bicarbonate as the carbon source and the appropriate antibiotics. Cells from 20 ml cultivation are harvested by centrifugation and suspended in 8 ml of BG11 medium supplemented with bicarbonate and antibiotics as appropriate in 20 ml GC-MS bottles which are sealed air-tight. When isoprene synthase is expressed under control of an IPTG inducible promoter 0.5 mM IPTG is added into to medium to induce isoprene production. Cultivations are also carried out without IPTG The bottles are incubated at 30° C. with 100 rpm shaking for up to 240 h. Samples are taken at regular intervals during the cultivation. At each time point a bottle is removed, the cultivation is heated at 40° C. and isoprene is measured from the head space of the bottle using the GC-MS method described earlier for *E. coli.*

Isoprene production into the medium in aerobic cultures of *Synechocystis* is also analysed. The culture medium is sampled periodically and the samples are transferred into GC-MS vials, heated at 40° C., and isoprene is measured off-line from the head space of the bottle using the GC-MS method described earlier for *E. coli.*

Example 8: Production of Isoprene by Recombinant *Synechocystis* Cells in a Bioreactor The inocula for bioreactor cultivation are grown at 30° C. with 100 rpm shaking under continuous illumination in BG11 liquid medium supplemented with bicarbonate as the carbon source and the appropriate antibiotics. The inoculum is transferred into BG11 medium in a photobioreactor. Bicarbonate or $CO_2$ gas is used as the carbon source. The photobioreactor is equipped with adjustable lightning and controllable gas inlet and outlet. The cells are grown at 30° C. and the cultivation is mixed with agitation or gas bubbling. Isoprene production is analysed off-line. The culture medium is sampled periodically and the samples are transferred into GC-MS vials, heated at 40° C., and isoprene is measured from the head space of the bottle using the GC-MS method described earlier for *E. coli*. Isoprene is harvested from the bioreactor flushing the reactor periodically with $CO_2$ as described (Bentley and Melis, 2012, Biotechnol Bioeng 109:100-109).

Example 9: Construction of Isoprene Producing *Saccharomyces Cerevisiae* Strains Constructs are designed for the expression of isoprene synthase in *S. cerevisiae*. The isoprene synthase nucleotide sequence is expressed from an autonomously replicating multi-copy vector containing a 2-micron replication origin or an ARS sequence, a centromeric vector, or integrated into the genome in one or more copies. Optional other genetic modifications such as overexpression of isopentenyl-diphosphate delta-isomerase (IDI) or mevalonate pathway or non-mevalonate pathway components are also introduced into *S. cerevisiae*. The constructs can be assembled by traditional cloning methods or by recombination cloning. For example, *S. cerevisiae* strain FY834 is used for recombination cloning (Winston, Dollard and Ricupero-Hovasse, 1995). *S. cerevisiae* strain H2798 (ura-) is the parental strain which is used for the production of ispS isoprene.

Figure 14:
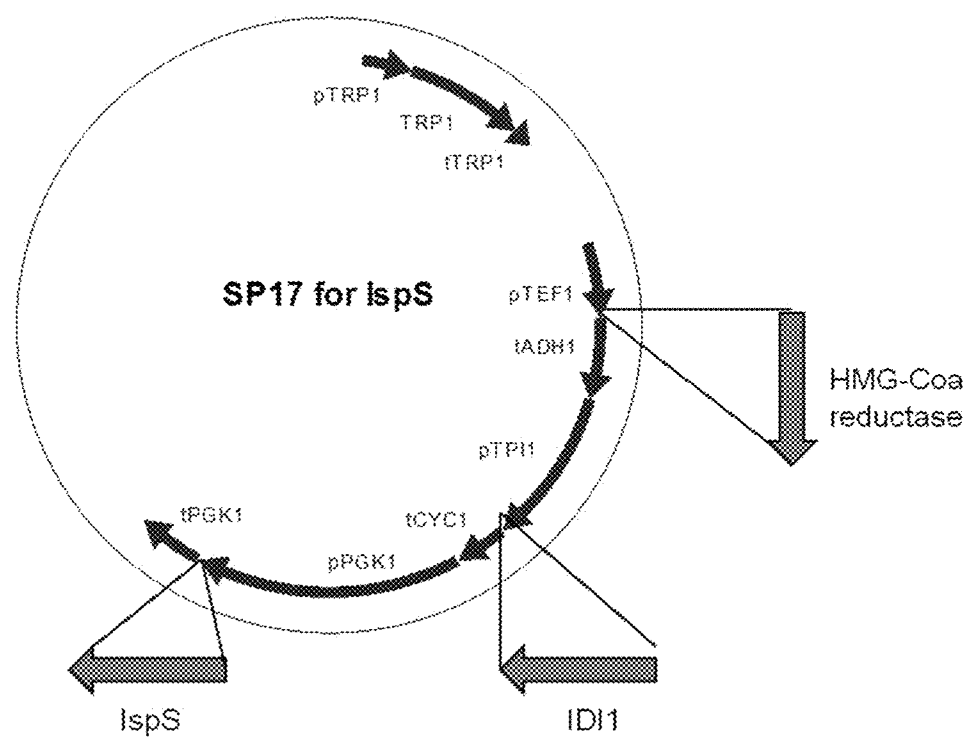
FIG. 14 shows plasmid for expression of IspS, IDI and HMG-CoA reductase in *S. cerevisiae.*

A vector, named SP17, containing three *S. cerevisiae* promoter-terminator pairs cloned into the pRS426 plasmid, is used. The truncated Hmg-CoA reductase (Polakowski et al. 1998, Appl Microbiol Biotechnol. 49:66-71) is amplified by PCR using the oligonucleotides TAGCAATCTAATCTAAGTTTTAATTACAAACTCGAGTAAAATGGACCAA TTGGTGAAAACTG (SEQ ID NO: 4) and CCAAACCTCTGGCGAAGAAGT CCAAAGCTGTCGACGGATTTAATGCAGGTGACGG (SEQ ID NO: 5) and cloned into a SP17 vector between e.g. the TEF1 promoter and ADH1 terminator by homologous recombination. The IspS nucleotide sequence of *I. batatas* (SEQ ID NO: 2) is codon optimized for expression in *S. cerevisiae* and synthesized by GenScript, amplified by PCR, and inserted between e.g. the PGK1 promoter and PGK1 terminator. The IDI nucleotide sequence is amplified by PCR and cloned between e.g. TPI1 promoter and CYC1 terminator by homologous recombination. Schematic representation of the construct is shown in FIG. 14. *S. cerevisiae* are transformed using the LiAc/PEG method (Gietz and Woods, 2002, Methods in Enzymology 350: 87-96). The resulting plasmid is transformed into *S. cerevisiae* strain and selected on synthetic complete medium lacking uracil (SCD-Ura). The presence of the transforming DNA is confirmed by PCR.

The *S. cerevisiae* IspS transformants are propagated aerobically at 30° C. with 250 rpm shaking in SC-Ura medium containing glucose, galactose or glycerol as the carbon source to produce the biomass for isoprene production. For isoprene production, aliquots of the precultures are transferred into fresh SC-Ura medium containing glucose, galactose or glycerol in tightly sealed flasks, which enable harvesting of isoprene. The bottles are incubated at 30° C. with 250 rpm shaking for up to 96 h. Samples are taken at regular intervals during the cultivation. At each time point a bottle is removed, the cultivation is heated at 40° C. and isoprene is measured from the head space of the bottle using the GC-MS method described earlier for *E. coli.*

Figure 15:
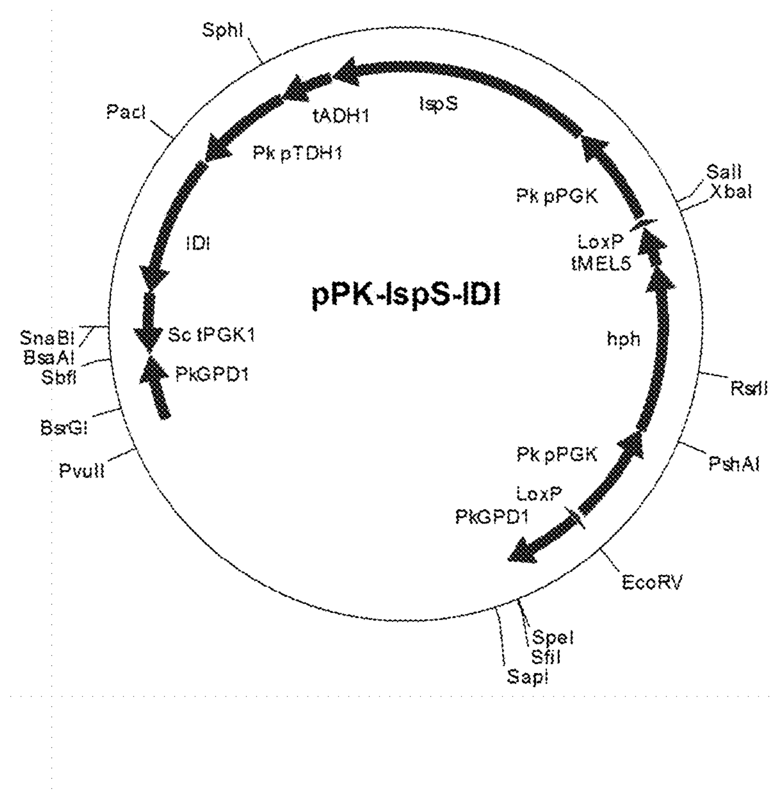
FIG. 15 shows plasmid for expression of IspS, and IDI in *P. kudriavzevii.*

Example 10: Construction of *Pichia Kudriavzevii* Strains for Isoprene Production Synthetic *I. batatas* IspS gene, optimized for expression in *S. cerevisiae*, was obtained from GenScript (Piscataway, N.J., USA). The IspS polynucleotide was introduced into *P. kudriavzevii* strain ATCC32196 under the PGK1 or TDH1 promoters of *P. kudriavzevii* together with the isopentenyl-diphosphate delta-isomerase (IDI) gene. The *P. kudriavzevii* PGK1 promoter and *S. cerevisiae* MEL5 terminator controlled the expression of the hygromycin resistance marker that was used for selection of transformants. The Pk promoters were amplified from the genomic DNA of *P. kudriavzevii* strain ATCC32196 essentially as described in US 2009/0226989 A1. Terminators from *S. cerevisiae* and *P. kudriavzevii* were used. The marker cassette was flanked by loxP sites to enable removal and re-use of the marker. The isoprene synthase and marker expression cassettes were flanked by homologous sequences corresponding to the *P. kudriavzevii* GPD1 locus to enable integration in the GPD1 locus. The resulting construct contained P.k. GPD1 5' flanking region-P.k. PGK1 promoter-MEL5 or hygromycin marker-MEL5 terminator-P.k. promoter-isoprene synthase nucleotide sequence-Pk. or S.c. terminator-Pk. promoter-IDI-P.k. or S.c.-P.k. GPD1 3' flanking region (FIG. 15).

Figure 16:
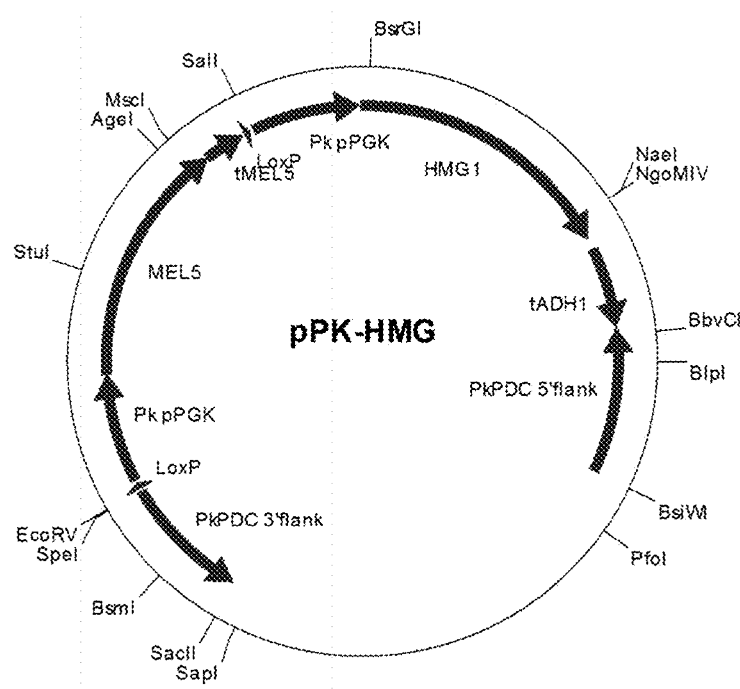
FIG. 16 shows plasmids for expression of HMG-reductase in *P. kudriavzevii.*

A HMG-CoA reductase (Polakowski et al. 1998, Appl Microbiol Biotechnol. 49:66-71) was co-expressed with the isoprene synthase in *P. kudriavzevii* under control of the *P. kudriavzevii* promoter. The resulting construct contained P.k. PDC1 3' flanking region-Pk. promoter-MEL5 or hygromycin marker-MEL5 terminator-P.k. promoter-HMG-CoA reductase nucleotide sequence-P.k. terminator-P.k. PDC1 5' flanking region (FIG. 16).

The resulting constructs were transformed into *P. kudriavzevii* strain ATCC32196 using the LiAc/PEG method. The transformants were selected based on blue colour on yeast peptone dextrose (YPD) medium containing 5-bromo-4-chloro-3-indolyl-α-D-galactopyranoside (X-alpha-gal) or for growth on melibiose, or for growth on YPD medium containing hygromycin essentially as described in US 2009/0226989 A1. The presence of the transforming DNA was confirmed by PCR. Transformants were cultured aerobically on synthetic complete medium or yeast peptone (YP) medium containing glucose, fructose or glycerol as the carbon source. For isoprene analysis, aliquots of the precultures are transferred into fresh medium in tightly sealed GC-MS bottles retaining isoprene. The bottles were incubated at 30° C. with 100 rpm shaking for up to 96 h. Samples were taken at regular intervals during the cultivation. At each time point a bottle was removed, the cultivation was heated at 40° C. and isoprene was measured from the head space of the bottle using the GC-MS method described earlier for *E. coli* except that the medium used for the calibration curve was YP-medium containing 0.5% ethanol.

The expression vector for an N-terminally truncated *S. cerevisiae* HMG1 was named pPK-HMG (FIG. 16, SEQ ID NO: 6) and targeted for integration into the *P. kudriavzevii* PDC1 locus. The N-terminally truncated HMG1 gene (SEQ ID NO: 34) was amplified from genomic DNA of *S. cerevisiae* W303 by PCR using primers (5'-AGCGCGGATCCATGGACCAATTGGTGAAAACTGAAG) (SEQ ID NO: 7) and (5'-AGCGCGGATCCCACATGGTGCTGTTGTGCTTC) (SEQ ID NO: 8) and expressed under the control of the *P. kudriavzevii* PGK1 promoter and *S. cerevisiae* ADH1 terminator. The expression construct with the MEL5 marker and *P. kudriavzevii* PDC1 homology regions was released with NotI from plasmid pPK-HMG and transformed into *P. kudriavzevii* VTT-C-79090T (ATCC32196) using the lithium acetate method and colonies were screened based on blue colour on YPD-agar containing 40 μg/ml 5-bromo-4-chloro-3-indolyl-α-D-galactopyranoside. A transformant Pk/HMG1 was selected for continuation.

The vector for expression of *I. batatas* IspS and *S. cerevisiae* IDI1 was named pPK-IspS-IDI (FIG. 15; SEQ ID NO: 9). The integration was targeted to the *P. kudriavzevii* GPD1 locus. The *P. kudriavzevii* GPD1 homology regions were amplified by PCR from genomic DNA of *P. kudriavzevii* VTT-C-79090T (ATCC32196). The *I. batatas* IspS gene with a C-terminal StrepII-tag was codon optimized for expression in *S. cerevisiae* and synthesized by Genscript (Hongkong) (SEQ ID NO: 33). *I. batatas* IspS was expressed under control of the *P. kudriavzevii* PGK1 promoter and *S. cerevisiae* ADH1 terminator. The IDI1 gene (SEQ ID NO: 35) was amplified by PCR from genomic *S. cerevisiae* DNA using primers 918IDISc-F (5'-CTTTTTACAACAAATATAAAACCAAAAGCGGCCGCTTAATTAAAAAATGACTGCCGACAACAATAGTATG) (SEQ ID NO: 10) and C031_919new_IDISc_R (5'-AGAGACATGGGAGATCCCGCGGGCGGCCGCTTAATTAATTATAGCATTCTATGAATTTGCC) (SEQ ID NO:11), and placed under the control of the *P. kudriavzevii* TDH1 promoter and *S. cerevisiae* PGK1 terminator. The expression construct with a hygromycin resistance marker and *P. kudriavzevii* GPD1 homology regions was released with NotI from plasmid pPK-IspS-IDI and transformed into *P. kudriavzevii* VTT-C-79090T (ATCC32196) and into *P. kudriavzevii* Pk/HMG1 using the lithium acetate method (Gietz et al. 1992, Nucleic Acids Res 20:1425-1425) and colonies were selected on YPD-agar containing 450 μg/ml hygromycin B as the selective agent. Transformed colonies Pk/IspS+IDI1-69, Pk/IspS+ID1I-72, Pk/ISpS+IDI1-74 and Pk/IspS+IDI1+HMG1-79 were isolated and tested for isoprene production.

Figure 18:
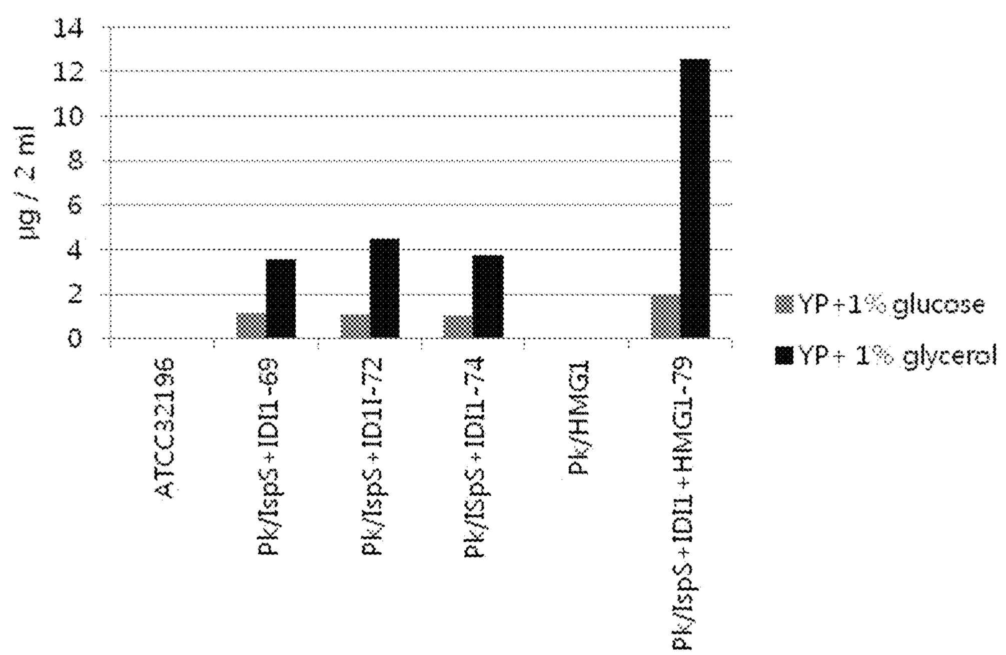
FIG. 18 shows isoprene production by *P. kudriavzevii* transformants in YP medium containing 1% glucose (grey) or 1% glycerol (black) as the carbon source.

*P. kudriavzevii* VTT-C-79090T (ATCC32196) and the Pk/HMG1, Pk/IspS+IDI1 and Pk/IspS+IDI1+HMG1 transformants were grown in YPD medium o/n at 30° C. Cells were collected by centrifugation and suspended in YP-1% glucose or YP+1% glycerol to an $OD_{600}$=3.2 ml aliquots were sealed in 22 ml headspace bottles and incubated o/n at 30 with 100 rpm shaking. Isoprene production was measured as described above except that the isoprene standards were prepared in YP-medium containing 0.5% ethanol. Isoprene concentrations measured are shown in FIG. 18. FIG. 18 shows isoprene production by *P. kudriavzevii* transformants in YP medium containing 1% glucose (grey) or 1% glycerol (black) as the carbon source. All transformants expressing IspS and IDI1 produced isoprene while the parent strain and the strain expressing only HMG1 did not produce detectable isoprene. The amount of isoprene measured ranged from 1 to 12 μg in the 2 ml samples depending on the strain and cultivation conditions. More isoprene was produced on YP-glycerol medium than on YP-glucose medium. The presence of HMG1 in addition to IspS and IDI1 increased isoprene production approximately 3-fold in YP-glycerol medium and 2-fold in YP-glucose medium.

Example 11: Construction of *Trichoderma Reesei* Strains Overexpressing an Isoprene Synthase for Isoprene Production I Synthetic *I. batatas* IspS gene, optimized for expression in *T. reesei*, is obtained from GenScript (Piscataway, N.J., USA) (SEQ ID NO: 36). The codon optimized IspS polynucleotide was introduced into *T. reesei* strain Rut-30 under the control of gpdA promoter of *Aspergillus nidulans* or under the control of the cbh1 promoter of *T. reesei*.

The resulting constructs contained the *T. reesei* cbh1 5' flank region-cbh1 promoter—isoprene synthase—nucleotide sequence *A. nidulans* gpdA promoter hygromycin resistance marker (hph) and *A. nidulans* trpC terminator—*T. reesei* cbh1 terminator and 3' flank region. The resulting constructs were transformed into *T. reesei* using the PEG-mediated protoplast transformation. The transformants were selected based on hygromycin resistance. Instead of hph, the acetamidase *A. nidulans* amdS gene can be used as the selective marker and the transformants were selected based on the ability to use acetamide as the sole nitrogen source.

Alternatively, the isoprene synthase was expressed under the *A. nidulans* gpdA promoter. The codon optimized isoprene synthase polynucleotide was cloned into an expression vector containing the *A. nidulans* gpdA promoter—isoprene synthase—nucleotide sequence—*A. nidulans* trpC terminator—*A. nidulans* gpdA promoter hygromycin resistance marker (hph) and *A. nidulans* trpC terminator. Schematic view of the plasmid used for transformation was shown in FIG. 16. The transformants were purified from colonies originating from single spores, and the integration of the expression cassette into the genome was confirmed by PCR amplification of the expression cassette. The polynucleotides were integrated into the cbh1 locus or into a non-homologous site in *T. reesei* genome.

*T. reesei* transformants containing the ispS polynucleotide were cultivated in shake flasks in medium containing 7.6 g/L $(NH_4)_2SO_4$ 15.0 g/L $KH_2PO_4$, 2.4 mM $MgSO{\cdot}7H_2O$, 4.1 mM $CaCl_2{\cdot}H2O$, 3.7 mg/L $CoCl_2$, 5 mg/L $FeSO_4{\cdot}7H_2O$, 1.4 mg/L $ZnSO_4{\cdot}7H_2O$, 1.6 mg/L $MnSO_4{\cdot}7H_2O$, and a 10 g/L carbon source or a mixture of carbon sources selected from cellulose, xylan, glucose, lactose, glycerol, galactose, sorbose, sorbitol, xylose, arabinose or 0.7 mM sophorose. The pH of the medium was adjusted to 4.8 by addition of KOH. The cultures were inoculated with $8\times10^7$ spores/200 ml medium and grown for up to 7 days in conical flasks at 28° C. with shaking at 250 rpm. The culture medium was sampled periodically and the samples were transferred into GC-MS vials, heated at 40° C., and isoprene was measured off-line from the head space of the bottle using the GC-MS method described earlier for *E. coli*.

Alternatively, the aliquots of the culture transferred into fresh medium in tightly sealed bottles. The bottles were incubated at 28° C. with 250 rpm shaking for up to 96 h. Samples were taken at regular intervals during the cultivation. At each time point a bottle was removed, the cultivation was heated at 40° C. and isoprene was measured from the head space of the bottle using the GC-MS method described earlier for *E. coli*.

Example 12: Construction of *Trichoderma Reesei* Strains Overexpressing an Isoprene Synthase for Isoprene Production II Strains

*Escherichia coli* DH5α (Life Technologies) was used for propagation of the plasmids. *Trichoderma reesei* QM6a (VTT-D-071262T, ATCC13631), RutC-30 (VTT-D-086271, ATCC56765), and M122 (RutC-30 mus53Δ) were obtained from VTT Culture Collection (Espoo, Finland). Spore suspensions were prepared by cultivating the fungus on potato-dextrose plates (BD, Sparks, Md., USA) for 5-7 days, after which the spores were harvested, suspended in a buffer containing 0.8% NaCl, 0.025% Tween-20 and 20% glycerol, filtered through cotton and stored at −80° C.

Expression Vector

Figure 19:
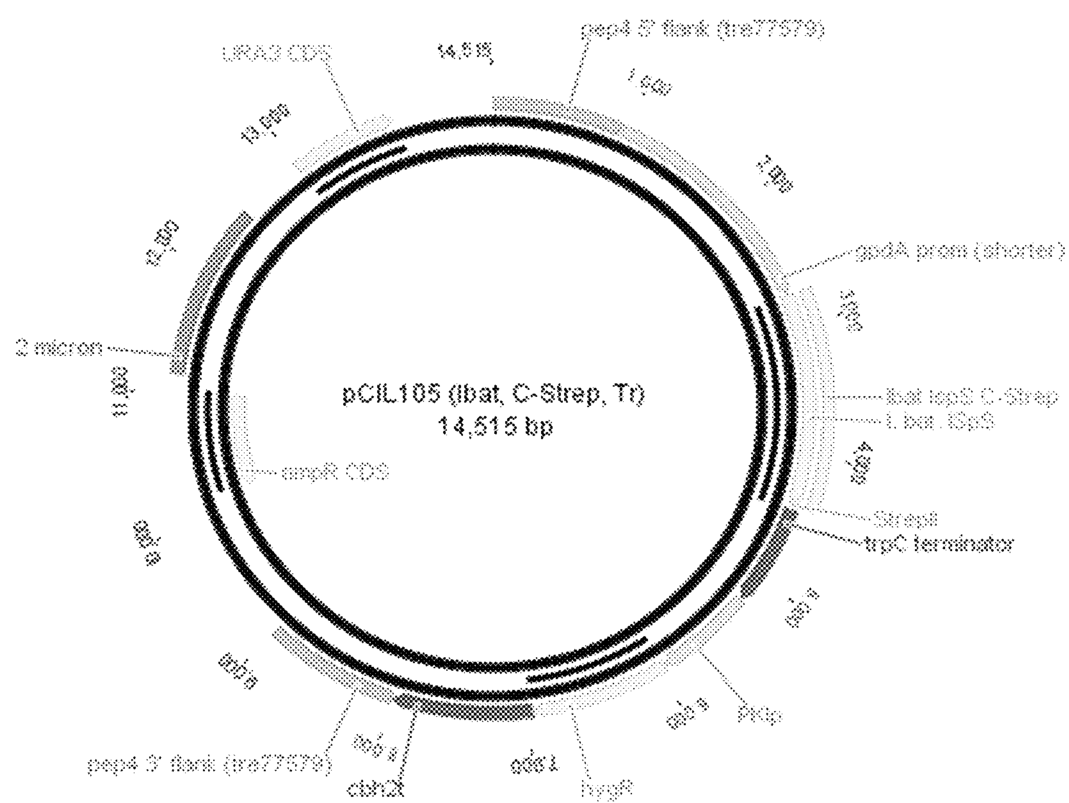
FIG. 19 shows plasmid pCIL105 for expression of *I. batatas* IspS in *T. reesei.*

The vector for expression of *I. batatas* IspS in *T. reesei* was named pCIL-105 (FIG. 19 SEQ ID NO:12)). The backbone for the expression vector contained 5' and 3' flank regions (<1000 bp) of the *T. reesei* pep4 (tre77579) gene in pRS426 (ATCC77107) vector background. The primer sequences indicating the start and end regions for both pep4 flanks are shown in Table 1. The selection marker (pyr4) in the vector backbone pCIL102 was removed by NotI digestion and replaced by hygromycin resistance cassette obtained from plasmid pCIL-107 by NotI digestion. The gene encoding *I. batatas* isoprene synthase with a C-terminal StrepII-tag was obtained from *E. coli* expression plasmid pCIL41 by NdeI-AvrII digestion. The *Aspergillus nidulans* gpdA promoter, *A. nidulans* trpC terminator and a bridge fragment (part of pep4 3' flank) were produced by PCR using primers in Table 1 and plasmid pCIL104 containing these elements as templates. PCR amplification was carried out with KAPA HiFi HotStart ReadyMix PCR kit (KAPA Biosystems). All fragments were separated with agarose gel electrophoresis and isolated with a gel extraction kit (Qiagen). The PCR fragments contained 30 bp or 40 bp overlapping sequences needed for cloning the expression construct using homologous recombination system in yeast. The vector backbone and the appropriate digestion and PCR fragments were transformed into *S. cerevisiae* (strain H3488/FY834) according to Gietz, R. D., and Woods, R. A. (2002, Guide to Yeast Genetics and Molecular and Cell Biology, Pt B 350, pp. 87-96). The plasmid DNA from the yeast transformants was rescued by transformation into *E. coli* and checked from a few clones by digestion. The clone taken further was verified by sequencing and named pCIL105 (SEQ ID NO: 12).

Strain Generation

Figure 20:
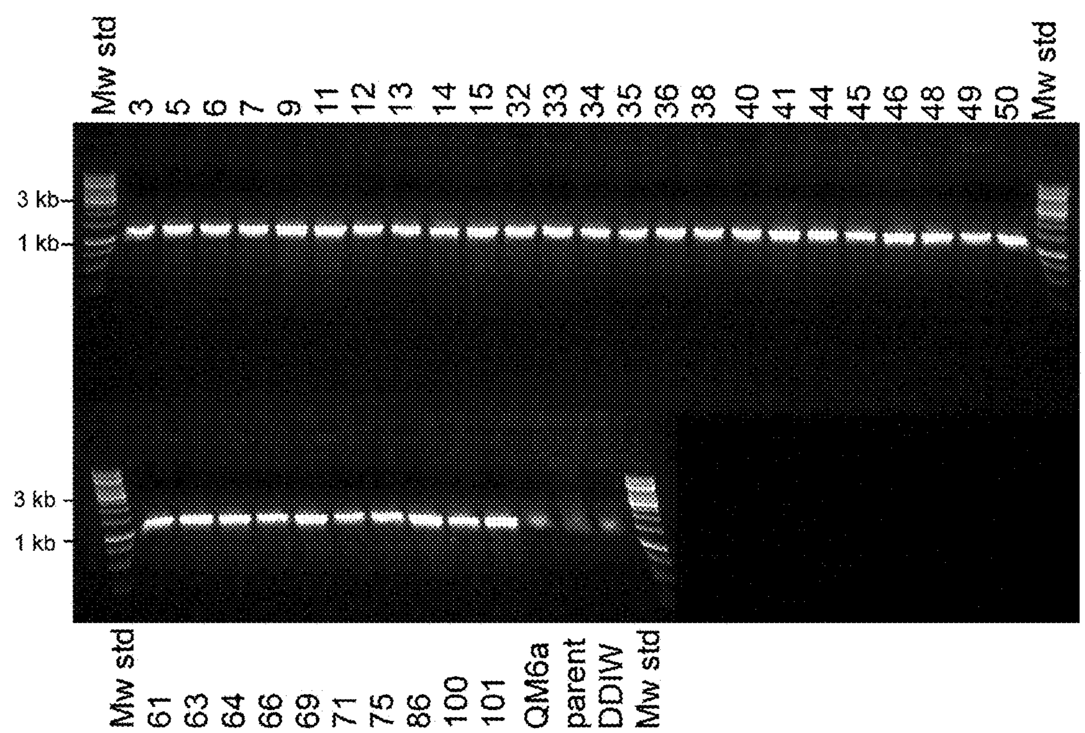
FIG. 20 shows PCR analysis for the presence of the IspS expression cassette in *T. reesei* transformed with pCIL105. Wild type strain QM6a, parent and DDIW are negative controls.

For *T. reesei* transformation, the expression construct was released from pCIL105 with MssI and the correct fragment was purified from agarose gel using QIAquick Gel Extraction Kit (Qiagen). *T. reesei* strain RutC-30 or *T. reesei* strain M122 (RutC-30 Amus53) was transformed with 5 μg of expression cassette fragment according to Penttilä et al. 1987 (Gene 61: 155-164). Transformants were selected on *Trichoderma* minimal medium containing 125 μg/ml hygromycin B (Calbiochem). The transformants were streaked onto *Trichoderma* minimal medium agar with 0.1% (v/v) Triton X-100 and 150 μg/ml Hygromycin B and cultivated at +28° C. Transformants growing on selective plates were screened by PCR for correct 5' and 3' integration or for the presence of the IspS expression cassette (FIG. 20) somewhere else in the genome using the primers shown in Table 2. FIG. 20. shows PCR analysis for the presence of the IspS expression cassette in *T. reesei* transformed with pCIL105. Wild type strain QM6a, parent and DDIW are negative controls. For PCR, internal primers (SEQ ID NO: 31 and SEQ ID: NO 32) shown in Table 2 were used. The expected product size was approximately 1.1 kb.

TABLE 1

Primers used to generate fragments for cloning the expression vector pCIL105 for *I. batatas* IspS-C-StrepII.

| Primer | Sequence | Product |
|---|---|---|
| 77579_5f | TCAGGTCAACCACCGAGGAC (SEQ ID NO: 13) | pep4 5'flank |
| 77579_5r | TGAATGGGATGGTTCGATTG (SEQ ID NO: 14) | |
| 77579_3f | AGGTAGACGCTTTGCGAGTG (SEQ ID NO: 15) | pep4 3'flank |
| 77579_3r | TGAACTGACGCGGACTGA (SEQ ID NO: 16) | |

TABLE 1-continued

Primers used to generate fragments for cloning the expression vector pCIL105 for *I. batatas* IspS-C-StrepII.

| Primer | Sequence | Product |
|---|---|---|
| C017_gpdA_rec_for | CCTCTGGCAGCAATCGAACCATCCCATTCATTAATTAA GCTCCTTATTGAAGTCGGAGG (SEQ ID NO: 17) | gdpA prom |
| C018_gpdA_rec_rev | ATGAGGAGGGTTGATAGTTTGCTGAGCGGCGGGCAGT CATGATGTCTGCTCAAGCGGG (SEQ ID NO: 18) | |
| C019_trpC_rec_for | TAATCCAGTGGAATGGTCCCACCCACAATTTGAAAAG TAAGATCCACTTAACGTTACTGAAATCA (SEQ ID NO: 19) | trpC term |
| C020_trpC_rec_rev | AAGGGGACCGGCCGCTAGTCTCACCGTTATGCGGCCG CTTAATTAAGAGTGGAGATGTGGAGTGGG (SEQ ID NO: 20) | |
| C021_pep4_3frec_for | GATAACCCATCGGCAGCAGATGATAATGATTCCGCAG CACGCGGCCGCAGGTAGACGCTT (SEQ ID NO: 21) | pep4 bridge |
| C022_pep4_3f rev | GAGGTGCCAAAGCCGTTTCG (SEQ ID NO: 22) | |

TABLE 2

Primers used to screen for correct integration of the expression cassette or the presence of the IspS cassette in the *T. reesei* genome.

| Primer | Sequence | Product |
|---|---|---|
| T302_77579_5int | GATTCATCACAGGGGCAGTC (SEQ ID NO: 23) | 5'integration |
| T624_gpdA_seqR1 | CTCCATATTCTCCGATGATGC (SEQ ID NO: 24) | |
| T302_77579_5int | GATTCATCACAGGGGCAGTC (SEQ ID NO: 25) | 5'integration |
| C046_gpdA_rev | TATCCTCTTGACACCGCTCC (SEQ ID NO: 26) | |
| T415_77579_3screen | ACGCCGTTGCTGAGCCTTG (SEQ ID NO: 27) | 3'integration |
| T1411_cbh2t_end_f | CCAATAGCCCGGTGATAGTC (SEQ ID NO: 28) | |
| T415_77579_3screen | ACGCCGTTGCTGAGCCTTG (SEQ ID NO: 29) | 3'integration |
| T1404_cbh2term_for | CCGTCTAGCGCTGTTGATTG (SEQ ID NO: 30) | |
| C009_Ibat_for1 | GATCAACTTAGCACGCATTG (SEQ ID NO: 31) | internal |
| C029_PKIp_rev | TTTGCTCCAACTCAGGCG (SEQ ID NO: 32) | |

Figure 17:
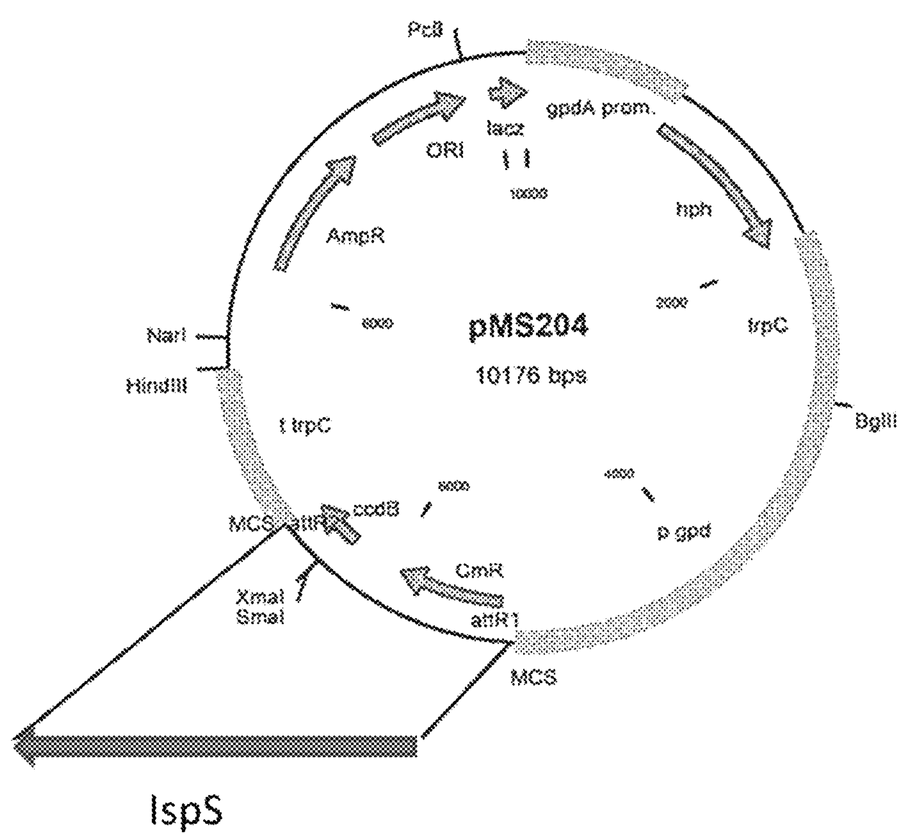
FIG. 17 shows plasmid for expression of IspS in filamentous fungi.

Example 13: Construction of *Aspergillus Niger* Strains Overexpressing an Isoprene Synthase for Isoprene Production The codon optimized isoprene synthase polynucleotide of example 3 was cloned into an expression vector containing the *A. nidulans* gpdA promoter—isoprene synthase polynucleotide—*A. nidulans* trpC terminator—*A. nidulans* gpdA promoter hygromycin resistance marker (hph) and *A. nidulans* trpC terminator (FIG. 17). The resulting construct was transformed into *A. niger*. Transformation was performed using the PEG-mediated protoplast transformation. The transformants were selected based on hygromycin resistance. The presence of the transforming DNA was confirmed by PCR.

*A. niger* was grown in the production medium (The defined medium of Vogel described by Mojzita et al., 2010, with 20 g/L glucose or xylose as a carbon source). Precultures were grown in the medium containing 10 g/L yeast extract, 20 g/L peptone and 30 g/L gelatine (50 ml medium in 250 ml flasks). Mycelium from 50 ml cultures was collected by filtration, washed with sterile $H_2O$ and re-suspended in 20 ml of the production medium in 250 ml flasks. Cultures were incubated at 30° C., 250 rpm. The culture medium was sampled periodically and the samples were transferred into GC-MS vials, heated at 40° C., and isoprene was measured off-line from the head space of the bottle using the GC-MS method described earlier for *E. coli*. Alternatively, for isoprene production, aliquots of the culture were transferred into fresh medium in tightly sealed GC-MS bottles. The bottles were incubated at 30° C. with 250 rpm shaking for up to 96 h. Samples were taken at regular intervals during the cultivation. At each time point a bottle was removed, the cultivation was heated at 40° C. and isoprene was measured from the head space of the bottle using the GC-MS method described earlier for *E. coli.*

Example 14: *Ipomoea Batatas* IspS Expression in Plant Cell Cultures

The *I. batatas* isoprene synthase polynucleotide was cloned into an over expression vector functional in various plant species under the control of the CaMV35S promoter for expression in plant cells. The expression vector had the hygromycin or kanamycin resistance marker for the selection of transformants. *Nicotiana tabacum* bright yellow (BY-2) cell suspension cultures or hairy root cultures were maintained and transformed with the isoprene synthase expression construct essentially as described in (Häkkinen et al. 2007 Phytochemistry 68:2773-2785). Transformants were selected based on antibiotic resistance. The presence of the transforming DNA was confirmed by PCR. For isoprene accumulation analysis, hairy roots were incubated in 20 ml medium in 100 ml shake flasks and cultivated in a rotary shaker (70 rpm, 24° C.) in modified Gamborg B5 medium without casein (Jouhikainen et al., Planta, 208:545-551, 1999) for up to 28 days. The culture medium was sampled periodically and the samples were transferred into GC-MS vials, heated at 40° C., and isoprene was measured off-line from the head space of the bottle using the GC-MS method described earlier for *E. coli*.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

What is claimed is:

1. A recombinant cell comprising an isoprene synthase enzyme having 95% or more sequence identity to SEQ ID NO: 1, wherein the recombinant cell is a cyanobacteria, yeast, or filamentous fungi.

2. The recombinant cell of claim 1, wherein the isoprene synthase enzyme has 98% or more sequence identity to SEQ ID NO: 1.

3. The recombinant cell of claim 1, wherein the isoprene synthase enzyme has 99% or more sequence identity to SEQ ID NO: 1.

* * * * *

SEQUENCE LISTING

```
<160> NUMBER OF SEQ ID NOS: 96

<210> SEQ ID NO 1
<211> LENGTH: 588
<212> TYPE: PRT
<213> ORGANISM: Ipomoea batatas

<400> SEQUENCE: 1

Pro Asn Phe Gly Cys Tyr Leu Ile His Asn Asn Leu Pro Asn Pro Lys
1               5                   10                  15

Asp Ala Lys Pro Leu Thr Leu Leu Leu Asn Arg Asn Ser Gly Val Ser
            20                  25                  30

Cys Pro Arg Gln Leu Arg Cys Leu Ala Ser Ser Ala Gln Asn Gln Glu
        35                  40                  45

Thr Ala Arg Arg Ser Ala Asn Tyr Gln Pro Ser Ser Trp Ser Tyr Asp
    50                  55                  60

Glu Tyr Leu Val Asp Thr Thr Thr Asn Asp Ser Lys Leu Arg Ile Gln
65                  70                  75                  80

Glu Asp Ala Arg Lys Lys Leu Glu Glu Glu Val Arg Asn Val Leu Glu
                85                  90                  95

Asp Gly Lys Leu Glu Thr Leu Ala Leu Leu Glu Leu Ile Asp Asp Ile
            100                 105                 110

Gln Arg Leu Gly Leu Gly Tyr Lys Phe Arg Glu Ser Thr Ser Thr Ser
        115                 120                 125

Leu Ala Met Leu Lys Met Ser Val Gly Gln Glu Ala Ser Asn Ser Ser
    130                 135                 140

Leu His Ser Cys Ser Leu Tyr Phe Arg Leu Leu Arg Glu His Gly Phe
145                 150                 155                 160

Asp Ile Thr Pro Asp Val Phe Glu Lys Phe Lys Asp Glu Asn Gly Lys
                165                 170                 175

Phe Lys Asp Ser Ile Ala Lys Asp Val Arg Gly Leu Leu Ser Leu Tyr
            180                 185                 190

Glu Ala Ser Phe Leu Gly Phe Glu Gly Glu Asn Ile Leu Asp Glu Ala
        195                 200                 205

Arg Glu Phe Thr Thr Met His Leu Asn Asn Ile Lys Asp Lys Val Asn
    210                 215                 220

Pro Arg Ile Ala Glu Glu Val Asn His Ala Leu Glu Leu Pro Leu His
225                 230                 235                 240

Arg Arg Val Glu Arg Leu Glu Ala Arg Arg Arg Ile Gln Ser Tyr Ser
                245                 250                 255

Lys Ser Gly Glu Thr Asn Gln Ala Leu Leu Thr Leu Ala Lys Ile Asp
            260                 265                 270

Phe Asn Thr Val Gln Ala Val Tyr Gln Arg Asp Leu Gln Asp Val Ser
        275                 280                 285

Lys Trp Trp Lys Asp Thr Ala Leu Ala Asp Lys Leu Ser Phe Ala Arg
    290                 295                 300
```

```
Asp Arg Leu Met Glu Ser Phe Phe Trp Ala Ile Gly Met Ser Tyr Asp
305                 310                 315                 320

Pro Gln His Ser Lys Ser Arg Glu Ala Val Thr Lys Thr Phe Lys Leu
                325                 330                 335

Val Thr Val Leu Asp Asp Val Tyr Asp Val Tyr Gly Ser Leu Asp Glu
            340                 345                 350

Leu Glu Lys Phe Thr Ala Ala Ala Glu Arg Trp Asp Val Asp Ala Ile
        355                 360                 365

Lys Asp Leu Pro Asp Tyr Met Lys Leu Cys Tyr Leu Ser Leu Phe Asn
    370                 375                 380

Thr Val Asn Asp Leu Ala Tyr Asp Thr Leu Lys Asp Lys Gly Glu Thr
385                 390                 395                 400

Val Ile Pro Ile Met Lys Lys Ala Trp Ala Asp Leu Leu Lys Ala Phe
                405                 410                 415

Leu Gln Glu Ala Gln Trp Ile Tyr Asn Lys Tyr Thr Pro Thr Phe Asp
            420                 425                 430

Glu Tyr Leu Asn Asn Ala Arg Phe Ser Val Ser Gly Cys Val Met Leu
        435                 440                 445

Val His Ser Tyr Phe Thr Thr Gln Asn Ile Thr Lys Glu Ala Ile His
    450                 455                 460

Ser Leu Glu Asn Tyr His Asp Leu Leu Ile Trp Pro Ser Ile Val Phe
465                 470                 475                 480

Arg Leu Ala Asn Asp Leu Ser Ser Ser Lys Ala Glu Ile Glu Arg Gly
                485                 490                 495

Glu Thr Ala Asn Ser Ile Thr Cys Tyr Met Asn Glu Thr Gly Gln Ser
            500                 505                 510

Glu Glu Gln Ala Arg Glu His Ile Ser Lys Leu Ile Asp Glu Cys Phe
        515                 520                 525

Lys Lys Met Asn Lys Glu Met Leu Ala Thr Ser Thr Ser Pro Phe Glu
    530                 535                 540

Lys Ser Phe Ile Glu Thr Ala Ile Asn Leu Ala Arg Ile Ala Leu Cys
545                 550                 555                 560

Gln Tyr Gln Tyr Gly Asp Ala His Ser Asp Pro Asp Val Arg Ala Arg
                565                 570                 575

Asn Arg Ile Val Ser Val Ile Ile Asn Pro Val Glu
            580                 585


<210> SEQ ID NO 2
<211> LENGTH: 1767
<212> TYPE: DNA
<213> ORGANISM: Ipomoea batatas

<400> SEQUENCE: 2

ccaaacttcg gttgctactt aattcacaac aatctcccta accctaaaga tgctaagcca      60

ctaacattac tccttaaccg taacagtggt gttagctgcc cacgacaact tcgatgtctt     120

gctagcagtg cacagaatca agaaactgcc agacgttccg ccaattacca acctagttct     180

tggagttacg atgaatattt ggtggacact acaaccaatg actcaaagtt gagaatacaa     240

gaggatgcta gaaagaagtt ggaggaagaa gtgagaaacg tccttgagga tgggaaattg     300

gaaacgttag ccttgcttga gctaattgac gatattcaac gtttagggtt gggttacaaa     360

ttcagagaaa gtactagtac atcccttgct atgctaaaga tgtctgttgg acaagaagcc     420

tcaaactcta gcctccattc ttgttctctc tattttagat tattaagaga gcatggcttt     480
```

```
gacattactc cagatgtttt tgaaaaattc aaggatgaaa atgggaaatt caaggacagc    540

atagctaaag acgttcgtgg gttgttgagt ttgtacgagg cttcctttct gggatttgaa    600

ggggagaaca tcttagacga ggcaagagaa ttcacaacta tgcatctaaa caacattaag    660

gataaggtta atccaagaat tgcagaagaa gtgaaccacg cattggagct tccacttcac    720

cgaagagtgg agaggctaga ggccaggcgt agaatccaat cctactccaa atcgggagag    780

acaaatcaag cgttattaac actagcaaag atcgatttca acactgttca agccgtgtat    840

caaagagatc tacaagatgt ttcaaagtgg tggaaagata ccgcgttagc agataagttg    900

agctttgcta gggacaggct aatggagagc ttcttttggg caattggaat gtcttatgat    960

cctcaacata gtaaaagtcg agaagcggtg acaaaaacat tcaagcttgt cacggtcctt   1020

gatgatgttt acgatgtgta tggctctctc gatgaacttg agaaattcac tgctgctgct   1080

gaaagatggg atgttgatgc aataaaagac cttccagact acatgaagtt gtgctatctt   1140

tctcttttca acactgtcaa cgacttagca tatgatacct taaaggacaa aggagaaact   1200

gtcattccta tcatgaagaa agcgtgggca gatttattga aagcattctt gcaagaagca   1260

caatggatct acaacaaata cactcctacc tttgatgaat acctcaacaa tgcacgtttt   1320

tctgtgtctg gttgtgtcat gttagttcac tcctacttca ccactcagaa catcacaaag   1380

gaagcaattc attccttgga gaactaccat gatcttttaa tctggccgtc catagttttc   1440

cgccttgcta acgatttgag ctcttctaag gcggagatag agagaggaga aacagcaaac   1500

tcgattacat gctatatgaa tgagactgga cagtcggagg agcaagctcg ggaacacatt   1560

agtaaactaa ttgacgagtg ctttaagaag atgaacaaag agatgctagc tacttcaact   1620

tcaccatttg agaaatcctt catagagact gcaataaatc ttgctcgaat tgctctgtgc   1680

caatatcagt atggtgacgc tcacagtgac cctgatgtta gagcaagaaa tcggatcgtg   1740

tcagttatca taaatccggt tgaataa                                          1767
```

<210> SEQ ID NO 3
<211> LENGTH: 1626
<212> TYPE: DNA
<213> ORGANISM: Artificial
<220> FEATURE:
<223> OTHER INFORMATION: optimized sequence of IspS

<400> SEQUENCE: 3

```
atgactgccc gccgctcagc aaactatcaa ccctcctcat ggtcttacga cgaatacttg     60

gtggacacta ctactaacga cagcaaactg cgcattcaag aagacgctcg taaaaaattg    120

gaagaagaag tgcgtaacgt tctggaagat ggcaaattgg aaaccttagc actgttggaa    180

ctgattgatg acatccaacg gctgggcttg ggttataaat ttcgcgaaag caccagtact    240

tccctggcta tgttgaaaat gagtgtgggg caggaagcat ccaacagcag tttgcattct    300

tgttcattgt actttcgttt actgcgggaa cacggcttcg atattacccc cgacgtgttc    360

gaaaaattca aagatgaaaa cggtaaattt aaagatagca tcgctaaaga tgttcgcggg    420

ttgttatcat tgtatgaagc aagcttttta gggttcgaag gcgaaaacat tttggacgaa    480

gcccgcgaat tcaccactat gcatctgaat aacatcaaag ataaagtgaa tccccgtatc    540

gcggaagaag ttaaccatgc tttagaactg ccgttgcacc gccgtgtgga acgtctggaa    600

gctcggcgcc gtattcaaag ctatagtaaa tccggtgaaa ccaatcaggc cctgctgacc    660

ctggctaaaa tcgattttaa caccgtgcag gcggtttacc aacgggatct gcaggacgtt    720

agtaaatggt ggaaagacac tgcattggcc gataaattat ccttcgcccg ggatcgcctg    780
```

```
atggaaagct ttttctgggc gattggtatg agctatgatc cccaacactc taaatcacgg    840

gaagccgtga ccaaaacttt taaactggtg accgttttgg atgacgtgta tgacgtttac    900

gggtctttag atgaactgga aaaattcacc gccgccgccg aacgttggga tgttgacgcg    960

attaaagatc tgccggacta catgaaattg tgttacttat ccctgtttaa taccgtgaac   1020

gatctggctt atgacacctt gaaagataaa ggcgaaactg ttattcctat catgaagaaa   1080

gcctgggctg atttactgaa agcatttctg caggaagccc aatggatcta caacaaatac   1140

accccaactt tcgatgaata cctgaataac gcccgtttca gcgtgagtgg ttgcgtgatg   1200

ttggttcata gctactttac cactcagaac atcaccaaag aagcgatcca ttctctggaa   1260

aactaccacg acttgttaat ttggcctagc atcgttttcc gtttagcaaa tgatctgtcc   1320

tcttcaaaag ccgaaattga acggggcgaa accgcgaata gcatcacttg ttatatgaac   1380

gaaaccggtc aaagtgaaga acaggcccgt gaacacattt ccaaactgat cgatgaatgc   1440

ttcaagaaaa tgaacaaaga aatgctggcc acctccactt ctccgtttga aaaatccttc   1500

attgaaaccg cgatcaactt agcacgcatt gccctgtgcc agtatcaata cggcgatgcc   1560

catagcgatc cagatgttcg ggcacgcaac cgcattgtgt cagttatcat taatccagtg   1620

gaatag                                                              1626
```

<210> SEQ ID NO 4
<211> LENGTH: 62
<212> TYPE: DNA
<213> ORGANISM: Artificial
<220> FEATURE:
<223> OTHER INFORMATION: primer

<400> SEQUENCE: 4

```
tagcaatcta atctaagttt taattacaaa ctcgagtaaa atggaccaat tggtgaaaac     60

tg                                                                    62
```

<210> SEQ ID NO 5
<211> LENGTH: 53
<212> TYPE: DNA
<213> ORGANISM: Artificial
<220> FEATURE:
<223> OTHER INFORMATION: primer

<400> SEQUENCE: 5

```
ccaaacctct ggcgaagaag tccaaagctg tcgacggatt taatgcaggt gac            53
```

<210> SEQ ID NO 6
<211> LENGTH: 9167
<212> TYPE: DNA
<213> ORGANISM: Artificial
<220> FEATURE:
<223> OTHER INFORMATION: expression vector for an N-terminally truncated
      S. cerevisiae HMG1 named pPK-HMG
<220> FEATURE:
<221> NAME/KEY: misc_feature
<222> LOCATION: (1189)..(1189)
<223> OTHER INFORMATION: n is a, c, g, or t
<220> FEATURE:
<221> NAME/KEY: misc_feature
<222> LOCATION: (6696)..(6696)
<223> OTHER INFORMATION: n is a, c, g, or t

<400> SEQUENCE: 6

```
ggccgcaata gagagtgacc tatccaagct ttgggggtct aagttttaat ggcccaggga     60

atcattactt ttttttctca atccttgatg gataaaagta ttacatacgt acaggattgt    120
```

```
gtattagtgt atttcgttat atgattaaac aaagtttata gattgtaaag tagacgtaaa    180
gtttagtaat tcattttaat gttcatttta cattcagatg tcattaagcg gctttagagt    240
tgatttcatc agataattta gcttgagcaa ccaagatttc tggagcatcg aattcatcca    300
agaataattc aatgactcta atcttatctt ccttgttgaa tgcttcatcc ttcatcaaag    360
cgtccaagtc cttagcggat ttaacaacat ggttttcata ttgggtcttg tcagcaaaga    420
gcttcaataa caattggtga tcccatggtt gaatttggtt gtagtcctca tgacgaccgt    480
ggatcaactt ttcgatagtg taacctctgt tgtttaagat gaagatgtat ggcttgatgt    540
tccatcttgc agcatctgag attgattgga cagtcaattg taaagaacca tcaccaataa    600
acaaaacagt tcttctttct tgttcgccag tttgtttgtg tgcatcttca gcagcaaatg    660
cagcaccaac tgcagctggt aaggagaaac caatggaacc ccataagact tgggagatag    720
actttgaatc tcttggtatg ggtagccaag actagtcgat atcacctaat aacttcgtat    780
agcatacatt atacgaagtt atattaaggg ttctcgagaa ttcttgctgc aacggcaaca    840
tcaatgtcca cgtttacaca cctacattta tatctatatt tatatttata tttatttatt    900
tatgctactt agcttctata gttagttaat gcactcacga tattcaaaat tgacaccctt    960
caactactcc ctactattgt ctactactgt ctactactcc tctttactat agctgctccc   1020
aataggctcc accaataggc tctgtcaata cattttgcgc cgccaccttt caggttgtgt   1080
cactcctgaa ggaccatatt gggtaatcgt gcaatttctg gaagagagtg ccgcgagaag   1140
tgaggccccc actgtaaatc ctcgaggggg catggagtat ggggcatgna ggatggagga   1200
tggggggggg gggggaaaat aggtagcgaa aggacccgct atcaccccac ccggagaact   1260
cgttgccggg aagtcatatt tcgacactcc ggggagtcta taaaaggcgg gttttgtctt   1320
ttgccagttg atgttgctga gaggacttgt ttgccgtttc ttccgattta acagtataga   1380
atcaaccact gttaattata cacgttatac taacacaaca aaaacaaaaa caacgacaac   1440
aacaacaaca atgtttgctt tctactttct caccgcatgc accactttga agggtgtttt   1500
cggagtttct ccgagttaca atggtcttgg tctcacccca cagatgggtt gggacagctg   1560
gaatacgttt gcctgcgatg tcagtgaaca gctacttcta gacactgctg atagaatttc   1620
tgacttgggg ctaaaggata tgggttacaa gtatgtcatc ctagatgact gttggtctag   1680
cggcagggat tccgacggtt tcctcgttgc agacaagcac aaatttccca acggtatggg   1740
ccatgttgca gaccacctgc ataataacag ctttcttttc ggtatgtatt cgtctgctgg   1800
tgagtacacc tgtgctgggt accctgggtc tctggggcgt gaggaagaag atgctcaatt   1860
ctttgcaaat aaccgcgttg actacttgaa gtatgataat tgttacaata aaggtcaatt   1920
tggtacacca gacgtttctt accaccgtta caaggccatg tcagatgctt tgaataaaac   1980
tggtaggcct attttctatt ctctatgtaa ctggggtcag gatttgacat tttactgggg   2040
ctctggtatc gccaattctt ggagaatgag cggagatatt actgctgagt tcacccgtcc   2100
agatagcaga tgtccctgtg acggtgacga atatgattgc aagtacgccg gtttccattg   2160
ttctattatg aatattctta acaaggcagc tccaatgggg caaaatgcag gtgttggtgg   2220
ttggaacgat ctggacaatc tagaggtcgg agtcggtaat ttgactgacg atgaggaaaa   2280
ggcccatttc tctatgtggg caatggtaaa gtccccactt atcattggtg ccgacgtgaa   2340
tcacttaaag gcatcttcgt actcgatcta cagtcaagcc tctgtcatcg caattaatca   2400
agatccaaag ggtattccag ccacaagagt ctggagatat tatgtttcag acaccgatga   2460
```

-continued

```
atatggacaa ggtgaaattc aaatgtggag tggtccgctt gacaatggtg accaagtggt   2520
tgctttattg aatggaggaa gcgtagcaag accaatgaac acgaccttgg aagagatttt   2580
ctttgacagc aatttgggtt caaaggaact gacatcgact tgggatattt acgacttatg   2640
ggccaacaga gttgacaact ctacggcgtc tgctatcctt gaacagaata aggcagccac   2700
cggtattctc tacaatgcta cagagcagtc ttataaagac ggtttgtcta agaatgatac   2760
aagactgttt ggccagaaaa ttggtagtct ttctccaaat gctatactta acacaactgt   2820
tccagctcat ggtatcgcct tctataggtt gagaccctcg gcttaagctc aatgttgagc   2880
aaagcaggac gagaaaaaaa aaaataatga ttgttaagaa gttcatgaaa aaaaaaagga   2940
aaaatactca aatacttata acagagtgat taaataataa acggcagtat accctatcag   3000
gtattgagat agttttattt ttgtaggtat ataatctgaa gcctttgaac tattttctcg   3060
tatatatcat ggagtataca ttgcattagc aacattacat actaggatct ctagacctaa   3120
taacttcgta tagcatacat tatacgaagt tatattaagg gttgtcgacg gatccttgct   3180
gcaacggcaa catcaatgtc cacgtttaca cacctacatt tatatctata tttatattta   3240
tatttattta tttatgctac ttagcttcta tagttagtta atgcactcac gatattcaaa   3300
attgacaccc ttcaactact ccctactatt gtctactact gtctactact cctctttact   3360
atagctgctc ccaataggct ccaccaatag gctctgccaa tacattttgc gccgccacct   3420
ttcaggttgt gtcactcctg aaggaccata ttgggtaatc gtgcaatttc tggaagagag   3480
tccgcgagaa gtgaggcccc cactgtaaat cctcgagggg gcatggagta tggggcatgg   3540
aggatggagg atgggggggg gcgaaaaata ggtagcgaaa ggacccgcta tcaccccacc   3600
cggagaactc gttgccggga agtcatattt cgacactccg gggagtctat aaaaggcggg   3660
ttttgtcttt tgccagttga tgttgctgag aggacttgtt tgccgtttct tccgatttaa   3720
cagtatagaa tcaaccactg ttaattatac acgttatact aacacaacaa aaacaaaaac   3780
aacgacaaca acaacaacaa gatccatgga ccaattggtg aaaactgaag tcaccaagaa   3840
gtcttttact gctcctgtac aaaaggcttc tacaccagtt ttaaccaata aaacagtcat   3900
ttctggatcg aaagtcaaaa gtttatcatc tgcgcaatcg agctcatcag gaccttcatc   3960
atctagtgag gaagatgatt cccgcgatat tgaaagcttg gataagaaaa tacgtccttt   4020
agaagaatta gaagcattat taagtagtgg aaatacaaaa caattgaaga acaaagaggt   4080
cgctgccttg gttattcacg gtaagttacc tttgtacgct ttggagaaaa aattaggtga   4140
tactacgaga gcggttgcgg tacgtaggaa ggctctttca attttggcag aagctcctgt   4200
attagcatct gatcgtttac catataaaaa ttatgactac gaccgcgtat ttggcgcttg   4260
ttgtgaaaat gttataggtt acatgccttt gcccgttggt gttataggcc ccttggttat   4320
cgatggtaca tcttatcata taccaatggc aactacagag ggttgtttgg tagcttctgc   4380
catgcgtggc tgtaaggcaa tcaatgctgg cggtggtgca acaactgttt taactaagga   4440
tggtatgaca agaggcccag tagtccgttt cccaactttg aaaagatctg gtgcctgtaa   4500
gatatggtta gactcagaag agggacaaaa cgcaattaaa aaagctttta actctacatc   4560
aagatttgca cgtctgcaac atattcaaac ttgtctagca ggagatttac tcttcatgag   4620
atttagaaca actactggtg acgcaatggg tatgaatatg atttctaaag gtgtcgaata   4680
ctcattaaag caaatggtag aagagtatgg ctgggaagat atggaggttg tctccgtttc   4740
tggtaactac tgtaccgaca aaaaaccagc tgccatcaac tggatcgaag gtcgtggtaa   4800
gagtgtcgtc gcagaagcta ctattcctgg tgatgttgtc agaaaagtgt taaaaagtga   4860
```

```
tgtttccgca ttggttgagt tgaacattgc taagaatttg gttggatctg caatggctgg   4920
gtctgttggt ggatttaacg cacatgcagc taatttagtg acagctgttt tcttggcatt   4980
aggacaagat cctgcacaaa atgttgaaag ttccaactgt ataacattga tgaaagaagt   5040
ggacggtgat ttgagaattt ccgtatccat gccatccatc gaagtaggta ccatcggtgg   5100
tggtactgtt ctagaaccac aaggtgccat gttggactta ttaggtgtaa gaggcccgca   5160
tgctaccgct cctggtacca acgcacgtca attagcaaga atagttgcct gtgccgtctt   5220
ggcaggtgaa ttatccttat gtgctgccct agcagccggc catttggttc aaagtcatat   5280
gacccacaac aggaaacctg ctgaaccaac aaaacctaac aatttggacg ccactgatat   5340
aaatcgtttg aaagatgggt ccgtcacctg cattaaatcc taaacttagt catacgtcat   5400
tggtattctc ttgaaaaaga agcacaacag caccatgtgg gatcttccaa gctttggact   5460
tcttcgccag aggtttggtc aagtctccaa tcaaggttgt cggcttgtct accttgccag   5520
aaatttacga aaagatggaa aagggtcaaa tcgttggtag atacgttgtt gacacttcta   5580
aataagcgaa tttcttatga tttatgattt ttattattaa ataagttata aaaaaaataa   5640
gtgtatacaa attttaaagt gactcttagg ttttaaaacg aaaattctta ttcttgagta   5700
actctttcct gtaggtcagg ttgctttctc aggtatagca tgaggtcgct cttattgacc   5760
acacctctac cggcatgccg agcaaatgcc tgcaaatcgc tccccatttc acccaattgt   5820
agatatgcta actccagcaa tgagttgatg aatctcggtg tgtattttat gtcctcagag   5880
gacaacacct gttgtaatcg ttcttccaca cggatccgta tcatttgtag cccacgccac   5940
ccggaaaaac caccattgtc ctcagcagtc cgccaaaata tggatgcgct caatcaactt   6000
tccctccccc gtcaatgcca aaaggataac gacacactat taagagcgca tcatttgtaa   6060
aagccgagga agggggatac gctaaccgga gacgtctcgc ctcactctcg gagctgagcc   6120
gccctcctta agaaattcat gggaagaaca cccttcgcgg cttctgaacg gctcgccctc   6180
gtccattggt cacctcacag tggcaactaa taaggacatt atagcaatag aaattaaaat   6240
ggtgcacaga aatacaatag gatcgaatag gataggatac aataagatac ggaatattag   6300
actatactgt gatacggtac ggtacgatac gctacgatac gatacgatag aggataccac   6360
ggatataacg tagtattatt tttcattatt gggggttttt ttctgtttga attttccacg   6420
tcaagagtat cccatctgac aggaaccgat ggactcgtca cagtacctat cgcccgagtt   6480
caatccatgg acgcttcggg tgaaggatct tcgtccgctg ttggcaagcc atgggatcag   6540
ggcgtcgcca agggacagaa aggcggatct tgtacgtctc ttcaacacag agctgcgtcc   6600
gaaacttact gagagtctta acaccaataa tcccaaaaac aacaacaaca atacagatac   6660
tatagacact atagacacta tagacactac taacanccct ttaaagcgcc gccgattaag   6720
caatgttgat gagccgtcaa ttccatatac tctgcagcgt acgaagcttc agctggcggc   6780
cgcgttctat agtgtcacct aaatcgtatg tgtatgatac ataaggttat gtattaattg   6840
tagccgcgtt ctaacgacaa tatgtccata tggtgcactc tcagtacaat ctgctctgat   6900
gccgcatagt taagccagcc ccgacacccg ccaacacccg ctgacgcgcc ctgacgggct   6960
tgtctgctcc cggcatccgc ttacagacaa gctgtgaccg tctccgggag ctgcatgtgt   7020
cagaggtttt caccgtcatc accgaaacgc gcgagacgaa agggcctcgt gatacgccta   7080
tttttatagg ttaatgtcat gataataatg gtttcttaga cgtcaggtgg cacttttcgg   7140
ggaaatgtgc gcggaacccc tatttgttta tttttctaaa tacattcaaa tatgtatccg   7200
```

```
ctcatgagac aataaccctg ataaatgctt caataatatt gaaaaaggaa gagtatgagt   7260

attcaacatt tccgtgtcgc ccttattccc ttttttgcgg cattttgcct tcctgttttt   7320

gctcacccag aaacgctggt gaaagtaaaa gatgctgaag atcagttggg tgcacgagtg   7380

ggttacatcg aactggatct caacagcggt aagatccttg agagttttcg ccccgaagaa   7440

cgttttccaa tgatgagcac ttttaaagtt ctgctatgtg gcgcggtatt atcccgtatt   7500

gacgccgggc aagagcaact cggtcgccgc atacactatt ctcagaatga cttggttgag   7560

tactcaccag tcacagaaaa gcatcttacg gatggcatga cagtaagaga attatgcagt   7620

gctgccataa ccatgagtga taacactgcg gccaacttac ttctgacaac gatcggagga   7680

ccgaaggagc taaccgcttt tttgcacaac atgggggatc atgtaactcg ccttgatcgt   7740

tgggaaccgg agctgaatga agccatacca aacgacgagc gtgacaccac gatgcctgta   7800

gcaatggcaa caacgttgcg caaactatta actggcgaac tacttactct agcttcccgg   7860

caacaattaa tagactggat ggaggcggat aaagttgcag gaccacttct gcgctcggcc   7920

cttccggctg gctggtttat tgctgataaa tctggagccg gtgagcgtgg gtctcgcggt   7980

atcattgcag cactggggcc agatggtaag ccctcccgta tcgtagttat ctacacgacg   8040

gggagtcagg caactatgga tgaacgaaat agacagatcg ctgagatagg tgcctcactg   8100

attaagcatt ggtaactgtc agaccaagtt tactcatata tactttagat tgatttaaaa   8160

cttcattttt aatttaaaag gatctaggtg aagatccttt ttgataatct catgaccaaa   8220

atcccttaac gtgagttttc gttccactga gcgtcagacc ccgtagaaaa gatcaaagga   8280

tcttcttgag atcctttttt tctgcgcgta atctgctgct tgcaaacaaa aaaaccaccg   8340

ctaccagcgg tggtttgttt gccggatcaa gagctaccaa ctctttttcc gaaggtaact   8400

ggcttcagca gagcgcagat accaaatact gtccttctag tgtagccgta gttaggccac   8460

cacttcaaga actctgtagc accgcctaca tacctcgctc tgctaatcct gttaccagtg   8520

gctgctgcca gtggcgataa gtcgtgtctt accgggttgg actcaagacg atagttaccg   8580

gataaggcgc agcggtcggg ctgaacgggg ggttcgtgca cacagcccag cttggagcga   8640

acgacctaca ccgaactgag atacctacag cgtgagcatt gagaaagcgc cacgcttccc   8700

gaagggagaa aggcggacag gtatccggta agcggcaggg tcggaacagg agagcgcacg   8760

agggagcttc cagggggaaa cgcctggtat ctttatagtc ctgtcgggtt tcgccacctc   8820

tgacttgagc gtcgattttt gtgatgctcg tcaggggggc ggagcctatg gaaaaacgcc   8880

agcaacgcgg cctttttacg gttcctggcc ttttgctggc cttttgctca catgttcttt   8940

cctgcgttat cccctgattc tgtggataac cgtattaccg cctttgagtg agctgatacc   9000

gctcgccgca gccgaacgac cgagcgcagc gagtcagtga gcgaggaagc ggaagagcgc   9060

ccaatacgca aaccgcctct ccccgcgcgt tggccgattc attaatgcag gttaacctgg   9120

cttatcgaaa ttaatacgac tcactatagg gagaccggca gatccgc                9167
```

```
<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7

agcgcggatc catggaccaa ttggtgaaaa ctgaag                              36
```

<210> SEQ ID NO 8
<211> LENGTH: 32
<212> TYPE: DNA
<213> ORGANISM: Artificial
<220> FEATURE:
<223> OTHER INFORMATION: primer

<400> SEQUENCE: 8

```
agcgcggatc ccacatggtg ctgttgtgct tc                                 32
```

<210> SEQ ID NO 9
<211> LENGTH: 9935
<212> TYPE: DNA
<213> ORGANISM: Artificial
<220> FEATURE:
<223> OTHER INFORMATION: vector for expression of I. batatas IspS and S. cerevisiae IDI1 was named pPK-IspS-IDI
<220> FEATURE:
<221> NAME/KEY: misc_feature
<222> LOCATION: (957)..(957)
<223> OTHER INFORMATION: n is a, c, g, or t

<400> SEQUENCE: 9

```
ggccgcatag gccactagtt caaagggaat gtgataatgc aaggttaggt ttaacaagaa     60

tgggttggcg gactcgtcaa tggagagtac aatgccaaag ttctccttga ggttatttaa    120

tcttccacag gttcaaggca ttctggcagc ttctcaattg ggaagttttc gtagatgata    180

cggtaggtgg tggtaaatag tgggaactca tctgtcctgc ccatgttgga gaggaactcg    240

taaacttccc tagttgtgtg gataccttga caggattggc cattcaacaa cttttcttca    300

gcctccgttg cagagacaga atgttgtgcc atatatctac caactctaac gttacggccg    360

ccggcacagg tagtgattag gtcggcaaca cctgcagatt catgagtaaa ggttgcagca    420

tgacagccat cgaaaaaagt cttggcaaat tgaatggttt ccaccaaacc tattctcatg    480

actgcagcct ttgcattatc accccaacct aaaccttcga caaatgatat cacctaataa    540

cttcgtatag catacattat acgaagttat attaagggtt ctcgagaatt cttgctgcaa    600

cggcaacatc aatgtccacg tttacacacc tacatttata tctatattta tatttatatt    660

tatttattta tgctacttag cttctatagt tagttaatgc actcacgata ttcaaaattg    720

acacccttca actactccct actattgtct actactgtct actactcctc tttactatag    780

ctgctcccaa taggctccac caataggctc tgtcaataca ttttgcgccg ccacctttca    840

ggttgtgtca ctcctgaagg accatattgg gtaatcgtgc aatttctgga agagagtgcc    900

gcgagaagtg aggcccccac tgtaaatcct cgagggggca tggagtatgg ggcatgnagg    960

atggaggatg gggggggggg gggaaaatag gtagcgaaag gacccgctat caccccaccc   1020

ggagaactcg ttgccgggaa gtcatatttc gacactccgg ggagtctata aaaggcgggt   1080

tttgtctttt gccagttgat gttgctgaga ggacttgttt gccgtttctt ccgatttaac   1140

agtatagaat caaccactgt taattataca cgttatacta acacaacaaa aacaaaaaca   1200

acgacaacaa caacaacaat gcctgaactc accgcgacgt ctgtcgagaa gtttctgatc   1260

gaaaagttcg acagcgtctc cgacctgatg cagctctcgg agggcgaaga atctcgtgct   1320

ttcagcttcg atgtaggagg gcgtggatat gtcctgcggg taaatagctg cgccgatggt   1380

ttctacaaag atcgttatgt ttatcggcac tttgcatcgg ccgcgctccc gattccggaa   1440

gtgcttgaca ttggggaatt cagcgagagc ctgacctatt gcatctcccg ccgtgcacag   1500

ggtgtcacgt tgcaagacct gcctgaaacc gaactgcccg ctgttctgca gccggtcgcg   1560

gaggccatgg atgcgatcgc tgcggccgat cttagccaga cgagcgggtt cggcccattc   1620
```

```
ggaccgcaag gaatcggtca atacactaca tggcgtgatt tcatatgcgc gattgctgat   1680
ccccatgtgt atcactggca aactgtgatg gacgacaccg tcagtgcgtc cgtcgcgcag   1740
gctctcgatg agctgatgct ttgggccgag gactgccccg aagtccggca cctcgtgcac   1800
gcggatttcg gctccaacaa tgtcctgacg gacaatggcc gcataacagc ggtcattgac   1860
tggagcgagg cgatgttcgg ggattcccaa tacgaggtcg ccaacatctt cttctggagg   1920
ccgtggttgg cttgtatgga gcagcagacg cgctacttcg agcggaggca tccggagctt   1980
gcaggatcgc cgcggctccg ggcgtatatg ctccgcattg gtcttgacca actctatcag   2040
agcttggttg acggcaattt cgatgatgca gcttgggcgc agggtcgatg cgacgcaatc   2100
gtccgatccg gagccgggac tgtcgggcgt acacaaatcg cccgcagaag cgcggccgtc   2160
tggaccgatg gctgtgtaga agtactcgcc gatagtggaa accgacgccc cagcactcgt   2220
ccgagggcaa aggaatagag tagtaagctc aatgttgagc aaagcaggac gagaaaaaaa   2280
aaaataatga ttgttaagaa gttcatgaaa aaaaaaagga aaaatactca aatacttata   2340
acagagtgat taaataataa acggcagtat accctatcag gtattgagat agttttattt   2400
ttgtaggtat ataatctgaa gcctttgaac tatttttctcg tatatatcat ggagtataca   2460
ttgcattagc aacattacat actaggatct ctagacctaa taacttcgta tagcatacat   2520
tatacgaagt tatattaagg gttgtcgacg gatccttgct gcaacggcaa catcaatgtc   2580
cacgtttaca cacctacatt tatatctata tttatattta tatttattta tttatgctac   2640
ttagcttcta tagttagtta atgcactcac gatattcaaa attgacaccc ttcaactact   2700
ccctactatt gtctactact gtctactact cctctttact atagctgctc ccaataggct   2760
ccaccaatag gctctgccaa tacattttgc gccgccacct ttcaggttgt gtcactcctg   2820
aaggaccata ttgggtaatc gtgcaatttc tggaagagag tccgcgagaa gtgaggcccc   2880
cactgtaaat cctcgagggg gcatggagta tggggcatgg aggatggagg atgggggggg   2940
gcgaaaaata ggtagcgaaa ggacccgcta tcaccccacc cggagaactc gttgccggga   3000
agtcatattt cgacactccg gggagtctat aaaaggcggg ttttgtcttt tgccagttga   3060
tgttgctgag aggacttgtt tgccgtttct tccgatttaa cagtatagaa tcaaccactg   3120
ttaattatac acgttatact aacacaacaa aaacaaaaac aacgacaaca acaacaacaa   3180
gatccaaaat gacagccaga agatcagcaa actatcaacc ttcatcatgg tcctacgacg   3240
aatacttggt cgatacaaca acaaacgatt ctaaattaag aatacaagaa gacgcaagaa   3300
agaaattgga agaagaagta agaaacgttt tggaagatgg taaattagaa actttggcct   3360
tgttggaatt gatcgatgac attcaaagat tgggtttagg ttacaagttt agagaatcaa   3420
catccaccag tttagccatg ttgaagatgt cagttggtca agaagcatct aattcttctt   3480
tgcattcttg ttcattgtac tttagattgt tgagagaaca cggtttcgat ataacaccag   3540
acgtattcga aaaattcaag gatgaaaacg gtaaattcaa agattctatc gctaaggatg   3600
ttagaggttt gttaagttta tatgaagcat catttttggg tttcgaaggt gaaaacatat   3660
tggatgaagc tagagagttt actacaatgc acttgaataa catcaaggat aaggtcaacc   3720
caagaatagc agaagaagta aaccatgcct tggaattacc tttgcacaga agagttgaaa   3780
gattagaagc tagaagaaga atacaatcct acagtaagtc tggtgaaacc aatcaagcat   3840
tgttgacttt ggcaaagatc gatttcaaca ctgtccaagc agtataccaa agagatttgc   3900
aagacgtttc aaaatggtgg aaggacacag ctttagcaga taaattgtcc ttcgcaagag   3960
```

-continued

```
atagattgat ggaatctttc ttttgggcca tcggcatgtc ttacgatcca caacactcaa   4020
agtccagaga agctgtcact aagactttta aattggttac cgtcttggat gacgtttatg   4080
acgtctacgg ttctttagat gaattggaaa aattcactgc tgcagccgaa agatgggatg   4140
tagacgctat aaaagatttg cctgactaca tgaagttgtg ttacttatca ttgtttaata   4200
ctgttaacga tttggcatat gacacattga aagataaggg tgaaaccgtc attccaataa   4260
tgaaaaaggc ttgggctgat ttgttaaaag ccttcttaca agaagctcaa tggatctata   4320
ataagtacac ccctactttc gatgaatact taaataacgc tagattcagt gtttctggtt   4380
gcgtaatgtt ggttcattct tactttacca ctcaaaacat cacaaaggaa gcaatccata   4440
gtttggaaaa ctaccacgac ttgttaatat ggccttctat cgtcttcaga ttagctaatg   4500
atttgtccag ttctaaggca gaaatcgaaa gaggtgaaac tgccaattct atcacatgtt   4560
acatgaacga aacaggtcaa tcagaagaac aagctagaga acatatctcc aaattgatcg   4620
atgaatgctt caaaaagatg aataaggaaa tgttggccac atcaacctcc ccatttgaaa   4680
aatcattcat cgaaaccgct attaacttag caagaattgc cttgtgccaa tatcaatacg   4740
gtgacgctca ctctgatcct gacgttagag caagaaatag aatcgtaagt gtcatcatta   4800
atccagtcga atggtcacat ccacaatttg aaaagtaata gggatcttcc aagctttgga   4860
cttcttcgcc agaggtttgg tcaagtctcc aatcaaggtt gtcggcttgt ctaccttgcc   4920
agaaatttac gaaaagatgg aaaagggtca aatcgttggt agatacgttg ttgacacttc   4980
taaataagcg aatttcttat gatttatgat ttttattatt aaataagtta taaaaaaaat   5040
aagtgtatac aaattttaaa gtgactctta ggttttaaaa cgaaaattct tattcttgag   5100
taactctttc ctgtaggtca ggttgctttc tcaggtatag catgaggtcg ctcttattga   5160
ccacacctct accggcatgc gatatggata tggatatgga tatggagatg aatttgaatt   5220
tagatttggg tcttgatttg ggttggaat taaaagggga taacaatgag ggttttcctg   5280
ttgatttaaa caatggacgt gggaggtgat tgatttaacc tgatccaaaa ggggtatgtc   5340
tattttttag agagtgtttt tgtgtcaaat tatggtagaa tgtgtaaagt agtataaact   5400
ttcctctcaa atgacgaggt ttaaaacacc ccccgggtga gccgagccga gaatggggca   5460
attgttcaat gtgaaataga agtatcgagt gagaaacttg ggtgttggcc agccaagggg   5520
ggggggaag gaaaatggcg cgaatgctca ggtgagattg ttttggaatt gggtgaagcg   5580
aggaaatgag cgacccggag gttgtgactt tagtggcgga ggaggacgga ggaaaagcca   5640
agagggaagt gtatataagg ggagcaattt gccaccagga tagaattgga tgagttataa   5700
ttctactgta tttattgtat aatttatttc tccttttgta tcaaacacat tacaaaacac   5760
acaaaacaca caaacaaaca caattacaaa aattaattaa aaaatgactg ccgacaacaa   5820
tagtatgccc catggtgcag tatctagtta cgccaaatta gtgcaaaacc aaacacctga   5880
agacattttg gaagagtttc ctgaaattat tccattacaa caaagaccta atacccgatc   5940
tagtgagacg tcaaatgacg aaagcggaga aacatgtttt tctggtcatg atgaggagca   6000
aattaagtta atgaatgaaa attgtattgt tttggattgg gacgataatg ctattggtgc   6060
cggtaccaag aaagtttgtc atttaatgga aaatattgaa aagggtttac tacatcgtgc   6120
attctccgtc tttattttca atgaacaagg tgaattactt ttacaacaaa gagccactga   6180
aaaaataact ttccctgatc tttggactaa cacatgctgc tctcatccac tatgtattga   6240
tgacgaatta ggtttgaagg gtaagctaga cgataagatt aagggcgcta ttactgcggc   6300
ggtgagaaaa ctagatcatg aattaggtat tccagaagat gaaactaaga caaggggtaa   6360
```

-continued

```
gtttcacttt ttaaacagaa tccattacat ggcaccaagc aatgaaccat ggggtgaaca   6420
tgaaattgat tacatcctat tttataagat caacgctaaa gaaaacttga ctgtcaaccc   6480
aaacgtcaat gaagttagag acttcaaatg ggtttcacca aatgatttga aaactatgtt   6540
tgctgaccca agttacaagt ttacgccttg gtttaagatt atttgcgaga attacttatt   6600
caactggtgg gagcaattag atgacctttc tgaagtggaa aatgacaggc aaattcatag   6660
aatgctataa ttaattaacc catgtctcta ctggtggtgg tgcttctttg gaattattgg   6720
aaggtaagga attgccaggt gttgctttct tatccgaaaa gaaataaatt gaattgaatt   6780
gaaatcgata gatcaatttt tttcttttct ctttccccat cctttacgct aaaataatag   6840
tttattttat tttttgaata ttttttattt atatacgtat atatagacta ttatttatct   6900
tttaatgatt attaagattt ttattaaaaa aaaattcgct cctcttttaa tgcctttatg   6960
cagttttttt ttcccattcg atatttctat gttcgggttc agcgtatttt aagtttaata   7020
actcgaaaat tctgcgttcg ttaacctgca gggatccatt cttggtaaaa attggtgagg   7080
aatattaaag acaatcaagt ctgagcctgc acaagcctca acaatgtctg gaactgcaac   7140
aacgttaact ggcaacttga tacctggcaa gtacttgacg ttttcgtgtt tggtatttat   7200
gatttcagtc aacttttcgc cttcaatcaa ttcttcatag acccacatat taacatctct   7260
ttgaaattga cgaggtctct caacggtgtt ttccgctata accttggcaa ttgtacaccc   7320
ccagttaccg gaaccaacaa ccgtcacctt gaacggatgt tccggatagt cttctggttg   7380
taatgatgta gaatcttttc tgtttggctt gattgtggac gcaatagtag ataatctttc   7440
agcaggggac accattttaa tgtttgatct attcaatgtc ttgatagtat ttgagaaact   7500
ccttgtaaag tgtaaactct ttgagattag aaacatacag ctggcggccg cgttctatag   7560
tgtcacctaa atcgtatgtg tatgatacat aaggttatgt attaattgta gccgcgttct   7620
aacgacaata tgtccatatg gtgcactctc agtacaatct gctctgatgc cgcatagtta   7680
agccagcccc gacacccgcc aacacccgct gacgcgccct gacgggcttg tctgctcccg   7740
gcatccgctt acagacaagc tgtgaccgtc tccgggagct gcatgtgtca gaggttttca   7800
ccgtcatcac cgaaacgcgc gagacgaaag ggcctcgtga tacgcctatt tttataggtt   7860
aatgtcatga taataatggt ttcttagacg tcaggtggca cttttcgggg aaatgtgcgc   7920
ggaaccccta tttgtttatt tttctaaata cattcaaata tgtatccgct catgagacaa   7980
taaccctgat aaatgcttca ataatattga aaaaggaaga gtatgagtat tcaacatttc   8040
cgtgtcgccc ttattccctt ttttgcggca ttttgccttc ctgtttttgc tcacccagaa   8100
acgctggtga aagtaaaaga tgctgaagat cagttgggtg cacgagtggg ttacatcgaa   8160
ctggatctca acagcggtaa gatccttgag agttttcgcc ccgaagaacg ttttccaatg   8220
atgagcactt ttaaagttct gctatgtggc gcggtattat cccgtattga cgccgggcaa   8280
gagcaactcg gtcgccgcat acactattct cagaatgact tggttgagta ctcaccagtc   8340
acagaaaagc atcttacgga tggcatgaca gtaagagaat tatgcagtgc tgccataacc   8400
atgagtgata acactgcggc caacttactt ctgacaacga tcggaggacc gaaggagcta   8460
accgcttttt tgcacaacat gggggatcat gtaactcgcc ttgatcgttg ggaaccggag   8520
ctgaatgaag ccataccaaa cgacgagcgt gacaccacga tgcctgtagc aatggcaaca   8580
acgttgcgca aactattaac tggcgaacta cttactctag cttcccggca acaattaata   8640
gactggatgg aggcggataa agttgcagga ccacttctgc gctcggccct tccggctggc   8700
```

```
tggtttattg ctgataaatc tggagccggt gagcgtgggt ctcgcggtat cattgcagca   8760

ctggggccag atggtaagcc ctcccgtatc gtagttatct acacgacggg gagtcaggca   8820

actatggatg aacgaaatag acagatcgct gagataggtg cctcactgat taagcattgg   8880

taactgtcag accaagttta ctcatatata ctttagattg atttaaaact tcatttttaa   8940

tttaaaagga tctaggtgaa gatccttttt gataatctca tgaccaaaat cccttaacgt   9000

gagttttcgt tccactgagc gtcagacccc gtagaaaaga tcaaaggatc ttcttgagat   9060

cctttttttc tgcgcgtaat ctgctgcttg caaacaaaaa aaccaccgct accagcggtg   9120

gtttgtttgc cggatcaaga gctaccaact ctttttccga aggtaactgg cttcagcaga   9180

gcgcagatac caaatactgt ccttctagtg tagccgtagt taggccacca cttcaagaac   9240

tctgtagcac cgcctacata cctcgctctg ctaatcctgt taccagtggc tgctgccagt   9300

ggcgataagt cgtgtcttac cgggttggac tcaagacgat agttaccgga taaggcgcag   9360

cggtcgggct gaacgggggg ttcgtgcaca cagcccagct tggagcgaac gacctacacc   9420

gaactgagat acctacagcg tgagcattga gaaagcgcca cgcttcccga agggagaaag   9480

gcggacaggt atccggtaag cggcagggtc ggaacaggag agcgcacgag ggagcttcca   9540

gggggaaacg cctggtatct ttatagtcct gtcgggtttc gccacctctg acttgagcgt   9600

cgatttttgt gatgctcgtc aggggggcgg agcctatgga aaaacgccag caacgcggcc   9660

tttttacggt tcctggcctt ttgctggcct tttgctcaca tgttctttcc tgcgttatcc   9720

cctgattctg tggataaccg tattaccgcc tttgagtgag ctgataccgc tcgccgcagc   9780

cgaacgaccg agcgcagcga gtcagtgagc gaggaagcgg aagagcgccc aatacgcaaa   9840

ccgcctctcc ccgcgcgttg gccgattcat taatgcaggt taacctggct tatcgaaatt   9900

aatacgactc actataggga gaccggcaga tccgc                              9935
```

```
<210> SEQ ID NO 10
<211> LENGTH: 70
<212> TYPE: DNA
<213> ORGANISM: Artificial
<220> FEATURE:
<223> OTHER INFORMATION: Primer

<400> SEQUENCE: 10

cttttacaa caaatataaa accaaaagcg gccgcttaat taaaaaatga ctgccgacaa     60

caatagtatg                                                           70


<210> SEQ ID NO 11
<211> LENGTH: 61
<212> TYPE: DNA
<213> ORGANISM: Artificial
<220> FEATURE:
<223> OTHER INFORMATION: Primer

<400> SEQUENCE: 11

agagacatgg gagatcccgc gggcggccgc ttaattaatt atagcattct atgaatttgc     60

c                                                                    61


<210> SEQ ID NO 12
<211> LENGTH: 14515
<212> TYPE: DNA
<213> ORGANISM: Artificial
<220> FEATURE:
<223> OTHER INFORMATION: vector for expression of I. batatas IspS in T.
      reesei named pCIL-105
```

<400> SEQUENCE: 12

```
gtttaaactc aggtcaacca ccgaggacca gcctttgacc gccattgctc ccgttcgtgc     60
cggcagagtt gggtctggat acgccgtctt catacctatc cagctctcac catgcagggt    120
ttccatctgt ttgaagcatc cattcgcagc gcgcgagacc gctactgctt cgtgactata    180
cagtacatgt aataccaaca ggagtcgagg atacgagtac taagtaccac ctattaatct    240
gctgctcgtg cctcgtccgc attgaaagcg aggtaaggta ggcagaaccg ctgacccgtc    300
ccccatcagg tgatgataca acagggtagt actgcggtga cctcgagata aagtacacct    360
cgtgctctgg acgccggcaa cggtacccca atccgaggtc caaatctgct cgcgcggcct    420
gaggcagaga caccaccgtt tgttgatctc ggttgcccca tcagccagcc agcgcacctc    480
agttaggctc ggacctgggc aaaagttggg gtaacaaagg ccggcggcca aagcacccaa    540
gtacctctgc ccgccattgc gggtgcagag gtgacttccg cgggccatca cggtggcgcc    600
ccttgcaggg agtggtgcgt catcggctcg tcagcacggc caatagacgc aaccggcggc    660
cctgctttca atgttgactg ccccaggccg agtccagtga ccacccgata gcaccatcgc    720
agccacccca aatgcgacct gcaccgcgct ggccagggcc cttcggggcg cctgttagtg    780
cctgcggttg ctcggcgggc gggctgctta acgtgctttg cgtgctgagc tgcctgcctg    840
ccgcccgctc gccttatcta atgcccgcta cctctcctcc gtactccgtc cctacaaaga    900
ggctggttcc tagcttcgtc atcctccaag ttcccttcct ctggcagcaa tcgaaccatc    960
ccattcatta attaagctcc ttattgaagt cggaggacgg agcggtgtca agaggatatt   1020
cttcgactct gtattataga taagatgatg aggaattgga ggtagcatag cttcatttgg   1080
atttgctttc caggctgaga ctctagcttg gagcatagag ggtcctttgg ctttcaatat   1140
tctcaagtat ctcgagtttg aacttattcc ctgtgaacct tttattcacc aatgagcatt   1200
ggaatgaaca tgaatctgag gactgcaatc gccatgaggt tttcgaaata catccggatg   1260
tcgaaggctt ggggcacctg cgttggttga atttagaacg tggcactatt gatcatccga   1320
tagctctgca aagggcgttg cacaatgcaa gtcaaacgtt gctagcagtt ccaggtggaa   1380
tgttatgatg agcattgtat taaatcagga gatatagcat gatctctagt tagctcacca   1440
caaaagtcag acggcgtaac caaaagtcac acaacacaag ctgtaaggat ttcggcacgg   1500
ctacggaaga cggagaagcc accttcagtg gactcgagta ccatttaatt ctatttgtgt   1560
ttgatcgaga cctaatacag cccctacaac gaccatcaaa gtcgtatagc taccagtgag   1620
gaagtggact caaatcgact tcagcaacat ctcctggata aactttaagc ctaaactata   1680
cagaataaga taggtggaga gcttataccg agctcccaaa tctgtccaga tcatggttga   1740
ccggtgcctg gatcttccta tagaatcatc cttattcgtt gacctagctg attctggagt   1800
gacccagagg gtcatgactt gagcctaaaa tccgccgcct ccaccatttg tagaaaaatg   1860
tgacgaactc gtgagctctg tacagtgacc ggtgactctt tctggcatgc ggagagacgg   1920
acggacgcag agagaagggc tgagtaataa gccactggcc agacagctct ggcggctctg   1980
aggtgcagtg gatgattatt aatccgggac cggccgcccc tccgccccga agtggaaagg   2040
ctggtgtgcc cctcgttgac caagaatcta ttgcatcatc ggagaatatg gagcttcatc   2100
gaatcaccgg cagtaagcga aggagaatgt gaagccaggg gtgtatagcc gtcggcgaaa   2160
tagcatgcca ttaacctagg tacagaagtc caattgcttc cgatctggta aaagattcac   2220
gagatagtac cttctccgaa gtaggtagag cgagtacccg gcgcgtaagc tccctaattg   2280
gcccatccgg catctgtagg gcgtccaaat atcgtgcctc tcctgctttg cccggtgtat   2340
```

```
gaaaccggaa aggccgctca ggagctggcc agcggcgcag accgggaaca caagctggca   2400
gtcgacccat ccggtgctct gcactcgacc tgctgaggtc cctcagtccc tggtaggcag   2460
ctttgccccg tctgtccgcc cggtgtgtcg gcggggttga caaggtcgtt gcgtcagtcc   2520
aacatttgtt gccatatttt cctgctctcc ccaccagctg ctcttttctt ttctctttct   2580
tttcccatct tcagtatatt catcttccca tccaagaacc tttatttccc ctaagtaagt   2640
actttgctac atccatactc catccttccc atcccttatt cctttgaacc tttcagttcg   2700
agctttccca cttcatcgca gcttgactaa cagctacccc gcttgagcag acatcatgac   2760
tgcccgccgc tcagcaaact atcaaccctc ctcatggtct tacgacgaat acttggtgga   2820
cactactact aacgacagca aactgcgcat tcaagaagac gctcgtaaaa aattggaaga   2880
agaagtgcgt aacgttctgg aagatggcaa attggaaacc ttagcactgt tggaactgat   2940
tgatgacatc caacggctgg gcttgggtta taaatttcgc gaaagcacca gtacttccct   3000
ggctatgttg aaaatgagtg tggggcagga agcatccaac agcagtttgc attcttgttc   3060
attgtacttt cgtttactgc gggaacacgg cttcgatatt acccccgacg tgttcgaaaa   3120
attcaaagat gaaaacggta aatttaaaga tagcatcgct aaagatgttc gcgggttgtt   3180
atcattgtat gaagcaagct tttagggtt cgaaggcgaa aacattttgg acgaagcccg    3240
cgaattcacc actatgcatc tgaataacat caaagataaa gtgaatcccc gtatcgcgga   3300
agaagttaac catgctttag aactgccgtt gcaccgccgt gtggaacgtc tggaagctcg   3360
gcgccgtatt caaagctata gtaaatccgg tgaaaccaat caggccctgc tgaccctggc   3420
taaaatcgat tttaacaccg tgcaggcggt ttaccaacgg gatctgcagg acgttagtaa   3480
atggtggaaa gacactgcat tggccgataa attatccttc gcccgggatc gcctgatgga   3540
aagctttttc tgggcgattg gtatgagcta tgatccccaa cactctaaat cacgggaagc   3600
cgtgaccaaa acttttaaac tggtgaccgt tttggatgac gtgtatgacg tttacgggtc   3660
tttagatgaa ctggaaaaat tcaccgccgc cgccgaacgt tgggatgttg acgcgattaa   3720
agatctgccg gactacatga aattgtgtta cttatccctg tttaataccg tgaacgatct   3780
ggcttatgac accttgaaag ataaaggcga aactgttatt cctatcatga agaaagcctg   3840
ggctgattta ctgaaagcat ttctgcagga agcccaatgg atctacaaca aatacacccc   3900
aactttcgat gaatacctga ataacgcccg tttcagcgtg agtggttgcg tgatgttggt   3960
tcatagctac tttaccactc agaacatcac caaagaagcg atccattctc tggaaaacta   4020
ccacgacttg ttaatttggc ctagcatcgt tttccgttta gcaaatgatc tgtcctcttc   4080
aaaagccgaa attgaacggg gcgaaaccgc gaatagcatc acttgttata tgaacgaaac   4140
cggtcaaagt gaagaacagg cccgtgaaca catttccaaa ctgatcgatg aatgcttcaa   4200
gaaaatgaac aaagaaatgc tggccacctc cacttctccg tttgaaaaat ccttcattga   4260
aaccgcgatc aacttagcac gcattgccct gtgccagtat caatacggcg atgcccatag   4320
cgatccagat gttcgggcac gcaaccgcat tgtgtcagtt atcattaatc cagtggaatg   4380
gtcccaccca caatttgaaa agtaagatcc acttaacgtt actgaaatca tcaaacagct   4440
tgacgaatct ggatataaga tcgttggtgt cgatgtcagc tccggagttg agacaaatgg   4500
tgttcaggat ctcgataaga tacgttcatt tgtccaagca gcaaagagtg ccttctagtg   4560
atttaatagc tccatgtcaa caagaataaa acgcgtttcg ggtttacctc ttccagatac   4620
agctcatctg caatgcatta atgcattgga cctcgcaacc ctagtacgcc cttcaggctc   4680
```

```
cggcgaagca gaagaatagc ttagcagagt ctattttcat tttcgggaga cgagatcaag   4740
cagatcaacg gtcgtcaaga gacctacgag actgaggaat ccgctcttgg ctccacgcga   4800
ctatatattt gtctctaatt gtactttgac atgctcctct tctttactct gatagcttga   4860
ctatgaaaat tccgtcacca gcccctgggt tcgcaaagat aattgcactg tttcttcctt   4920
gaactctcaa gcctacagga cacacattca tcgtaggtat aaacctcgaa aatcattcct   4980
actaagatgg gtatacaata gtaaccatgc atggttgcct agtgaatgct ccgtaacacc   5040
caatacgccg gccgaaactt ttttacaact ctcctatgag tcgtttaccc agaatgcaca   5100
ggtacacttg tttagaggta atccttcttt ctagaagtcc tcgtgtactg tgtaagcgcc   5160
cactccacat ctccactctt aattaagcgg ccgcataacg gtgagactag cggccggtcc   5220
ccttatccca gctgttccac gttggcctgc ccctcagtta gcgctcaact caatgcccct   5280
cactggcgag gcgagggcaa ggatggaggg gcagcatcgc ctgagttgga gcaaagcggc   5340
cccatgggag cagcgaacca acggagggat gccgtgcttt gtcgtggctg ctgtggccaa   5400
tccgggccct tggttggctc acagagcgtt gctgtgagac catgagctat tattgctagg   5460
tacagtatag agagaggaga gagagagaga gagagagaga ggggaaaaaa ggtgaggttg   5520
aagtgagaaa aaaaaaaaaa aaaaaaaatc caaccactga cggctgccgg ctctgccacc   5580
cccctccctc caccccagac cacctgcaca ctcagcgcgc agcatcacct aatcttggct   5640
cgccttcccg cagctcaggt tgtttttttt ttctctctcc ctcgtcgaag ccgcccttgt   5700
tcccttattt atttccctct ccatccttgt ctgcctttgg tccatctgcc cctttgtctg   5760
catctctttt gcacgcatcg ccttatcgtc gtctcttttt tcactcacgg gagcttgacg   5820
aagacctgac tcgtgagcct cacctgctga tttctctccc cccctcccga ccggcttgac   5880
ttttgtttct cctccagtac cttatcgcga agccggaaga acctcttaac ctctagatga   5940
aaaagcctga actcaccgcg acgtctgtcg agaagttcct gatcgaaaag ttcgacagcg   6000
tctccgacct gatgcagctc tcggagggcg aagaatctcg tgctttcagc ttcgatgtag   6060
gagggcgtgg atatgtcctg cgggtaaata gctgcgccga tggtttctac aaagatcgtt   6120
atgtttatcg gcactttgca tcggccgcgc tcccgattcc ggaagtgctt gacattgggg   6180
aattcagcga gagcctgacc tattgcatct cccgccgtgc acagggtgtc acgttgcaag   6240
acctgcctga aaccgaactg cccgctgttc tgcagccggt cgcggaggcc atggatgcga   6300
tcgctgcggc cgatctcagc cagacgagcg ggttcggccc attcggaccg caaggaatcg   6360
gtcaatacac tacatggcgt gatttcatat gcgcgattgc tgatccccat gtgtatcact   6420
ggcaaactgt gatggacgac accgtcagtg cgtccgtcgc gcaggctctc gatgagctga   6480
tgctttgggc cgaggactgc cccgaagtcc ggcacctcgt gcacgcggat ttcggctcca   6540
acaatgtcct gacggacaat ggccgcataa cagcggtcat tgactggagc gaggcgatgt   6600
tcggggattc ccaatacgag gtcgccaaca tcttcttctg gaggccgtgg ttggcttgta   6660
tggagcagca gacgcgctac ttcgagcgga ggcacccgga gcttgcagga tcgccgcggc   6720
tccgggcgta tatgctccgc attggtcttg accaactcta tcagagcttg gttgacggca   6780
atttcgatga tgcagcttgg gcgcagggtc gatgcgacgc aatcgtccga tccggagccg   6840
ggactgtcgg gcgtacacaa atcgcccgca gaagcgcggc cgtctggacc gatggctgtg   6900
tagaagtact cgccgatagt ggaaaccgac gccccagcac tcgtccgagg gcaaaggaat   6960
agatgcatgg ctttcgtgac cgggcttcaa acaatgatgt gcgatggtgt ggttcccggt   7020
tggcggagtc tttgtctact ttggttgtct gtcgcaggtc ggtagaccgc aaatgagcaa   7080
```

```
ctgatggatt gttgccagcg atactataat tcacatggat ggtctttgtc gatcagtagc   7140
tagtgagaga gagagaacat ctatccacaa tgtcgagtgt ctattagaca tactccgaga   7200
ataaagtcaa ctgtgtctgt gatctaaaga tcgattcggc agtcgagtag cgtataacaa   7260
ctccgagtac cagcgaaagc acgtcgtgac aggagcaggg ctttgccaac tgcgcaacct   7320
tgcttgaatg aggatacacg gggtgcaaca tggctgtact gatccatcgc aaccaaaatt   7380
tctgtttata gatcaagctg gtagattcca attactccac ctcttgcgct tctccatgac   7440
atgtaagtgc acgtggaaac catacccaaa ttgcctacag ctgcggagca tgagcctatg   7500
gcgatcagtc tggtcatgtt aaccagcctg tgctctgacg ttaatgcaga atagaaagcc   7560
gcggttgcaa tgcaaatgat gatgcctttg cagaaatggc ttgctcgctg actgatacca   7620
gtaacaactt tgcttggccg tctagcgctg ttgattgtat tcatcacaac ctcgtctccc   7680
tcctttgggt tgagctcttt ggatggcttt ccaaacgtta atagcgcgtt tttctccaca   7740
aagtattcgt atggacgcgc ttttgcgtgt attgcgtgag ctaccagcag cccaattggc   7800
gaagtcttga gccgcatcgc atagaataat tgattgcgca tttgatgcga tttttgagcg   7860
gctgtttcag gcgacatttc gcccgccctt atttgctcca ttatatcatc gacggcatgt   7920
ccaatagccc ggtgatagtc ttgtcgaata tggctgtcgt ggataaccca tcggcagcag   7980
atgataatga ttccgcagca cgcggccgca ggtagacgct ttgcgagtgt gtgtgtatct   8040
aagaagtgca catcctgtat gtttgcagaa tgctgggtag ttttggttat ttgggcagtt   8100
tgagagcgga agacagtcct actgctgcgg aggagtctgg atcaagattg caacgtcgtt   8160
tatgtaataa ctataatgga gactggccgt cgtctgctgc cgctatttgg ttcggtgtca   8220
tgatctcgtg cctttgcgag gcgctcatct cgattgattg attgattggc ctgtctcgac   8280
atgtcgatac taaccttgcc gcggccgaac gattccattt ttgcttgctt ggtcaattgt   8340
actggtgtcg ccgggacctt tgtcagagcg agctgcccgt acctaccaac tacctagtag   8400
gtgccatcaa atgacgtgct gcaagctatc gcgaccagcc aggtcagccg cgtgtcacat   8460
gtaaggtcag agctaataag atgcgacatt ctgtgcattg ctagcaccgc caatactagc   8520
acgaaacggc tttggcacct cagtggcagg ccgaagttcg cgtgggatgg gatccattta   8580
ttaccctgca ttatacgggg agagctacag gtcttgagcg agtatcatcc aacgggcagt   8640
tgtttataag gatcaaagga caggttgtta ataccgaatt tacattaaga agtagaatgc   8700
aagatgagtt gtgaactgta atctcctgtg tttactgccc aaggtaggtg gcttagcatg   8760
ttagcagcaa tacattctta cctgtagcat ctggcgccgc tacctagtat caatatgatc   8820
caggcactaa ggcgtgttcc gcctcgacta cctcacagat gcatgatgca agttttgatg   8880
gaaaatgtcc gcgtctctgc tttcaacaaa ggccgccaac cgcccgctcc agccaaacaa   8940
gaacgcggct gcaataccca tcatctttca cagacaagcc gaatcagtcc gcgtcagttc   9000
agtttaaacg ctgtttcctg tgtgaaattg ttatccgctc acaattccac acaacatagg   9060
agccggaagc ataaagtgta aagcctgggg tgcctaatga gtgaggtaac tcacattaat   9120
tgcgttgcgc tcactgcccg ctttccagtc gggaaacctg tcgtgccagc tgcattaatg   9180
aatcggccaa cgcgcgggga gaggcggttt gcgtattggg cgctcttccg cttcctcgct   9240
cactgactcg ctgcgctcgg tcgttcggct gcggcgagcg gtatcagctc actcaaaggc   9300
ggtaatacgg ttatccacag aatcagggga taacgcagga aagaacatgt gagcaaaagg   9360
ccagcaaaag gccaggaacc gtaaaaaggc cgcgttgctg gcgtttttcc ataggctccg   9420
```

```
ccccccctgac gagcatcaca aaaatcgacg ctcaagtcag aggtggcgaa acccgacagg   9480
actataaaga taccaggcgt ttccccctgg aagctccctc gtgcgctctc ctgttccgac   9540
cctgccgctt accggatacc tgtccgcctt tctcccttcg ggaagcgtgg cgctttctca   9600
tagctcacgc tgtaggtatc tcagttcggt gtaggtcgtt cgctccaagc tgggctgtgt   9660
gcacgaaccc cccgttcagc ccgaccgctg cgccttatcc ggtaactatc gtcttgagtc   9720
caacccggta agacacgact tatcgccact ggcagcagcc actggtaaca ggattagcag   9780
agcgaggtat gtaggcggtg ctacagagtt cttgaagtgg tggcctaact acggctacac   9840
tagaaggaca gtatttggta tctgcgctct gctgaagcca gttaccttcg gaaaaagagt   9900
tggtagctct tgatccggca aacaaaccac cgctggtagc ggtggttttt ttgtttgcaa   9960
gcagcagatt acgcgcagaa aaaaaggatc tcaagaagat cctttgatct tttctacggg  10020
gtctgacgct cagtggaacg aaaactcacg ttaagggatt ttggtcatga gattatcaaa  10080
aaggatcttc acctagatcc ttttaaatta aaaatgaagt tttaaatcaa tctaaagtat  10140
atatgagtaa acttggtctg acagttacca atgcttaatc agtgaggcac ctatctcagc  10200
gatctgtcta tttcgttcat ccatagttgc ctgactcccc gtcgtgtaga taactacgat  10260
acgggagggc ttaccatctg gccccagtgc tgcaatgata ccgcgagacc cacgctcacc  10320
ggctccagat ttatcagcaa taaaccagcc agccggaagg gccgagcgca gaagtggtcc  10380
tgcaacttta tccgcctcca tccagtctat taattgttgc cgggaagcta gagtaagtag  10440
ttcgccagtt aatagtttgc gcaacgttgt tgccattgct acaggcatcg tggtgtcacg  10500
ctcgtcgttt ggtatggctt cattcagctc cggttcccaa cgatcaaggc gagttacatg  10560
atcccccatg ttgtgcaaaa aagcggttag ctccttcggt cctccgatcg ttgtcagaag  10620
taagttggcc gcagtgttat cactcatggt tatggcagca ctgcataatt ctcttactgt  10680
catgccatcc gtaagatgct tttctgtgac tggtgagtac tcaaccaagt cattctgaga  10740
atagtgtatg cggcgaccga gttgctcttg cccggcgtca atacgggata ataccgcgcc  10800
acatagcaga actttaaaag tgctcatcat tggaaaacgt tcttcggggc gaaaactctc  10860
aaggatctta ccgctgttga gatccagttc gatgtaaccc actcgtgcac ccaactgatc  10920
ttcagcatct tttactttca ccagcgtttc tgggtgagca aaaacaggaa ggcaaaatgc  10980
cgcaaaaaag ggaataaggg cgacacggaa atgttgaata ctcatactct tcctttttca  11040
atattattga agcatttatc agggttattg tctcatgagc ggatacatat ttgaatgtat  11100
ttagaaaaat aaacaaatag gggttccgcg cacatttccc cgaaaagtgc cacctgaacg  11160
aagcatctgt gcttcatttt gtagaacaaa aatgcaacgc gagagcgcta atttttcaaa  11220
caaagaatct gagctgcatt tttacagaac agaaatgcaa cgcgaaagcg ctattttacc  11280
aacgaagaat ctgtgcttca tttttgtaaa acaaaaatgc aacgcgagag cgctaatttt  11340
tcaaacaaag aatctgagct gcatttttac agaacagaaa tgcaacgcga gagcgctatt  11400
ttaccaacaa agaatctata cttctttttt gttctacaaa aatgcatccc gagagcgcta  11460
tttttctaac aaagcatctt agattacttt ttttctcctt tgtgcgctct ataatgcagt  11520
ctcttgataa ctttttgcac tgtaggtccg ttaaggttag aagaaggcta ctttggtgtc  11580
tattttctct tccataaaaa aagcctgact ccacttcccg cgtttactga ttactagcga  11640
agctgcgggt gcattttttc aagataaagg catccccgat tatattctat accgatgtgg  11700
attgcgcata ctttgtgaac agaaagtgat agcgttgatg attcttcatt ggtcagaaaa  11760
ttatgaacgg tttcttctat tttgtctcta tatactacgt ataggaaatg tttacatttt  11820
```

```
cgtattgttt tcgattcact ctatgaatag ttcttactac aatttttttg tctaaagagt  11880
aatactagag ataaacataa aaaatgtaga ggtcgagttt agatgcaagt tcaaggagcg  11940
aaaggtggat gggtaggtta tatagggata tagcacagag atatatagca aagagatact  12000
tttgagcaat gtttgtggaa gcggtattcg caatatttta gtagctcgtt acagtccggt  12060
gcgtttttgg ttttttgaaa gtgcgtcttc agagcgcttt tggttttcaa aagcgctctg  12120
aagttcctat actttctaga gaataggaac ttcggaatag gaacttcaaa gcgtttccga  12180
aaacgagcgc ttccgaaaat gcaacgcgag ctgcgcacat acagctcact gttcacgtcg  12240
cacctatatc tgcgtgttgc ctgtatatat atatacatga gaagaacggc atagtgcgtg  12300
tttatgctta aatgcgtact tatatgcgtc tatttatgta ggatgaaagg tagtctagta  12360
cctcctgtga tattatccca ttccatgcgg ggtatcgtat gcttccttca gcactaccct  12420
ttagctgttc tatatgctgc cactcctcaa ttggattagt ctcatccttc aatgctatca  12480
tttcctttga tattggatca tactaagaaa ccattattat catgacatta acctataaaa  12540
ataggcgtat cacgaggccc tttcgtctcg cgcgtttcgg tgatgacggt gaaaacctct  12600
gacacatgca gctcccggag acggtcacag cttgtctgta agcggatgcc gggagcagac  12660
aagcccgtca gggcgcgtca gcgggtgttg gcgggtgtcg gggctggctt aactatgcgg  12720
catcagagca gattgtactg agagtgcacc ataccacagc ttttcaattc aattcatcat  12780
ttttttttta ttcttttttt tgatttcggt ttctttgaaa tttttttgat tcggtaatct  12840
ccgaacagaa ggaagaacga aggaaggagc acagacttag attggtatat atacgcatat  12900
gtagtgttga agaaacatga aattgcccag tattcttaac ccaactgcac agaacaaaaa  12960
cctgcaggaa acgaagataa atcatgtcga aagctacata taaggaacgt gctgctactc  13020
atcctagtcc tgttgctgcc aagctattta atatcatgca cgaaaagcaa acaaacttgt  13080
gtgcttcatt ggatgttcgt accaccaagg aattactgga gttagttgaa gcattaggtc  13140
ccaaaatttg tttactaaaa acacatgtgg atatcttgac tgatttttcc atggagggca  13200
cagttaagcc gctaaaggca ttatccgcca agtacaattt tttactcttc gaagacagaa  13260
aatttgctga cattggtaat acagtcaaat tgcagtactc tgcgggtgta tacagaatag  13320
cagaatgggc agacattacg aatgcacacg gtgtggtggg cccaggtatt gttagcggtt  13380
tgaagcaggc ggcagaagaa gtaacaaagg aacctagagg ccttttgatg ttagcagaat  13440
tgtcatgcaa gggctcccta tctactggag aatatactaa gggtactgtt gacattgcga  13500
agagcgacaa agattttgtt atcggcttta ttgctcaaag agacatgggt ggaagagatg  13560
aaggttacga ttggttgatt atgacacccg gtgtgggttt agatgacaag ggagacgcat  13620
tgggtcaaca gtatagaacc gtggatgatg tggtctctac aggatctgac attattattg  13680
ttggaagagg actatttgca aagggaaggg atgctaaggt agagggtgaa cgttacagaa  13740
aagcaggctg ggaagcatat ttgagaagat gcggccagca aaactaaaaa actgtattat  13800
aagtaaatgc atgtatacta aactcacaaa ttagagcttc aatttaatta tatcagttat  13860
taccctatgc ggtgtgaaat accgcacaga tgcgtaagga gaaaataccg catcaggaaa  13920
ttgtaaacgt taatattttg ttaaaattcg cgttaaattt ttgttaaatc agctcatttt  13980
ttaaccaata ggccgaaatc ggcaaaatcc cttataaatc aaaagaatag accgagatag  14040
ggttgagtgt tgttccagtt tggaacaaga gtccactatt aaagaacgtg gactccaacg  14100
tcaaagggcg aaaaaccgtc tatcagggcg atggcccact acgtgaacca tcaccctaat  14160
```

```
caagtttttt ggggtcgagg tgccgtaaag cactaaatcg gaaccctaaa gggagccccc  14220

gatttagagc ttgacgggga aagccggcga acgtggcgag aaaggaaggg aagaaagcga  14280

aaggagcggg cgctagggcg ctggcaagtg tagcggtcac gctgcgcgta accaccacac  14340

ccgccgcgct taatgcgccg ctacagggcg cgtcgcgcca ttcgccattc aggctgcgca  14400

actgttggga agggcgatcg gtgcgggcct cttcgctatt acgccagctg gcgaaagggg  14460

gatgtgctgc aaggcgatta agttgggtaa cgccagggtt ttcccagtca cgacg       14515
```

<210> SEQ ID NO 13
<211> LENGTH: 20
<212> TYPE: DNA
<213> ORGANISM: Artificial
<220> FEATURE:
<223> OTHER INFORMATION: 77579_5f primer

<400> SEQUENCE: 13

```
tcaggtcaac caccgaggac                                              20
```

<210> SEQ ID NO 14
<211> LENGTH: 20
<212> TYPE: DNA
<213> ORGANISM: Artificial
<220> FEATURE:
<223> OTHER INFORMATION: 77579_5r primer

<400> SEQUENCE: 14

```
tgaatgggat ggttcgattg                                              20
```

<210> SEQ ID NO 15
<211> LENGTH: 20
<212> TYPE: DNA
<213> ORGANISM: Artificial
<220> FEATURE:
<223> OTHER INFORMATION: 77579_3f primer

<400> SEQUENCE: 15

```
aggtagacgc tttgcgagtg                                              20
```

<210> SEQ ID NO 16
<211> LENGTH: 18
<212> TYPE: DNA
<213> ORGANISM: Artificial
<220> FEATURE:
<223> OTHER INFORMATION: 77579_3r primer

<400> SEQUENCE: 16

```
tgaactgacg cggactga                                                18
```

<210> SEQ ID NO 17
<211> LENGTH: 59
<212> TYPE: DNA
<213> ORGANISM: Artificial
<220> FEATURE:
<223> OTHER INFORMATION: C017_gpdA_rec_for primer

<400> SEQUENCE: 17

```
cctctggcag caatcgaacc atcccattca ttaattaagc tccttattga agtcggagg   59
```

<210> SEQ ID NO 18
<211> LENGTH: 58
<212> TYPE: DNA
<213> ORGANISM: Artificial
<220> FEATURE:
<223> OTHER INFORMATION: C018_gpdA_rec_rev primer

<400> SEQUENCE: 18
atgaggaggg ttgatagttt gctgagcggc gggcagtcat gatgtctgct caagcggg 58

<210> SEQ ID NO 19
<211> LENGTH: 65
<212> TYPE: DNA
<213> ORGANISM: Artificial
<220> FEATURE:
<223> OTHER INFORMATION: C019_trpC_rec_for primer

<400> SEQUENCE: 19
taatccagtg gaatggtccc acccacaatt tgaaaagtaa gatccactta acgttactga 60
aatca 65

<210> SEQ ID NO 20
<211> LENGTH: 66
<212> TYPE: DNA
<213> ORGANISM: Artificial
<220> FEATURE:
<223> OTHER INFORMATION: C020_trpC_rec_rev primer

<400> SEQUENCE: 20
aaggggaccg gccgctagtc tcaccgttat gcggccgctt aattaagagt ggagatgtgg 60
agtggg 66

<210> SEQ ID NO 21
<211> LENGTH: 60
<212> TYPE: DNA
<213> ORGANISM: Artificial
<220> FEATURE:
<223> OTHER INFORMATION: C021_pep4_3frec_for primer

<400> SEQUENCE: 21
gataacccat cggcagcaga tgataatgat tccgcagcac gcggccgcag gtagacgctt 60

<210> SEQ ID NO 22
<211> LENGTH: 20
<212> TYPE: DNA
<213> ORGANISM: Artificial
<220> FEATURE:
<223> OTHER INFORMATION: C022_pep4_3f_rev primer

<400> SEQUENCE: 22
gaggtgccaa agccgtttcg 20

<210> SEQ ID NO 23
<211> LENGTH: 20
<212> TYPE: DNA
<213> ORGANISM: Artificial
<220> FEATURE:
<223> OTHER INFORMATION: T302_77579_5int primer

<400> SEQUENCE: 23
gattcatcac aggggcagtc 20

<210> SEQ ID NO 24
<211> LENGTH: 21
<212> TYPE: DNA
<213> ORGANISM: Artificial
<220> FEATURE:
<223> OTHER INFORMATION: T624_gpdA_seqR1 primer

<400> SEQUENCE: 24

```
ctccatattc tccgatgatg c                                              21


<210> SEQ ID NO 25
<211> LENGTH: 20
<212> TYPE: DNA
<213> ORGANISM: Artificial
<220> FEATURE:
<223> OTHER INFORMATION: T302_77579_5int primer

<400> SEQUENCE: 25

gattcatcac aggggcagtc                                                20


<210> SEQ ID NO 26
<211> LENGTH: 20
<212> TYPE: DNA
<213> ORGANISM: Artificial
<220> FEATURE:
<223> OTHER INFORMATION: C046_gpdA_rev primer

<400> SEQUENCE: 26

tatcctcttg acaccgctcc                                                20


<210> SEQ ID NO 27
<211> LENGTH: 19
<212> TYPE: DNA
<213> ORGANISM: Artificial
<220> FEATURE:
<223> OTHER INFORMATION: T415_77579_3screen primer

<400> SEQUENCE: 27

acgccgttgc tgagccttg                                                 19


<210> SEQ ID NO 28
<211> LENGTH: 20
<212> TYPE: DNA
<213> ORGANISM: Artificial
<220> FEATURE:
<223> OTHER INFORMATION: T1411_cbh2t_end_f primer

<400> SEQUENCE: 28

ccaatagccc ggtgatagtc                                                20


<210> SEQ ID NO 29
<211> LENGTH: 19
<212> TYPE: DNA
<213> ORGANISM: Artificial
<220> FEATURE:
<223> OTHER INFORMATION: T415_77579_3screen primer

<400> SEQUENCE: 29

acgccgttgc tgagccttg                                                 19


<210> SEQ ID NO 30
<211> LENGTH: 20
<212> TYPE: DNA
<213> ORGANISM: Artificial
<220> FEATURE:
<223> OTHER INFORMATION: T1404_cbh2term_for primer

<400> SEQUENCE: 30

ccgtctagcg ctgttgattg                                                20


<210> SEQ ID NO 31
<211> LENGTH: 20
<212> TYPE: DNA
<213> ORGANISM: Artificial
```

<220> FEATURE:
<223> OTHER INFORMATION: C009_Ibat_for1 primer

<400> SEQUENCE: 31
gatcaactta gcacgcattg 20

<210> SEQ ID NO 32
<211> LENGTH: 18
<212> TYPE: DNA
<213> ORGANISM: Artificial
<220> FEATURE:
<223> OTHER INFORMATION: C029_PKIp_rev primer

<400> SEQUENCE: 32
tttgctccaa ctcaggcg 18

<210> SEQ ID NO 33
<211> LENGTH: 1650
<212> TYPE: DNA
<213> ORGANISM: Artificial
<220> FEATURE:
<223> OTHER INFORMATION: polynucleotide sequence encoding the isoprene synthase optimized by codon optimization for yeast

<400> SEQUENCE: 33
atgacagcca gaagatcagc aaactatcaa ccttcatcat ggtcctacga cgaatacttg 60
gtcgatacaa caacaaacga ttctaaatta agaatacaag aagacgcaag aaagaaattg 120
gaagaagaag taagaaacgt tttggaagat ggtaaattag aaactttggc cttgttggaa 180
ttgatcgatg acattcaaag attgggttta ggttacaagt ttagagaatc aacatccacc 240
agtttagcca tgttgaagat gtcagttggt caagaagcat ctaattcttc tttgcattct 300
tgttcattgt actttagatt gttgagagaa cacggtttcg atataacacc agacgtattc 360
gaaaaattca aggatgaaaa cggtaaattc aaagattcta tcgctaagga tgttagaggt 420
ttgttaagtt tatatgaagc atcatttttg ggtttcgaag gtgaaaacat attggatgaa 480
gctagagagt ttactacaat gcacttgaat aacatcaagg ataaggtcaa cccaagaata 540
gcagaagaag taaaccatgc cttggaatta cctttgcaca gaagagttga aagattagaa 600
gctagaagaa gaatacaatc ctacagtaag tctggtgaaa ccaatcaagc attgttgact 660
ttggcaaaga tcgatttcaa cactgtccaa gcagtatacc aaagagattt gcaagacgtt 720
tcaaaatggt ggaaggacac agctttagca gataaattgt ccttcgcaag agatagattg 780
atggaatctt tcttttgggc catcggcatg tcttacgatc cacaacactc aaagtccaga 840
gaagctgtca ctaagacttt taaattggtt accgtcttgg atgacgttta tgacgtctac 900
ggttctttag atgaattgga aaaattcact gctgcagccg aaagatggga tgtagacgct 960
ataaaagatt tgcctgacta catgaagttg tgttacttat cattgtttaa tactgttaac 1020
gatttggcat atgacacatt gaaagataag ggtgaaaccg tcattccaat aatgaaaaag 1080
gcttgggctg atttgttaaa agccttctta caagaagctc aatggatcta taataagtac 1140
acccctactt tcgatgaata cttaaataac gctagattca gtgtttctgg ttgcgtaatg 1200
ttggttcatt cttactttac cactcaaaac atcacaaagg aagcaatcca tagtttggaa 1260
aactaccacg acttgttaat atggccttct atcgtcttca gattagctaa tgatttgtcc 1320
agttctaagg cagaaatcga aagaggtgaa actgccaatt ctatcacatg ttacatgaac 1380
gaaacaggtc aatcagaaga acaagctaga gaacatatct ccaaattgat cgatgaatgc 1440
ttcaaaaaga tgaataagga aatgttggcc acatcaacct ccccatttga aaaatcattc 1500

```
atcgaaaccg ctattaactt agcaagaatt gccttgtgcc aatatcaata cggtgacgct   1560

cactctgatc ctgacgttag agcaagaaat agaatcgtaa gtgtcatcat taatccagtc   1620

gaatggtcac atccacaatt tgaaaagtaa                                    1650
```

<210> SEQ ID NO 34
<211> LENGTH: 1578
<212> TYPE: DNA
<213> ORGANISM: Artificial
<220> FEATURE:
<223> OTHER INFORMATION: Truncated S. cerevisiae HMG1 ORF

<400> SEQUENCE: 34

```
atggaccaat tggtgaaaac tgaagtcacc aagaagtctt ttactgctcc tgtacaaaag     60

gcttctacac cagttttaac caataaaaca gtcatttctg gatcgaaagt caaaagttta    120

tcatctgcgc aatcgagctc atcaggacct tcatcatcta gtgaggaaga tgattcccgc    180

gatattgaaa gcttggataa gaaaatacgt cctttagaag aattagaagc attattaagt    240

agtggaaata caaaacaatt gaagaacaaa gaggtcgctg ccttggttat tcacggtaag    300

ttacctttgt acgctttgga gaaaaaatta ggtgatacta cgagagcggt tgcggtacgt    360

aggaaggctc tttcaatttt ggcagaagct cctgtattag catctgatcg tttaccatat    420

aaaaattatg actacgaccg cgtatttggc gcttgttgtg aaaatgttat aggttacatg    480

cctttgcccg ttggtgttat aggcccottg gttatcgatg gtacatctta tcatatacca    540

atggcaacta cagagggttg tttggtagct tctgccatgc gtggctgtaa ggcaatcaat    600

gctggcggtg gtgcaacaac tgttttaact aaggatggta tgacaagagg cccagtagtc    660

cgtttcccaa ctttgaaaag atctggtgcc tgtaagatat ggttagactc agaagaggga    720

caaaacgcaa ttaaaaaagc ttttaactct acatcaagat ttgcacgtct gcaacatatt    780

caaacttgtc tagcaggaga tttactcttc atgagattta gaacaactac tggtgacgca    840

atgggtatga atatgatttc taaaggtgtc gaatactcat taaagcaaat ggtagaagag    900

tatggctggg aagatatgga ggttgtctcc gtttctggta actactgtac cgacaaaaaa    960

ccagctgcca tcaactggat cgaaggtcgt ggtaagagtg tcgtcgcaga agctactatt   1020

cctggtgatg ttgtcagaaa agtgttaaaa agtgatgttt ccgcattggt tgagttgaac   1080

attgctaaga atttggttgg atctgcaatg gctgggtctg ttggtggatt taacgcacat   1140

gcagctaatt tagtgacagc tgttttcttg gcattaggac aagatcctgc acaaaatgtt   1200

gaaagttcca actgtataac attgatgaaa gaagtggacg gtgatttgag aatttccgta   1260

tccatgccat ccatcgaagt aggtaccatc ggtggtggta ctgttctaga accacaaggt   1320

gccatgttgg acttattagg tgtaagaggc ccgcatgcta ccgctcctgg taccaacgca   1380

cgtcaattag caagaatagt tgcctgtgcc gtcttggcag gtgaattatc cttatgtgct   1440

gccctagcag ccggccattt ggttcaaagt catatgaccc acaacaggaa acctgctgaa   1500

ccaacaaaac ctaacaattt ggacgccact gatataaatc gtttgaaaga tgggtccgtc   1560

acctgcatta aatcctaa                                                 1578
```

<210> SEQ ID NO 35
<211> LENGTH: 867
<212> TYPE: DNA
<213> ORGANISM: Artificial
<220> FEATURE:
<223> OTHER INFORMATION: S. cerevisiae IDI1 ORF

<400> SEQUENCE: 35

```
atgactgccg acaacaatag tatgccccat ggtgcagtat ctagttacgc caaattagtg     60
caaaaccaaa cacctgaaga cattttggaa gagtttcctg aaattattcc attacaacaa    120
agacctaata cccgatctag tgagacgtca aatgacgaaa gcggagaaac atgtttttct    180
ggtcatgatg aggagcaaat taagttaatg aatgaaaatt gtattgtttt ggattgggac    240
gataatgcta ttggtgccgg taccaagaaa gtttgtcatt taatggaaaa tattgaaaag    300
ggtttactac atcgtgcatt ctccgtcttt attttcaatg aacaaggtga attactttta    360
caacaaagag ccactgaaaa aataactttc cctgatcttt ggactaacac atgctgctct    420
catccactat gtattgatga cgaattaggt ttgaagggta agctagacga taagattaag    480
ggcgctatta ctgcggcggt gagaaaacta gatcatgaat taggtattcc agaagatgaa    540
actaagacaa ggggtaagtt tcacttttta aacagaatcc attacatggc accaagcaat    600
gaaccatggg gtgaacatga aattgattac atcctatttt ataagatcaa cgctaaagaa    660
aacttgactg tcaacccaaa cgtcaatgaa gttagagact tcaaatgggt ttcaccaaat    720
gatttgaaaa ctatgtttgc tgacccaagt tacaagttta cgccttggtt taagattatt    780
tgcgagaatt acttattcaa ctggtgggag caattagatg acctttctga agtggaaaat    840
gacaggcaaa ttcatagaat gctataa                                        867
```

<210> SEQ ID NO 36
<211> LENGTH: 1650
<212> TYPE: DNA
<213> ORGANISM: Artificial
<220> FEATURE:
<223> OTHER INFORMATION: I. batatas IspS with C-terminal strepII tag (underlined) for expression in T. reesei

<400> SEQUENCE: 36

```
atgactgccc gccgctcagc aaactatcaa ccctcctcat ggtcttacga cgaatacttg     60
gtggacacta ctactaacga cagcaaactg cgcattcaag aagacgctcg taaaaaattg    120
gaagaagaag tgcgtaacgt tctggaagat ggcaaattgg aaaccttagc actgttggaa    180
ctgattgatg acatccaacg gctgggcttg ggttataaat ttcgcgaaag caccagtact    240
tccctggcta tgttgaaaat gagtgtgggg caggaagcat ccaacagcag tttgcattct    300
tgttcattgt actttcgttt actgcgggaa cacggcttcg atattacccc cgacgtgttc    360
gaaaaattca aagatgaaaa cggtaaattt aaagatagca tcgctaaaga tgttcgcggg    420
ttgttatcat tgtatgaagc aagcttttta gggttcgaag gcgaaaacat tttggacgaa    480
gcccgcgaat tcaccactat gcatctgaat aacatcaaag ataaagtgaa tccccgtatc    540
gcggaagaag ttaaccatgc tttagaactg ccgttgcacc gccgtgtgga acgtctggaa    600
gctcggcgcc gtattcaaag ctatagtaaa tccggtgaaa ccaatcaggc cctgctgacc    660
ctggctaaaa tcgattttaa caccgtgcag gcggtttacc aacgggatct gcaggacgtt    720
agtaaatggt ggaaagacac tgcattggcc gataaattat ccttcgcccg ggatcgcctg    780
atggaaagct tttctgggc gattggtatg agctatgatc cccaacactc taaatcacgg    840
gaagccgtga ccaaaacttt taaactggtg accgttttgg atgacgtgta tgacgtttac    900
gggtctttag atgaactgga aaaattcacc gccgccgccg aacgttggga tgttgacgcg    960
attaaagatc tgccggacta catgaaattg tgttacttat ccctgtttaa taccgtgaac   1020
gatctggctt atgacacctt gaaagataaa ggcgaaactg ttattcctat catgaagaaa   1080
```

```
gcctgggctg atttactgaa agcatttctg caggaagccc aatggatcta caacaaatac   1140

accccaactt tcgatgaata cctgaataac gcccgtttca gcgtgagtgg ttgcgtgatg   1200

ttggttcata gctactttac cactcagaac atcaccaaag aagcgatcca ttctctggaa   1260

aactaccacg acttgttaat ttggcctagc atcgttttcc gtttagcaaa tgatctgtcc   1320

tcttcaaaag ccgaaattga acggggcgaa accgcgaata gcatcacttg ttatatgaac   1380

gaaaccggtc aaagtgaaga acaggcccgt gaacacattt ccaaactgat cgatgaatgc   1440

ttcaagaaaa tgaacaaaga aatgctggcc acctccactt ctccgtttga aaaatccttc   1500

attgaaaccg cgatcaactt agcacgcatt gccctgtgcc agtatcaata cggcgatgcc   1560

catagcgatc cagatgttcg ggcacgcaac cgcattgtgt cagttatcat taatccagtg   1620

gaatggtccc acccacaatt tgaaaagtaa                                    1650
```

```
<210> SEQ ID NO 37
<211> LENGTH: 553
<212> TYPE: PRT
<213> ORGANISM: Quercus petraea

<400> SEQUENCE: 37

Met Thr Glu Arg Gln Ser Ala Asn Phe Gln Pro Ser Leu Trp Ser Tyr
1               5                   10                  15

Glu Tyr Ile Gln Ser Leu Lys Asn Gly Tyr Glu Ala Asp Leu Tyr Glu
            20                  25                  30

Asp Arg Ala Lys Lys Leu Gly Glu Glu Val Arg Arg Met Ile Asn Asn
        35                  40                  45

Lys Asp Thr Lys Leu Leu Thr Thr Leu Glu Leu Ile Asp Asp Ile Glu
    50                  55                  60

Arg Leu Gly Leu Gly Tyr Arg Phe Lys Glu Glu Ile Met Arg Ala Leu
65                  70                  75                  80

Asp Arg Phe Val Thr Leu Lys Gly Cys Glu Glu Phe Thr Asn Gly Ser
                85                  90                  95

Ile His Asp Thr Ala Leu Ser Phe Arg Leu Leu Arg Gln His Gly Phe
            100                 105                 110

Gly Val Ser Gln Asp Met Phe Asn Cys Phe Lys Asp Gln Lys Gly Asn
        115                 120                 125

Phe Lys Glu Cys Leu Ser Lys Asp Ile Lys Gly Leu Leu Ser Leu Tyr
    130                 135                 140

Glu Ala Ser Tyr Leu Gly Phe Glu Gly Glu Asn Leu Leu Asp Glu Ala
145                 150                 155                 160

Arg Glu Phe Thr Thr Met His Leu Lys Asp Leu Lys Gly Asp Val Ser
                165                 170                 175

Arg Thr Leu Lys Glu Glu Val Arg His Ser Leu Glu Met Pro Leu His
            180                 185                 190

Arg Arg Met Arg Arg Leu Glu Gln Arg Trp Tyr Ile Asp Ala Tyr Asn
        195                 200                 205

Met Lys Glu Ala His Asp Arg Lys Leu Leu Glu Leu Ala Lys Leu Asp
    210                 215                 220

Phe Asn Ile Val Gln Ser Val His Gln Arg Asp Leu Lys Asp Met Ser
225                 230                 235                 240

Arg Trp Trp Gln Glu Met Gly Leu Gly Asn Lys Leu Ser Phe Ala Arg
                245                 250                 255

Asp Arg Leu Met Glu Cys Phe Phe Phe Ser Val Gly Met Ala Phe Glu
            260                 265                 270
```

```
Pro Gln Phe Ser Asn Ser Arg Lys Ala Val Thr Lys Met Phe Ser Phe
        275                 280                 285

Ile Thr Val Ile Asp Asp Ile Tyr Asp Val Tyr Ala Thr Leu Glu Glu
    290                 295                 300

Leu Glu Met Phe Thr Asp Ile Val Gln Arg Trp Asp Val Lys Ala Val
305                 310                 315                 320

Lys Asp Leu Pro Glu Tyr Met Lys Leu Cys Phe Leu Ala Leu Phe Asn
                325                 330                 335

Thr Val Asn Glu Met Val Tyr Asp Thr Leu Lys Glu Gln Gly Val Asp
            340                 345                 350

Ile Leu Pro Tyr Leu Thr Lys Ala Trp Gly Asp Ile Cys Lys Ala Phe
        355                 360                 365

Leu Gln Glu Thr Lys Trp Arg Tyr Tyr Lys Arg Thr Pro Ser Ser Glu
    370                 375                 380

Asp Tyr Leu Asp Asn Ala Trp Ile Ser Val Ser Gly Ala Leu Leu Leu
385                 390                 395                 400

Ile His Ala Tyr Phe Leu Met Ser Pro Ser Ile Thr Asp Arg Ala Leu
                405                 410                 415

Lys Gly Leu Glu Asp Tyr His Asn Ile Leu Arg Trp Pro Ser Ile Ile
            420                 425                 430

Phe Arg Leu Thr Asn Asp Leu Gly Thr Ser Thr Ala Glu Leu Glu Arg
        435                 440                 445

Gly Glu Thr Ala Asn Ser Ile Leu Cys Tyr Met Arg Glu Thr Ser Arg
    450                 455                 460

Ser Glu Asp Phe Ala Arg Glu His Ile Ser Asn Leu Ile Asp Lys Thr
465                 470                 475                 480

Trp Lys Lys Met Asn Lys Asp Arg Phe Ser Asp Ser Pro Phe Glu Glu
                485                 490                 495

Pro Phe Leu Glu Thr Ala Ile Asn Leu Ala Arg Ile Ser His Cys Ile
            500                 505                 510

Tyr Gln His Gly Asp Gly His Gly Ala Pro Asp Thr Arg Thr Lys Asp
        515                 520                 525

Arg Val Leu Ser Leu Ile Ile Glu Pro Ile Pro Cys Tyr Asp Pro Ser
    530                 535                 540

Thr Asn Phe His Ser Gln Ile His Leu
545                 550


<210> SEQ ID NO 38
<211> LENGTH: 583
<212> TYPE: PRT
<213> ORGANISM: Melaleuca alternifolia

<400> SEQUENCE: 38

Met Ala Leu Arg Leu Leu Ser Thr Pro His Leu Pro Gln Leu Cys Ser
1               5                   10                  15

Arg Arg Val Ser Gly Arg Val His Cys Ser Ala Ser Thr Gln Val Ser
            20                  25                  30

Asp Ala Gln Gly Gly Arg Arg Ser Ala Asn Tyr Gln Pro Ser Val Trp
        35                  40                  45

Thr Tyr Asn Tyr Leu Gln Ser Leu Val Ala Asp Asp Ile Arg Arg Ser
    50                  55                  60

Arg Arg Glu Val Glu Gln Glu Arg Glu Lys Ala Gln Ile Leu Glu Glu
65                  70                  75                  80

Asp Val Arg Gly Ala Leu Asn Asp Gly Asn Ala Glu Pro Met Ala Ile
                85                  90                  95
```

-continued

```
Phe Ala Leu Val Asp Asp Ile Gln Arg Leu Gly Leu Gly Arg Tyr Phe
            100                 105                 110

Glu Glu Asp Ile Ser Lys Ala Leu Arg Arg Cys Leu Ser Gln Tyr Ala
        115                 120                 125

Val Thr Gly Ser Leu Gln Lys Ser Leu His Gly Thr Ala Leu Ser Phe
    130                 135                 140

Arg Val Leu Arg Gln His Gly Phe Glu Val Ser Gln Asp Val Phe Lys
145                 150                 155                 160

Ile Phe Met Asp Glu Ser Gly Ser Phe Met Lys Thr Leu Gly Gly Asp
                165                 170                 175

Val Gln Gly Met Leu Ser Leu Tyr Glu Ala Ser His Leu Ala Phe Glu
            180                 185                 190

Glu Glu Asp Ile Leu His Lys Ala Lys Thr Phe Ala Ile Lys His Leu
        195                 200                 205

Glu Asn Leu Asn His Asp Ile Asp Gln Asp Leu Gln Asp His Val Asn
    210                 215                 220

His Glu Leu Glu Leu Pro Leu His Arg Arg Met Pro Leu Leu Glu Ala
225                 230                 235                 240

Arg Arg Phe Ile Glu Ala Tyr Ser Arg Arg Ser Asn Val Asn Pro Arg
                245                 250                 255

Ile Leu Glu Leu Ala Val Met Lys Phe Asn Ser Ser Gln Leu Thr Leu
            260                 265                 270

Gln Arg Asp Leu Gln Asp Met Leu Gly Trp Trp Asn Asn Val Gly Leu
        275                 280                 285

Ala Lys Arg Leu Ser Phe Ala Arg Asp Arg Leu Met Glu Cys Phe Phe
    290                 295                 300

Trp Ala Val Gly Ile Ala Arg Glu Pro Ala Leu Ser Asn Cys Arg Lys
305                 310                 315                 320

Gly Val Thr Lys Ala Phe Ser Leu Ile Leu Val Leu Asp Asp Val Tyr
                325                 330                 335

Asp Val Phe Gly Thr Leu Asp Glu Leu Glu Leu Phe Thr Asp Ala Val
            340                 345                 350

Arg Arg Trp His Glu Asp Ala Val Glu Asn Leu Pro Gly Tyr Met Lys
        355                 360                 365

Leu Cys Phe Leu Ala Leu Tyr Asn Ser Val Asn Asp Met Ala Tyr Glu
    370                 375                 380

Thr Leu Lys Glu Thr Gly Glu Asn Val Thr Pro Tyr Leu Thr Lys Val
385                 390                 395                 400

Trp Tyr Asp Leu Cys Lys Ala Phe Leu Gln Glu Ala Lys Trp Ser Tyr
                405                 410                 415

Asn Lys Ile Thr Pro Gly Val Glu Glu Tyr Leu Asn Asn Gly Trp Val
            420                 425                 430

Ser Ser Ser Gly Gln Val Met Leu Thr His Ala Tyr Phe Leu Ser Ser
        435                 440                 445

Pro Ser Leu Arg Lys Glu Glu Leu Glu Ser Leu Glu His Tyr His Asp
    450                 455                 460

Leu Leu Arg Leu Pro Ser Leu Ile Phe Arg Leu Thr Asn Asp Leu Ala
465                 470                 475                 480

Thr Ser Ser Ala Glu Leu Gly Arg Gly Glu Thr Thr Asn Ser Ile Leu
                485                 490                 495

Cys Tyr Met Arg Glu Lys Gly Phe Ser Glu Ser Glu Ala Arg Lys Gln
            500                 505                 510
```

```
Val Ile Glu Gln Ile Asp Thr Ala Trp Arg Gln Met Asn Lys Tyr Met
        515                 520                 525

Val Asp His Ser Thr Phe Asn Arg Ser Phe Met Gln Met Thr Tyr Asn
    530                 535                 540

Leu Ala Arg Met Ala His Cys Val Tyr Gln Asp Gly Asp Ala Ile Gly
545                 550                 555                 560

Ala Pro Asp Asp Gln Ser Trp Asn Arg Val His Ser Leu Ile Ile Lys
                565                 570                 575

Pro Val Ser Leu Ala Pro Cys
            580


<210> SEQ ID NO 39
<211> LENGTH: 582
<212> TYPE: PRT
<213> ORGANISM: Eucalyptus globulus

<400> SEQUENCE: 39

Met Ala Leu Arg Leu Leu Phe Thr Pro His Leu Pro Val Leu Ser Ser
1               5                   10                  15

Arg Arg Ala Asn Gly Arg Val Arg Cys Ser Ala Ser Thr Gln Ile Ser
            20                  25                  30

Asp Pro Gln Glu Gly Arg Arg Ser Ala Asn Tyr Gln Pro Ser Val Trp
        35                  40                  45

Thr Tyr Asn Tyr Leu Gln Ser Ile Val Ala Gly Glu Gly Arg Gln Ser
    50                  55                  60

Arg Arg Glu Val Glu Gln Gln Lys Glu Lys Val Gln Ile Leu Glu Glu
65                  70                  75                  80

Glu Val Arg Gly Ala Leu Asn Asp Glu Lys Ala Glu Thr Phe Thr Ile
                85                  90                  95

Phe Ala Thr Val Asp Asp Ile Gln Arg Leu Gly Leu Gly Asp His Phe
            100                 105                 110

Glu Glu Asp Ile Ser Asn Ala Leu Arg Arg Cys Val Ser Lys Gly Ala
        115                 120                 125

Val Phe Met Ser Leu Gln Lys Ser Leu His Gly Thr Ala Leu Gly Phe
    130                 135                 140

Arg Leu Leu Arg Gln His Gly Tyr Glu Val Ser Gln Asp Val Phe Lys
145                 150                 155                 160

Ile Phe Leu Asp Glu Ser Gly Ser Phe Val Lys Thr Leu Gly Gly Asp
                165                 170                 175

Val Gln Gly Val Leu Ser Leu Tyr Glu Ala Ser His Leu Ala Phe Glu
            180                 185                 190

Glu Glu His Ile Leu His Lys Ala Arg Ser Phe Ala Ile Lys His Leu
        195                 200                 205

Glu Asn Leu Asn Ser Asp Val Asp Lys Asp Leu Gln Asp Gln Val Lys
    210                 215                 220

His Glu Leu Glu Leu Pro Leu His Arg Arg Met Pro Leu Leu Glu Ala
225                 230                 235                 240

Arg Arg Ser Ile Glu Ala Tyr Ser Arg Arg Gly Tyr Thr Asn Pro Gln
                245                 250                 255

Ile Leu Glu Leu Ala Leu Thr Asp Phe Asn Val Ser Gln Ser Tyr Leu
            260                 265                 270

Gln Arg Asp Leu Gln Glu Met Leu Gly Trp Trp Asn Asn Thr Gly Leu
        275                 280                 285

Ala Lys Arg Leu Ser Phe Ala Arg Asp Arg Leu Ile Glu Cys Phe Phe
    290                 295                 300
```

```
Trp Ala Val Gly Ile Ala His Glu Pro Ser Leu Ser Ile Cys Arg Lys
305                 310                 315                 320

Ala Val Thr Lys Ala Phe Ala Leu Ile Leu Val Leu Asp Asp Val Tyr
                325                 330                 335

Asp Val Phe Gly Thr Leu Glu Glu Leu Glu Leu Phe Thr Asp Ala Val
            340                 345                 350

Arg Arg Trp Asp Leu Asn Ala Val Glu Asp Leu Pro Val Tyr Met Lys
        355                 360                 365

Leu Cys Tyr Leu Ala Leu Tyr Asn Ser Val Asn Glu Met Ala Tyr Glu
    370                 375                 380

Thr Leu Lys Glu Lys Gly Glu Asn Val Ile Pro Tyr Leu Ala Lys Ala
385                 390                 395                 400

Trp Tyr Asp Leu Cys Lys Ala Phe Leu Gln Glu Ala Lys Trp Ser Asn
                405                 410                 415

Ser Arg Ile Ile Pro Gly Val Glu Glu Tyr Leu Asn Asn Gly Trp Val
            420                 425                 430

Ser Ser Ser Gly Ser Val Met Leu Ile His Ala Tyr Phe Leu Ala Ser
        435                 440                 445

Pro Ser Ile Arg Lys Glu Glu Leu Glu Ser Leu Glu His Tyr His Asp
    450                 455                 460

Leu Leu Arg Leu Pro Ser Leu Ile Phe Arg Leu Thr Asn Asp Ile Ala
465                 470                 475                 480

Ser Ser Ser Ala Glu Leu Glu Arg Gly Glu Thr Thr Asn Ser Ile Arg
                485                 490                 495

Cys Phe Met Gln Glu Lys Gly Ile Ser Glu Leu Glu Ala Arg Glu Cys
            500                 505                 510

Val Lys Glu Glu Ile Asp Thr Ala Trp Lys Lys Met Asn Lys Tyr Met
        515                 520                 525

Val Asp Arg Ser Thr Phe Asn Gln Ser Phe Val Arg Met Thr Tyr Asn
    530                 535                 540

Leu Ala Arg Met Ala His Cys Val Tyr Gln Asp Gly Asp Ala Ile Gly
545                 550                 555                 560

Ser Pro Asp Asp Leu Ser Trp Asn Arg Val His Ser Leu Ile Ile Lys
                565                 570                 575

Pro Ile Ser Pro Ala Ala
            580


<210> SEQ ID NO 40
<211> LENGTH: 595
<212> TYPE: PRT
<213> ORGANISM: Populus alba

<400> SEQUENCE: 40

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
```

```
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Gly Ala Leu Asp Arg Phe Val Ser Ser Gly Gly Phe Asp Ala Val Thr
    130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
    450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510
```

```
Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595


<210> SEQ ID NO 41
<211> LENGTH: 595
<212> TYPE: PRT
<213> ORGANISM: Populus canescens

<400> SEQUENCE: 41

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Phe Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
```

-continued

```
        275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Ile Phe Ala Tyr Phe Ala Val Val Gln Asn Ile Lys
    450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Cys Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595


<210> SEQ ID NO 42
<211> LENGTH: 595
<212> TYPE: PRT
<213> ORGANISM: Salix sp.

<400> SEQUENCE: 42

Met Ala Thr Glu Leu Leu Cys Leu His Arg Pro Ile Ser Leu Thr Pro
1               5                   10                  15

Lys Leu Phe Arg Asn Pro Leu Pro Lys Val Ile Leu Ala Thr Pro Leu
            20                  25                  30

Thr Leu Lys Leu Arg Cys Ser Val Ser Thr Glu Asn Val Ser Phe Thr
        35                  40                  45
```

```
Glu Thr Glu Thr Glu Thr Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Ala Val Thr
    130                 135                 140

Lys Thr Ser Leu His Ala Thr Ala Leu Ser Phe Arg Phe Leu Arg Gln
145                 150                 155                 160

His Gly Phe Glu Val Ser Gln Glu Ala Phe Gly Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Asp Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Glu
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
    450                 455                 460

Lys Glu Glu Ile Glu Asn Leu Gln Lys Tyr His Asp Ile Ile Ser Arg
```

465 470 475 480

Pro Ser His Ile Phe Arg Leu Cys Asn Asp Leu Ala Ser Ala Ser Ala
485 490 495

Glu Ile Ala Arg Gly Glu Thr Ala Asn Ser Val Ser Cys Tyr Met Arg
500 505 510

Thr Lys Gly Ile Ser Glu Glu Leu Ala Thr Glu Ser Val Met Asn Leu
515 520 525

Ile Asp Glu Thr Trp Lys Lys Met Asn Lys Glu Lys Leu Gly Gly Ser
530 535 540

Leu Phe Pro Lys Pro Phe Val Glu Thr Ala Ile Asn Leu Ala Arg Gln
545 550 555 560

Ser His Cys Thr Tyr His Asn Gly Asp Ala His Thr Ser Pro Asp Glu
565 570 575

Leu Thr Arg Lys Arg Val Leu Ser Val Ile Thr Glu Pro Ile Leu Pro
580 585 590

Phe Glu Arg
595

<210> SEQ ID NO 43
<211> LENGTH: 541
<212> TYPE: PRT
<213> ORGANISM: Wisteria sp.

<400> SEQUENCE: 43

Arg Arg Ser Gly Asn Tyr Gln Pro Asn Leu Trp Asn Phe Asp Phe Leu
1 5 10 15

Gln Ser Gln Lys Asn Asp Leu Lys Glu Glu Met Leu Gln Glu Arg Ala
20 25 30

Gly Lys Leu Glu Glu Glu Val Arg Gly Leu Ile Asn Glu Val Asp Thr
35 40 45

Glu Pro Leu Ser Leu Leu Glu Leu Ile Asp Asn Val Glu Arg Leu Gly
50 55 60

Leu Thr Tyr Lys Phe Gln Glu Asp Ile Asn Lys Ala Leu Gly Arg Ile
65 70 75 80

Val Ser Ser Asp Ile Asn Lys Ser Gly Leu His Ala Ala Ala Leu Thr
85 90 95

Phe Arg Leu Leu Arg Gln His Gly Phe Gln Ile Ser Gln Asp Val Phe
100 105 110

Glu Lys Phe Lys Asp Lys Glu Gly Arg Phe Ser Ala Glu Ile Lys Gly
115 120 125

Asp Val Gln Gly Leu Leu Ser Leu Tyr Glu Ala Ser Tyr Leu Gly Phe
130 135 140

Glu Gly Glu Asn Val Leu Glu Glu Ala Arg Ala Phe Ser Thr Thr His
145 150 155 160

Leu Arg Asn Ile Lys Gln Gly Val Ser Thr Lys Met Ala Glu Gln Ile
165 170 175

Ser His Ala Leu Glu Leu Pro Tyr His Arg Arg Leu Gln Arg Leu Glu
180 185 190

Ala Arg Arg Phe Ile Asp Lys Phe Glu Ile Lys Glu Pro Gln Asp Arg
195 200 205

Leu Leu Leu Glu Leu Ala Lys Leu Asp Phe Asn Met Val Gln Thr Leu
210 215 220

Gln Gln Lys Glu Leu Arg Asp Leu Ser Arg Trp Trp Lys Glu Ile Gly
225 230 235 240

-continued

```
Leu Ala Arg Lys Met Glu Phe Val Arg Asp Arg Leu Met Glu Val Tyr
            245                 250                 255

Phe Trp Ala Val Gly Met Ala Pro Asp Pro Leu Leu Ser Asp Cys Arg
            260                 265                 270

Lys Ala Ile Ala Lys Met Phe Gly Leu Val Thr Ile Ile Asp Asp Val
        275                 280                 285

Tyr Asp Val Tyr Gly Thr Leu Asp Glu Leu Gln Leu Phe Thr Asp Ala
    290                 295                 300

Val Glu Arg Trp Asp Val Asn Ala Leu Asp Thr Leu Pro Asp Tyr Met
305                 310                 315                 320

Lys Leu Cys Phe Leu Ala Leu Tyr Asn Thr Val Asn Asp Thr Ala Tyr
            325                 330                 335

Ser Leu Leu Arg Glu Arg Gly Asp Asn Ser Leu Pro Tyr Leu Ala Lys
            340                 345                 350

Ser Trp Ser Glu Leu Cys Lys Ala Phe Leu Gln Glu Ala Lys Trp Ser
        355                 360                 365

Asn Lys Lys Thr Ile Pro Glu Phe Arg Glu Tyr Leu Asp Asn Ala Ser
    370                 375                 380

Val Ser Ser Ser Gly Gly Ala Leu Leu Thr Pro Cys Tyr Phe Ser Leu
385                 390                 395                 400

Leu Thr Gln Asp Val Ala Val Thr Ser Gln Phe His Ser Ser Thr Ile
            405                 410                 415

Asp Ser Leu Thr Asn Phe His Gly Val Val Arg Ser Ser Cys Thr Ile
            420                 425                 430

Phe Arg Leu Cys Asn Asp Leu Ala Thr Ser Ala Ala Glu Leu Glu Arg
        435                 440                 445

Gly Glu Thr Thr Asn Ser Ile Thr Ser Tyr Met Arg Glu Lys Gly Val
    450                 455                 460

Gly Glu Glu Glu Ala Arg Glu Glu Leu Ser Lys Leu Ile Asp Val Glu
465                 470                 475                 480

Trp Met Lys Leu Asn Arg Glu Arg Val Leu Asp Ile Gly Pro Phe Pro
            485                 490                 495

Lys Ala Phe Met Glu Thr Ala Val Asn Met Ala Arg Val Ser His Cys
            500                 505                 510

Thr Tyr Gln His Gly Asp Gly Leu Gly Arg Pro Asp Asn Thr Ala Gln
        515                 520                 525

Asn Arg Ile Lys Leu Leu Leu Leu Asn Pro Ile Pro Ser
    530                 535                 540


<210> SEQ ID NO 44
<211> LENGTH: 534
<212> TYPE: PRT
<213> ORGANISM: Robinia pseudoacacia

<400> SEQUENCE: 44

Arg Ser Ala Asn Tyr Gln Pro Asn Leu Trp Asn Phe Glu Phe Leu Gln
1               5                   10                  15

Ser Gln Glu Tyr Asp Leu Met Val Glu Thr Leu Gln Glu Arg Ala Thr
            20                  25                  30

Lys Leu Glu Glu Glu Val Arg Arg Leu Ile Asn Arg Val Asp Ile Glu
        35                  40                  45

Pro Leu Lys Leu Leu Glu Leu Val Asp Asn Val Gln Arg Leu Gly Leu
    50                  55                  60

Thr Tyr Lys Phe Glu Asp Asp Ile Asn Lys Ala Leu Glu Arg Ile Val
65                  70                  75                  80
```

```
Ser Leu Asp Glu Arg Glu Lys Ser Gly Leu His Ala Thr Ala Leu Ile
                85                  90                  95

Phe Arg Leu Leu Arg Gln His Gly Phe Glu Val Ser Gln Asp Val Phe
            100                 105                 110

Glu Ser Thr Arg Asp Lys Glu Gly Arg Phe Lys Ala Glu Ile Lys Gly
        115                 120                 125

Asp Val Gln Gly Leu Leu Ser Leu Tyr Glu Ala Ser Tyr Leu Gly Phe
    130                 135                 140

Glu Gly Glu Asn Leu Leu Asp Glu Ala Arg Glu Phe Ser Met Thr His
145                 150                 155                 160

Leu Lys Asn Leu Asn Glu Gly Val Val Thr Pro Lys Leu Ala Glu Gln
                165                 170                 175

Ile Asn His Ala Leu Glu Leu Pro Tyr His Arg Arg Phe Gln Arg Leu
            180                 185                 190

Glu Ala Arg Trp Phe Ile Glu Asn Tyr Glu Val Lys Glu Pro His Asp
        195                 200                 205

Arg Leu Leu Val Glu Leu Ala Lys Leu Asp Phe Asn Met Val Gln Ser
    210                 215                 220

Leu Gln Lys Lys Glu Val Gly Glu Leu Ser Arg Trp Trp Lys Glu Ile
225                 230                 235                 240

Gly Leu Thr Ser Lys Leu Asp Phe Val Arg Asp Arg Leu Val Glu Val
                245                 250                 255

Tyr Phe Trp Ala Ser Gly Met Ala Pro Asp Pro Gln Leu Ser Glu Cys
            260                 265                 270

Arg Lys Ala Val Thr Lys Met Phe Gly Leu Val Thr Ile Ile Asp Asp
        275                 280                 285

Val Tyr Asp Val Tyr Gly Thr Leu Asp Glu Leu Glu Leu Phe Thr Asn
    290                 295                 300

Ala Val Glu Arg Trp Asp Val Asn Ala Val Asp Thr Leu Pro Asp Tyr
305                 310                 315                 320

Met Lys Leu Cys Phe Phe Ala Leu Tyr Asn Thr Val Asn Asp Thr Ala
                325                 330                 335

Tyr Asn Leu Leu Lys Glu Lys Gly Asp Asn Asn Leu Pro Tyr Leu Ala
            340                 345                 350

Lys Ser Trp Ser Asp Leu Cys Lys Ala Phe Leu Gln Glu Ala Lys Trp
        355                 360                 365

Ser Asn Asn Lys Ile Ile Pro Ser Phe Asn Lys Tyr Ile Glu Asn Ala
    370                 375                 380

Ser Val Ser Ser Ser Gly Gly Ala Leu Leu Thr Pro Cys Tyr Phe Ser
385                 390                 395                 400

Ile Arg Gln Asp Ile Thr Asn Gln Ala Leu Asp Ser Leu Thr Asn Tyr
                405                 410                 415

His Gly Pro Val Arg Ser Ser Cys Ala Ile Phe Arg Leu Cys Asn Asp
            420                 425                 430

Leu Ala Thr Ser Ala Ala Glu Leu Glu Arg Gly Glu Thr Thr Asn Ser
        435                 440                 445

Ile Thr Ser Tyr Met Gln Asp Asn Gly Ile Ser Glu Glu Gln Ala Arg
    450                 455                 460

Asp Glu Leu Arg Asn Leu Ile Asp Ala Glu Trp Lys Gln Ile Asn Arg
465                 470                 475                 480

Glu Arg Val Phe Asp Gln Thr Phe Pro Lys Ala Phe Ile Glu Thr Ala
                485                 490                 495
```

```
Ile Asn Met Ala Arg Val Ser His Cys Thr Tyr Gln Tyr Gly Asp Gly
            500                 505                 510

Leu Gly Arg Pro Asp Asn Thr Ala Glu Asn Arg Ile Lys Leu Leu Leu
        515                 520                 525

Ile Asp Pro Phe Pro Ile
    530


<210> SEQ ID NO 45
<211> LENGTH: 544
<212> TYPE: PRT
<213> ORGANISM: Arachis hypogaea

<400> SEQUENCE: 45

Met Asn Thr Arg Arg Ser Ala Asn Tyr Gln Pro Asn Leu Trp Asp Phe
1               5                   10                  15

Glu Phe Leu Gln Ser Val Glu Asn Asp Leu Gln Val Glu Arg Leu Glu
            20                  25                  30

Glu Arg Ala Arg Lys Leu Glu Glu Glu Val Arg Gly Leu Met Lys Lys
        35                  40                  45

Val Glu Ile Glu Pro Leu Ser Leu Leu Glu Leu Met Asp Asn Val Glu
    50                  55                  60

Arg Leu Gly Leu Thr Tyr Lys Phe Glu Glu Asp Ile Lys Ser Ala Leu
65                  70                  75                  80

Asn Asn Arg Ile Val Pro Leu Leu His His His Thr Ile Asn Lys Tyr
                85                  90                  95

Gly Leu His Ala Thr Ala Leu Ser Phe Arg Phe Leu Arg Gln His Ala
            100                 105                 110

Phe His Val Ser Pro Asp Val Phe Glu Ser Phe Lys Glu Glu Gly Lys
        115                 120                 125

Phe Lys Lys Glu Ile Ser Gly Asp Val Leu Gly Leu Leu Asn Leu Tyr
    130                 135                 140

Glu Thr Ser Tyr Leu Gly Phe Glu Gly Glu Thr Ile Leu Asp Glu Ala
145                 150                 155                 160

Arg Ala Phe Ser Ala Thr His Leu Lys Asn Leu Leu Gln Thr Asn Gln
                165                 170                 175

Val Gln Asn Lys Val Met Ala Glu Lys Val Arg His Ala Leu Glu Leu
            180                 185                 190

Pro Tyr His Arg Arg Val His Arg Leu Glu Ala Arg Trp Phe Ile Glu
        195                 200                 205

Arg Tyr Glu Gln Lys Glu Ala His Asp Gly Ala Leu Leu Glu Leu Ala
    210                 215                 220

Lys Leu Asp Phe Asn Met Val Gln Ser Val Met Lys Lys Glu Leu Gln
225                 230                 235                 240

Glu Leu Ser Arg Trp Trp Arg Glu Ile Gly Leu Thr Ser Lys Leu Asp
                245                 250                 255

Phe Val Arg Asp Arg Leu Met Glu Val Tyr Phe Trp Ala Leu Gly Met
            260                 265                 270

Ala Pro His Pro Gln Leu Thr Glu Cys Arg Lys Ala Val Thr Lys Met
        275                 280                 285

Phe Gly Leu Val Thr Ile Ile Asp Asp Val Tyr Asp Val Tyr Gly Thr
    290                 295                 300

Leu Asp Glu Leu Gln Leu Phe Thr Asp Ala Val Asp Arg Trp Asp Val
305                 310                 315                 320

Asn Ala Val Glu Thr Leu Pro Asp Tyr Met Lys Leu Cys Tyr Leu Ala
                325                 330                 335
```

```
Leu Tyr Asn Ser Val Asn Asp Thr Ala Tyr Ser Thr Leu Arg Glu Lys
            340                 345                 350

Gly Asp Asn Ser Leu Pro His Leu Ala Lys Ser Trp Arg Asp Leu Cys
        355                 360                 365

Lys Ala Phe Leu Gln Glu Ala Lys Trp Ser Asn Asn Lys Ile Ile Pro
    370                 375                 380

Pro Phe Asp Ala Tyr Ile Arg Asn Ala Ser Val Ser Ser Ser Gly Gly
385                 390                 395                 400

Ala Leu Leu Ala Pro Cys Tyr Phe Ser Val Thr Gln Asp Ser Thr Ser
                405                 410                 415

Gln Ala Ile Asp Ser Ile Thr Asn Tyr His Gly Ile Val Arg Ser Ser
            420                 425                 430

Cys Ala Ile Phe Arg Leu Cys Asn Asp Leu Ala Thr Ser Ala Ala Glu
        435                 440                 445

Leu Glu Arg Gly Glu Thr Thr Asn Ser Ile Thr Ser Tyr Met Thr Glu
    450                 455                 460

Asn Gly Thr Thr Glu Glu Glu Ala Arg Glu Ser Leu Gly Lys Leu Ile
465                 470                 475                 480

Asp Gln Glu Trp Lys Lys Met Asn Arg Asp Val Val Leu Glu Ser Ala
                485                 490                 495

Tyr Pro Asn Val Phe Lys Glu Ile Ala Ile Asn Met Ala Arg Val Ser
            500                 505                 510

His Cys Thr Tyr Gln Tyr Gly Asp Gly Leu Gly Arg Pro Asp Asp Thr
        515                 520                 525

Ala Glu Asn Arg Ile Lys Leu Ser Leu Ile Glu Pro Ile Pro Ile Asn
    530                 535                 540


<210> SEQ ID NO 46
<211> LENGTH: 545
<212> TYPE: PRT
<213> ORGANISM: Glycine max

<400> SEQUENCE: 46

Met Glu Thr Arg Arg Ser Ala Asn Tyr Gln Pro Asn Leu Trp Asn Phe
1               5                   10                  15

Glu Phe Leu Pro Pro Ser Leu Glu Asn Asp His Lys Val Glu Lys Leu
            20                  25                  30

Glu Glu Arg Ala Lys Lys Val Glu Glu Glu Val Arg Lys Val Ile Asn
        35                  40                  45

Gly Ile Asp Thr Lys Pro Leu Leu Leu Glu Leu Ile Asp Asp Val Gln
    50                  55                  60

His Leu Gly Leu Thr Tyr Lys Phe Glu Lys Asp Ile Ile Lys Ala Leu
65                  70                  75                  80

Glu Lys Ile Val Ser Leu Asp Glu Asn Glu Glu His Lys Ser Glu Leu
                85                  90                  95

Tyr Tyr Thr Ala Leu Ser Phe Arg Leu Leu Arg Gln His Gly Phe Glu
            100                 105                 110

Val Ser Gln Asp Val Phe Lys Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Asp Asn Leu Leu Asp Glu Ala Arg
145                 150                 155                 160

Ala Phe Ser Thr Thr His Leu Lys Asn Asn Leu Lys Gln Gly Ile Asn
```

```
                165                 170                 175

Thr Lys Glu Ala Glu Gln Val Asn His Ala Leu Glu Leu Pro Tyr His
            180                 185                 190

Arg Arg Leu Gln Arg Leu Glu Ala Arg Trp Tyr Leu Glu Lys Tyr Glu
        195                 200                 205

Pro Lys Glu Pro His His Gln Leu Leu Leu Glu Leu Ala Lys Leu Asp
    210                 215                 220

Phe Asn Met Val Gln Leu Leu His Gln Lys Glu Leu Gln Glu Leu Ser
225                 230                 235                 240

Arg Trp Trp Ser Glu Met Gly Leu Ala Ser Lys Leu Glu Phe Ala Arg
                245                 250                 255

Asp Arg Leu Met Glu Val Tyr Phe Trp Ala Leu Gly Met Ala Pro Asp
            260                 265                 270

Pro Gln Phe Arg Glu Cys Arg Lys Ala Val Thr Lys Met Phe Gly Leu
        275                 280                 285

Val Thr Ile Ile Asp Asp Val Tyr Asp Ile Tyr Gly Thr Leu Asp Glu
    290                 295                 300

Leu Gln Leu Phe Thr Asp Ala Val Glu Arg Trp Asp Val Asn Val Val
305                 310                 315                 320

Asn Thr Leu Pro Asp Tyr Met Lys Leu Cys Tyr Leu Ala Leu Tyr Asn
                325                 330                 335

Thr Val Asn Asp Thr Ala Tyr Ser Ile Leu Lys Glu Lys Gly Arg Asn
            340                 345                 350

Asn Leu Ser Tyr Leu Lys Lys Ser Trp Cys Glu Leu Cys Lys Ala Phe
        355                 360                 365

Leu Gln Glu Ala Lys Trp Ser Asn Asn Lys Ile Val Pro Ala Phe Ser
    370                 375                 380

Lys Tyr Leu Glu Asn Ala Ser Val Ser Ser Ser Gly Val Ala Leu Leu
385                 390                 395                 400

Ala Pro Ser Tyr Phe Ser Val Cys Gln Glu Gln Asp Ile Ser Phe Ser
                405                 410                 415

Asp Lys Thr Leu His Tyr Leu Thr Asn Phe Gly Gly Leu Val Arg Ser
            420                 425                 430

Ser Cys Thr Ile Phe Arg Leu Cys Asn Asp Leu Thr Thr Ser Ala Ala
        435                 440                 445

Glu Leu Glu Arg Gly Glu Thr Thr Asn Ser Ile Met Ser Tyr Met His
    450                 455                 460

Glu Asn Gly Thr Ser Glu Glu His Ala Cys Glu Glu Leu Arg Asn Leu
465                 470                 475                 480

Ile Asp Ile Glu Trp Lys Lys Met Asn Arg Gln Arg Val Ser Asp Ser
                485                 490                 495

Thr Leu Pro Lys Ala Phe Arg Glu Ile Ala Met Asn Met Ala Arg Val
            500                 505                 510

Ser His Asn Thr Tyr Gln Tyr Gly Asp Gly Leu Gly Arg Pro Asp Tyr
        515                 520                 525

Asn Ile Glu Asn Arg Ile Lys Phe Leu Leu Ile Asp Pro Val Pro Ile
    530                 535                 540

Asn
545


<210> SEQ ID NO 47
<211> LENGTH: 608
<212> TYPE: PRT
<213> ORGANISM: Pueraria montana var. lobata
```

<400> SEQUENCE: 47

```
Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Glu Glu Ala Arg Thr Phe Ser Ile Thr His Leu
    210                 215                 220

Lys Asn Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
                245                 250                 255

Ala Arg Trp Phe Leu Asp Lys Tyr Glu Pro Lys Glu Pro His His Gln
            260                 265                 270

Leu Leu Leu Glu Leu Ala Lys Leu Asp Phe Asn Met Val Gln Thr Leu
        275                 280                 285

His Gln Lys Glu Leu Gln Asp Leu Ser Arg Trp Trp Thr Glu Met Gly
    290                 295                 300

Leu Ala Ser Lys Leu Asp Phe Val Arg Asp Arg Leu Met Glu Val Tyr
305                 310                 315                 320

Phe Trp Ala Leu Gly Met Ala Pro Asp Pro Gln Phe Gly Glu Cys Arg
                325                 330                 335

Lys Ala Val Thr Lys Met Phe Gly Leu Val Thr Ile Ile Asp Asp Val
            340                 345                 350

Tyr Asp Val Tyr Gly Thr Leu Asp Glu Leu Gln Leu Phe Thr Asp Ala
        355                 360                 365

Val Glu Arg Trp Asp Val Asn Ala Ile Asn Thr Leu Pro Asp Tyr Met
    370                 375                 380

Lys Leu Cys Phe Leu Ala Leu Tyr Asn Thr Val Asn Asp Thr Ser Tyr
385                 390                 395                 400

Ser Ile Leu Lys Glu Lys Gly His Asn Asn Leu Ser Tyr Leu Thr Lys
```

```
                405                 410                 415

Ser Trp Arg Glu Leu Cys Lys Ala Phe Leu Gln Glu Ala Lys Trp Ser
            420                 425                 430

Asn Asn Lys Ile Ile Pro Ala Phe Ser Lys Tyr Leu Glu Asn Ala Ser
        435                 440                 445

Val Ser Ser Ser Gly Val Ala Leu Leu Ala Pro Ser Tyr Phe Ser Val
    450                 455                 460

Cys Gln Gln Gln Glu Asp Ile Ser Asp His Ala Leu Arg Ser Leu Thr
465                 470                 475                 480

Asp Phe His Gly Leu Val Arg Ser Ser Cys Val Ile Phe Arg Leu Cys
                485                 490                 495

Asn Asp Leu Ala Thr Ser Ala Ala Glu Leu Glu Arg Gly Glu Thr Thr
            500                 505                 510

Asn Ser Ile Ile Ser Tyr Met His Glu Asn Asp Gly Thr Ser Glu Glu
        515                 520                 525

Gln Ala Arg Glu Glu Leu Arg Lys Leu Ile Asp Ala Glu Trp Lys Lys
    530                 535                 540

Met Asn Arg Glu Arg Val Ser Asp Ser Thr Leu Leu Pro Lys Ala Phe
545                 550                 555                 560

Met Glu Ile Ala Val Asn Met Ala Arg Val Ser His Cys Thr Tyr Gln
                565                 570                 575

Tyr Gly Asp Gly Leu Gly Arg Pro Asp Tyr Ala Thr Glu Asn Arg Ile
            580                 585                 590

Lys Leu Leu Leu Ile Asp Pro Phe Pro Ile Asn Gln Leu Met Tyr Val
        595                 600                 605


<210> SEQ ID NO 48
<211> LENGTH: 600
<212> TYPE: PRT
<213> ORGANISM: Mucuna pruriens

<400> SEQUENCE: 48

Met Ala Thr Lys Val Leu Cys Leu Ser Asn Gln Phe Leu Tyr Pro Thr
1               5                   10                  15

Pro Thr Leu Thr Ser Thr Arg Phe Leu Gln Thr Glu Asn Phe Thr Gln
            20                  25                  30

Lys Thr Ser Leu Ile Asn Pro Lys Pro Tyr Pro Leu Phe Cys Val Val
        35                  40                  45

Thr Ser Gln Phe Ser Gln Ile Thr Glu Asp Asn Thr Arg Arg Ser Ala
    50                  55                  60

Asn Tyr His Pro Asn Leu Trp Asn Phe Glu Phe Leu Gln Ser Leu Glu
65                  70                  75                  80

Asn Asp Pro Lys Ile Glu Lys Leu Glu Glu Lys Ala Thr Lys Leu Val
                85                  90                  95

Glu Glu Val Arg His Met Met Asn Lys Ala Glu Thr Glu Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Asn Ala Leu Glu Lys Thr Ile Ser Leu Asp
    130                 135                 140

Glu Asn Gln Lys His Ile Ser Gly Leu His Ala Thr Ser Leu Ser Phe
145                 150                 155                 160

Arg Leu Leu Arg Gln His Gly Phe Glu Val Ser Gln Asp Val Phe Lys
                165                 170                 175
```

```
Lys Phe Lys Asp Glu Asp Gly Gly Phe Ser Ala Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Asp Glu Ala Arg Glu Phe Ser Ile Glu His Leu
    210                 215                 220

Lys Asn Asn Leu Asn Lys Gly Ile Thr Thr Lys Val Ala Glu Gln Val
225                 230                 235                 240

Ser His Ala Leu Glu Leu Pro Tyr His Arg Arg Ile His Arg Leu Glu
                245                 250                 255

Ala Arg Trp Phe Leu Asp Lys Tyr Glu Pro Lys Glu Ser Gln His Lys
            260                 265                 270

Leu Leu Leu Glu Leu Ala Lys Leu Asp Phe Asn Met Val Gln Ser Leu
        275                 280                 285

His Gln Lys Glu Leu Arg Glu Leu Ser Met Trp Trp Arg Glu Ile Gly
    290                 295                 300

Leu Thr Ser Lys Leu Asp Phe Val Arg Asp Arg Leu Met Glu Val Tyr
305                 310                 315                 320

Phe Trp Ala Leu Gly Met Ala Pro Asp Pro Gln Phe Ser Glu Cys Arg
                325                 330                 335

Lys Ala Val Thr Lys Met Phe Gly Leu Val Thr Ile Ile Asp Asp Val
            340                 345                 350

Tyr Asp Val Tyr Gly Thr Leu Asp Glu Leu Gln Leu Phe Thr Asp Ala
        355                 360                 365

Val Glu Arg Trp Asp Val Asn Ala Ile Asn Thr Leu Pro Asp Tyr Met
    370                 375                 380

Lys Leu Cys Phe Leu Ala Leu Tyr Asn Thr Val Asn Asp Thr Thr Tyr
385                 390                 395                 400

Ser Ile Leu Lys Glu Lys Gly His Asn Asn Ile Ser Tyr Leu Thr Lys
                405                 410                 415

Ser Trp Cys Glu Leu Cys Lys Ala Phe Leu Gln Glu Ala Lys Trp Ser
            420                 425                 430

Asn Asn Lys Ile Ile Pro Thr Phe Asn Lys Tyr Leu Arg Asn Ala Ser
        435                 440                 445

Val Ser Ser Ser Gly Val Ala Leu Leu Ala Pro Ser Phe Phe Leu Val
    450                 455                 460

Cys Gln Glu Gln Asp Ile Ser Glu Gln Ala Leu His Ser Leu Ile Asn
465                 470                 475                 480

Phe His Gly Leu Val Arg Ser Ser Cys Val Ile Phe Arg Leu Cys Asn
                485                 490                 495

Asp Leu Ala Thr Ser Ala Ala Glu Leu Glu Arg Gly Glu Thr Thr Asn
            500                 505                 510

Ser Ile Thr Ser Tyr Met His Glu Asn Gly Thr Ser Glu Glu Gln Ala
        515                 520                 525

Arg Gln Glu Leu Arg Ile Leu Ile Asp Ala Glu Trp Lys Asn Met Asn
    530                 535                 540

Gln Glu Arg Tyr Leu Asp Ser Thr Leu Pro Asp Ala Phe Met Glu Ile
545                 550                 555                 560

Thr Ile Asn Leu Ala Arg Val Ser His Cys Thr Tyr Gln Tyr Gly Asp
                565                 570                 575

Gly Leu Gly Arg Pro Asp Tyr Thr Thr Lys Asn Arg Ile Lys Leu Leu
            580                 585                 590

Leu Ile Asp Pro Leu Pro Ile Asn
```

```
        595                 600

<210> SEQ ID NO 49
<211> LENGTH: 545
<212> TYPE: PRT
<213> ORGANISM: Glycine max

<400> SEQUENCE: 49

Met Glu Thr Arg Arg Ser Ala Asn Tyr Gln Pro Asn Leu Trp Asn Phe
1               5                   10                  15

Glu Phe Leu Pro Pro Ser Leu Glu Asn Asp His Lys Val Glu Lys Leu
            20                  25                  30

Glu Glu Arg Ala Arg Lys Val Glu Glu Glu Val Arg Arg Met Ile Asn
        35                  40                  45

Gly Ala Asp Thr Glu Ala Leu Arg Leu Leu Glu Leu Ile Asp Glu Ile
    50                  55                  60

Gln Arg Leu Gly Leu Thr Tyr Lys Phe Glu Lys Asp Ile Phe Lys Ala
65                  70                  75                  80

Leu Glu Lys Thr Ile Ser Leu Asp Glu Asn Glu Lys His Ile Ser Gly
                85                  90                  95

Leu His Ala Thr Ala Leu Ser Phe Arg Leu Leu Arg Gln His Gly Phe
            100                 105                 110

Glu Val Ser Gln Asp Val Phe Lys Arg Phe Lys Asp Lys Glu Gly Gly
        115                 120                 125

Phe Ile Asn Glu Leu Lys Gly Asp Met Gln Gly Leu Leu Ser Leu Tyr
    130                 135                 140

Glu Ala Ser Tyr Leu Gly Phe Glu Gly Glu Thr Leu Leu Asp Glu Ala
145                 150                 155                 160

Arg Ala Tyr Ser Ile Thr His Leu Lys Asn Asn Leu Lys Val Gly Val
                165                 170                 175

Asn Thr Glu Val Lys Glu Gln Val Ser His Ala Leu Glu Leu Pro Tyr
            180                 185                 190

His Arg Gly Leu Asn Arg Leu Glu Ala Arg Trp Phe Leu Glu Lys Tyr
        195                 200                 205

Glu Pro Asn Glu Ser His His His Val Leu Leu Glu Leu Ala Lys Ile
    210                 215                 220

Asp Phe Asn Leu Val Gln Val Met Tyr Gln Lys Glu Leu Arg Glu Leu
225                 230                 235                 240

Ser Arg Trp Trp Ser Glu Met Gly Leu Thr Ser Lys Leu Lys Phe Val
                245                 250                 255

Arg Asp Arg Leu Met Glu Val Tyr Phe Trp Val Leu Gly Met Ala Pro
            260                 265                 270

Arg Pro Gln Phe Ser Glu Cys Arg Lys Ala Val Thr Lys Thr Phe Ala
        275                 280                 285

Leu Ile Gly Ile Ile Asp Asp Val Tyr Asp Val Tyr Gly Thr Leu Asp
    290                 295                 300

Glu Leu Gln Leu Phe Thr Asp Ala Ile Glu Arg Trp Asp Val Asn Ala
305                 310                 315                 320

Met Asn Thr Leu Pro Asp Tyr Met Lys Leu Cys Tyr Leu Ala Val Tyr
                325                 330                 335

Asn Thr Val Asn Asp Thr Cys Tyr Ser Thr Leu Lys Ala Lys Gly His
            340                 345                 350

Asn Asn Met Ser Tyr Leu Thr Lys Ser Trp Cys Glu Leu Cys Lys Ala
        355                 360                 365
```

```
Phe Leu Gln Glu Ala Lys Trp Ser Asn Asn Lys Ile Val Pro Thr Phe
    370                 375                 380

Ser Lys Tyr Leu Glu Asn Ala Ser Val Ser Ser Ser Gly Met Ala Leu
385                 390                 395                 400

Leu Thr Ala Ser Tyr Phe Ser Val Cys Gln Gln Gln Asp Ile Ser Asn
                405                 410                 415

Gln Gln Ala Leu Cys Ser Leu Thr Asn Phe Gln Gly Leu Val Arg Ser
            420                 425                 430

Ser Ser Asn Ile Phe Arg Leu Cys Asn Asp Leu Ala Thr Ser Ala Ala
        435                 440                 445

Glu Leu Glu Thr Gly Glu Thr Ala Asn Ser Ile Thr Cys Tyr Met His
    450                 455                 460

Glu Lys Asp Thr Ser Glu Glu Gln Ala Arg Glu Glu Leu Thr Asn Leu
465                 470                 475                 480

Ile Asp Ala Glu Trp Lys Lys Met Asn Arg Glu Phe Val Ser Asn Ser
                485                 490                 495

Thr Leu Pro Lys Ala Phe Lys Glu Ile Ala Ile Asn Met Ala Arg Val
            500                 505                 510

Ser His Cys Met Tyr Gln Tyr Glu Asp Gly Leu Gly Arg Pro Gly Tyr
        515                 520                 525

Thr Thr Glu Asn Lys Ile Lys Leu Leu Leu Ile Asp Pro Val Pro Ile
    530                 535                 540

Asn
545


<210> SEQ ID NO 50
<211> LENGTH: 598
<212> TYPE: PRT
<213> ORGANISM: Cajanus cajan

<400> SEQUENCE: 50

Met Ala Thr His His Leu Leu Cys Leu Ser Asn Pro Phe Ser Ser Pro
1               5                   10                  15

Ser Pro Thr Leu Ser Thr Ala Thr Arg Ser Phe Pro Leu Thr Asn Asn
            20                  25                  30

Phe Asn His Lys Thr Ser Leu Ala Asn Ser Lys Pro Cys Pro Phe Ile
        35                  40                  45

Cys Ser Gln Ile Thr His His His His Thr Arg Arg Ser Ala Asn Tyr
    50                  55                  60

Gln Pro Asn Leu Trp Asn Phe Glu Phe Leu Gln Ser Leu Gln Asn His
65                  70                  75                  80

His Gln Val Phe Thr Met Phe Arg Arg Lys Leu Glu Lys Glu Val Arg
                85                  90                  95

Cys Met Met Asn Lys Ala Asp Ala Glu Ala Leu Ser Leu Leu Glu Leu
            100                 105                 110

Ile Asp Asp Val Gln Arg Leu Gly Leu Thr Tyr Arg Phe Glu Lys Asp
        115                 120                 125

Ile Ile Lys Val Leu Glu Lys Ile Val Ser Leu Asp Glu Ile Glu Lys
    130                 135                 140

His Gln Ser Gly Leu His Ala Thr Ala Leu Thr Phe Arg Leu Leu Arg
145                 150                 155                 160

Gln His Gly Phe His Gln Val Ser Gln Asp Met Phe Lys Arg Phe Lys
                165                 170                 175

Asp Lys Glu Gly Gly Phe Asn Asp Glu Leu Lys Gly Asp Val Gln Gly
            180                 185                 190
```

```
Leu Leu Ser Leu Tyr Glu Ala Ser Tyr Leu Gly Phe Glu Gly Glu Tyr
        195                 200                 205

Leu Leu Asp Glu Ala Arg Ala Phe Ser Ile Thr His Leu Asn Asn Ser
    210                 215                 220

Leu Lys Gln Gly Ile Asn Thr Lys Leu Ala Glu Gln Val Ser His Ala
225                 230                 235                 240

Leu Gln Leu Pro His His Arg Arg Leu His Arg Leu Glu Ala Arg Trp
                245                 250                 255

Gln Leu Asp Lys Tyr Glu Pro Lys Glu Pro His His His Leu Leu Leu
            260                 265                 270

His Leu Ala Lys Leu Asp Phe Asn Ile Leu Gln Ser Leu Tyr Gln Asn
        275                 280                 285

Glu Leu Arg Glu Leu Ser Arg Trp Trp Arg Glu Met Gly Leu Thr Ser
    290                 295                 300

Lys Leu Glu Phe Val Arg Asp Arg Leu Met Glu Val Tyr Phe Trp Ala
305                 310                 315                 320

Leu Gly Met Ala Pro His Pro Glu Phe Ser Glu Cys Arg Lys Ala Ile
                325                 330                 335

Thr Lys Met Phe Gly Leu Val Thr Ile Ile Asp Asp Val Tyr Asp Val
            340                 345                 350

Tyr Gly Thr Leu Asp Glu Leu Gln Leu Phe Thr Asp Ala Val Glu Arg
        355                 360                 365

Trp Asp Val Asn Val Val Asn Thr Leu Pro Tyr Tyr Met Lys Leu Cys
    370                 375                 380

Tyr Leu Ala Leu Tyr Asn Thr Val Asn Glu Thr Ser Tyr Ser Ile Leu
385                 390                 395                 400

Lys Glu Asn Gly His Asn Ser Leu Ser Tyr Leu Ala Lys Ser Trp Cys
                405                 410                 415

Glu Leu Cys Lys Ala Phe Leu Glu Glu Ala Lys Trp Ser Lys Lys Lys
            420                 425                 430

Val Ile Pro Ala Leu Asn Arg Tyr Leu Glu Asn Ala Trp Val Ser Ser
        435                 440                 445

Ser Gly Val Ala Leu Leu Ala Pro Cys Tyr Phe Ser Val Cys Lys Glu
    450                 455                 460

Glu Asp Lys Ile Ser Asp Glu Ala Leu His Ser Leu Thr Asn Phe His
465                 470                 475                 480

Gly Leu Val Arg Ser Ser Cys Ala Ile Phe Arg Leu Tyr Asn Asp Leu
                485                 490                 495

Ala Thr Ser Ala Ala Glu Leu Glu Arg Asp Glu Thr Thr Asn Ser Met
            500                 505                 510

Thr Cys Tyr Met His Glu Asn Gly Ser Cys Glu Glu Gln Ala Arg Glu
        515                 520                 525

Glu Leu Arg Lys Met Ile Glu Val Glu Trp Lys Lys Met Asn Gln Glu
    530                 535                 540

Gly Val Leu Asp Cys Thr Leu Pro Thr Ala Phe Lys Glu Ile Ala Met
545                 550                 555                 560

Asn Met Ala Arg Val Ser His Cys Thr Tyr Gln His Gly Asp Gly Leu
                565                 570                 575

Gly Arg Pro Asp Tyr Thr Thr Gln Asn Arg Ile Lys Leu Leu Leu Ile
            580                 585                 590

Asp Pro Leu Pro Ile Asn
        595
```

<210> SEQ ID NO 51
<211> LENGTH: 613
<212> TYPE: PRT
<213> ORGANISM: Humulus lupulus

<400> SEQUENCE: 51

```
Met Gln Cys Met Ala Val His Gln Phe Ala Pro Leu Leu Ser Leu Leu
1               5                   10                  15

Asn Cys Ser Arg Ile Ser Ser Asp Phe Gly Arg Leu Phe Thr Pro Lys
            20                  25                  30

Thr Ser Thr Lys Ser Arg Ser Ser Thr Cys His Pro Ile Gln Cys Thr
        35                  40                  45

Val Val Asn Asn Thr Asp Arg Arg Ser Ala Asn Tyr Glu Pro Ser Ile
    50                  55                  60

Trp Ser Phe Asp Tyr Ile Gln Ser Leu Thr Ser Gln Tyr Lys Gly Lys
65                  70                  75                  80

Ser Tyr Ser Ser Arg Leu Asn Glu Leu Lys Lys Glu Val Lys Met Met
                85                  90                  95

Glu Asp Gly Thr Lys Glu Cys Leu Ala Gln Leu Asp Leu Ile Asp Thr
            100                 105                 110

Leu Gln Arg Leu Gly Ile Ser Tyr His Phe Glu Asp Glu Ile Asn Thr
        115                 120                 125

Ile Leu Lys Arg Lys Tyr Ile Asn Ile Gln Asn Asn Ile Asn His Asn
    130                 135                 140

Tyr Asn Leu Tyr Ser Thr Ala Leu Gln Phe Arg Leu Leu Arg Gln His
145                 150                 155                 160

Gly Tyr Leu Val Thr Gln Glu Val Phe Asn Ala Phe Lys Asp Glu Thr
                165                 170                 175

Gly Lys Phe Lys Thr Tyr Leu Ser Asp Asp Ile Met Gly Val Leu Ser
            180                 185                 190

Leu Tyr Glu Ala Ser Phe Tyr Ala Met Lys His Glu Asn Val Leu Glu
        195                 200                 205

Glu Ala Arg Val Phe Ser Thr Glu Cys Leu Lys Glu Tyr Met Met Lys
    210                 215                 220

Met Glu Gln Asn Lys Val Leu Leu Asp His Asp Leu Asp His Asn Asp
225                 230                 235                 240

Asn Phe Asn Val Asn His His Val Leu Ile Ile Asn His Ala Leu Glu
                245                 250                 255

Leu Pro Leu His Trp Arg Ile Thr Arg Ser Glu Ala Arg Trp Phe Ile
            260                 265                 270

Asp Val Tyr Glu Lys Lys Gln Asp Met Asp Ser Thr Leu Leu Glu Phe
        275                 280                 285

Ala Lys Leu Asp Phe Asn Met Val Gln Ser Thr His Gln Glu Asp Leu
    290                 295                 300

Lys His Leu Ser Arg Trp Trp Arg His Ser Lys Leu Gly Glu Lys Leu
305                 310                 315                 320

Asn Phe Ala Arg Asp Arg Leu Met Glu Ala Phe Leu Trp Glu Val Gly
                325                 330                 335

Leu Lys Phe Glu Pro Glu Phe Ser Tyr Phe Lys Arg Ile Ser Ala Arg
            340                 345                 350

Leu Phe Val Leu Ile Thr Ile Ile Asp Asp Ile Tyr Asp Val Tyr Gly
        355                 360                 365

Thr Leu Glu Glu Leu Glu Leu Phe Thr Lys Ala Val Glu Arg Trp Asp
    370                 375                 380
```

```
Val Asn Ala Ile Asn Glu Leu Pro Glu Tyr Met Lys Met Pro Phe Leu
385                 390                 395                 400

Val Leu His Asn Thr Ile Asn Glu Met Ala Phe Asp Val Leu Gly Asp
                405                 410                 415

Gln Asn Phe Leu Asn Ile Glu Tyr Leu Lys Lys Ser Leu Val Asp Leu
            420                 425                 430

Cys Lys Cys Tyr Leu Gln Glu Ala Lys Trp Tyr Tyr Ser Gly Tyr Gln
        435                 440                 445

Pro Thr Leu Gln Glu Tyr Ile Glu Met Ala Trp Leu Ser Ile Gly Gly
    450                 455                 460

Pro Val Ile Leu Val His Ala Tyr Phe Cys Phe Thr Asn Pro Ile Thr
465                 470                 475                 480

Lys Glu Ser Met Lys Phe Phe Thr Glu Gly Tyr Pro Asn Ile Ile Gln
                485                 490                 495

Gln Ser Cys Leu Ile Val Arg Leu Ala Asp Asp Phe Gly Thr Phe Ser
            500                 505                 510

Asp Glu Leu Asn Arg Gly Asp Val Pro Lys Ser Ile Gln Cys Tyr Met
        515                 520                 525

Tyr Asp Thr Gly Ala Ser Glu Asp Glu Ala Arg Glu His Ile Lys Phe
    530                 535                 540

Leu Ile Cys Glu Thr Trp Lys Asp Met Asn Lys Asn Asp Glu Asp Asn
545                 550                 555                 560

Ser Cys Phe Ser Glu Thr Phe Val Glu Val Cys Lys Asn Leu Ala Arg
                565                 570                 575

Thr Ala Leu Phe Met Tyr Gln Tyr Gly Asp Gly His Ala Ser Gln Asn
            580                 585                 590

Cys Leu Ser Lys Glu Arg Ile Phe Ala Leu Ile Ile Asn Pro Ile Asn
        595                 600                 605

Phe His Glu Arg Lys
    610


<210> SEQ ID NO 52
<211> LENGTH: 56
<212> TYPE: PRT
<213> ORGANISM: Quercus petraea

<400> SEQUENCE: 52

Arg Asp Arg Leu Met Glu Cys Phe Phe Phe Phe Ser Phe Ile Thr Val
1               5                   10                  15

Ile Asp Asp Ile Tyr Asp Phe Ser Val Ser Phe Arg Leu Thr Asn Asp
            20                  25                  30

Leu Gly Thr Ser Thr Ala Glu Leu Glu Arg Gly Glu Thr Ala Asn Ser
        35                  40                  45

Ile Tyr Gln His Gly Asp Gly His
    50                  55


<210> SEQ ID NO 53
<211> LENGTH: 56
<212> TYPE: PRT
<213> ORGANISM: Populus alba

<400> SEQUENCE: 53

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30
```

```
Leu Ala Ser Ala Ser Ala Glu Ile Ala Arg Gly Glu Thr Ala Asn Ser
        35                  40                  45

Val Tyr His Asn Gly Asp Ala His
    50                  55


<210> SEQ ID NO 54
<211> LENGTH: 56
<212> TYPE: PRT
<213> ORGANISM: Populus canescens

<400> SEQUENCE: 54

Lys Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55


<210> SEQ ID NO 55
<211> LENGTH: 56
<212> TYPE: PRT
<213> ORGANISM: Salix sp.

<400> SEQUENCE: 55

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55


<210> SEQ ID NO 56
<211> LENGTH: 56
<212> TYPE: PRT
<213> ORGANISM: Melaleuca alternifolia

<400> SEQUENCE: 56

Arg Asp Arg Leu Met Glu Cys Phe Phe Trp Phe Ser Leu Ile Leu Val
1               5                   10                  15

Leu Asp Asp Val Tyr Asp Phe Ser Ser Ser Phe Arg Leu Thr Asn Asp
            20                  25                  30

Leu Ala Thr Ser Ser Ala Glu Leu Gly Arg Gly Glu Thr Thr Asn Ser
        35                  40                  45

Ile Tyr Gln Asp Gly Asp Ala Ile
    50                  55


<210> SEQ ID NO 57
<211> LENGTH: 56
<212> TYPE: PRT
<213> ORGANISM: Eucalyptus globulus

<400> SEQUENCE: 57

Arg Asp Arg Leu Ile Glu Cys Phe Phe Trp Phe Ala Leu Ile Leu Val
1               5                   10                  15

Leu Asp Asp Val Tyr Asp Phe Ser Ser Ser Phe Arg Leu Thr Asn Asp
```

```
            20                  25                  30

Ile Ala Ser Ser Ser Ala Glu Leu Glu Arg Gly Glu Thr Thr Asn Ser
        35                  40                  45

Ile Tyr Gln Asp Gly Asp Ala Ile
    50                  55


<210> SEQ ID NO 58
<211> LENGTH: 56
<212> TYPE: PRT
<213> ORGANISM: Wisteria sp.

<400> SEQUENCE: 58

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln His Gly Asp Gly Leu
    50                  55


<210> SEQ ID NO 59
<211> LENGTH: 56
<212> TYPE: PRT
<213> ORGANISM: Robinia pseudoacacia

<400> SEQUENCE: 59

Arg Asp Arg Leu Val Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55


<210> SEQ ID NO 60
<211> LENGTH: 56
<212> TYPE: PRT
<213> ORGANISM: Arachis hypogaea

<400> SEQUENCE: 60

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55


<210> SEQ ID NO 61
<211> LENGTH: 56
<212> TYPE: PRT
<213> ORGANISM: Glycine max

<400> SEQUENCE: 61

Arg Asp Arg Leu Met Glu Val Tyr Phe Trp Phe Gly Leu Val Thr Ile
1               5                   10                  15
```

```
Ile Asp Asp Val Tyr Asp Phe Ser Ser Ser Phe Arg Leu Cys Asn Asp
            20                  25                  30

Leu Thr Thr Ser Ala Ala Glu Leu Glu Arg Gly Glu Thr Thr Asn Ser
        35                  40                  45

Ile Tyr Gln Tyr Gly Asp Gly Leu
    50                  55


<210> SEQ ID NO 62
<211> LENGTH: 56
<212> TYPE: PRT
<213> ORGANISM: Pueraria montana var. lobata

<400> SEQUENCE: 62

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55


<210> SEQ ID NO 63
<211> LENGTH: 56
<212> TYPE: PRT
<213> ORGANISM: Mucuna pruriens

<400> SEQUENCE: 63

Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55


<210> SEQ ID NO 64
<211> LENGTH: 56
<212> TYPE: PRT
<213> ORGANISM: Glycine max

<400> SEQUENCE: 64

Arg Asp Arg Leu Met Glu Val Tyr Phe Trp Phe Ala Leu Ile Gly Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Thr Gly Glu Thr Ala Asn Ser
        35                  40                  45

Ile Tyr Gln Tyr Glu Asp Gly Leu
    50                  55


<210> SEQ ID NO 65
<211> LENGTH: 56
<212> TYPE: PRT
<213> ORGANISM: Cajanus cajan

<400> SEQUENCE: 65

Arg Asp Arg Leu Met Glu Val Tyr Phe Trp Phe Gly Leu Val Thr Ile
1               5                   10                  15
```

```
Ile Asp Asp Val Tyr Asp Phe Ser Ser Ser Phe Arg Leu Tyr Asn Asp
            20                  25                  30

Leu Ala Thr Ser Ala Ala Glu Leu Glu Arg Asp Glu Thr Thr Asn Ser
        35                  40                  45

Met Tyr Gln His Gly Asp Gly Leu
    50                  55


<210> SEQ ID NO 66
<211> LENGTH: 56
<212> TYPE: PRT
<213> ORGANISM: Humulus lupulus

<400> SEQUENCE: 66

Arg Asp Arg Leu Met Glu Ala Phe Leu Trp Phe Val Leu Ile Thr Ile
1               5                   10                  15

Ile Asp Asp Ile Tyr Asp Tyr Ser Ile Gly Val Arg Leu Ala Asp Asp
            20                  25                  30

Phe Gly Thr Phe Ser Asp Glu Leu Asn Arg Gly Asp Val Pro Lys Ser
        35                  40                  45

Ile Tyr Gln Tyr Gly Asp Gly His
    50                  55


<210> SEQ ID NO 67
<211> LENGTH: 56
<212> TYPE: PRT
<213> ORGANISM: Medicago truncatula

<400> SEQUENCE: 67

Arg Asp Arg Leu Met Glu Cys Phe Phe Trp Cys Ser Leu Ile Thr Leu
1               5                   10                  15

Ile Asp Asp Ile Tyr Asp Phe Ser Val Ser Phe Arg Leu Cys Asn Asp
            20                  25                  30

Leu Ala Thr Ser Ser Ala Glu Leu Glu Arg Gly Glu Gly Ala Asn Ser
        35                  40                  45

Ile Tyr Gln Tyr Gly Asp Gly His
    50                  55


<210> SEQ ID NO 68
<211> LENGTH: 56
<212> TYPE: PRT
<213> ORGANISM: Medicago sativa

<400> SEQUENCE: 68

Arg Asp Arg Leu Met Glu Cys Phe Phe Trp Ser Ser Leu Ile Thr Leu
1               5                   10                  15

Ile Asp Asp Ile Tyr Asp Phe Ser Val Ser Phe Arg Leu Cys Asn Asp
            20                  25                  30

Leu Ala Thr Ser Ser Ala Glu Leu Glu Arg Gly Glu Gly Ala Asn Ser
        35                  40                  45

Ile Tyr Gln Tyr Gly Asp Gly His
    50                  55


<210> SEQ ID NO 69
<211> LENGTH: 56
<212> TYPE: PRT
<213> ORGANISM: Lotus japonicus

<400> SEQUENCE: 69

Arg Asp Arg Leu Met Glu Cys Phe Phe Trp Thr Ser Leu Ile Thr Thr
```

```
1               5                   10                  15

Ile Asp Asp Ile Tyr Asp Phe Ser Val Ser Phe Arg Leu Cys Asn Asp
            20                  25                  30

Leu Gly Thr Ser Thr Ala Glu Leu Gln Arg Gly Glu Val Ala Asn Ser
        35                  40                  45

Ile Tyr Gln Thr Gly Asp Gly His
    50                  55


<210> SEQ ID NO 70
<211> LENGTH: 56
<212> TYPE: PRT
<213> ORGANISM: Petraea sp.

<400> SEQUENCE: 70

Arg Asp Arg Leu Met Glu Cys Phe Phe Phe Phe Ser Phe Ile Thr Val
1               5                   10                  15

Ile Asp Asp Ile Tyr Asp Phe Ser Val Ser Phe Arg Leu Thr Asn Asp
            20                  25                  30

Leu Gly Thr Ser Thr Ala Glu Leu Glu Arg Gly Glu Thr Ala Asn Ser
        35                  40                  45

Ile Tyr Gln His Gly Asp Gly His
    50                  55


<210> SEQ ID NO 71
<211> LENGTH: 56
<212> TYPE: PRT
<213> ORGANISM: Fragaria vesca

<400> SEQUENCE: 71

Lys Asp Arg Leu Met Glu Cys Phe Phe Trp Ser Ala Leu Ile Ser Thr
1               5                   10                  15

Val Asp Asp Val Tyr Asp Phe Ser Ala Ser Phe Arg Leu Thr Asn Asp
            20                  25                  30

Leu Ala Thr Ser Glu Ala Glu Leu Glu Arg Gly Glu Thr Ala Asn Ser
        35                  40                  45

Ile Tyr Gln Tyr Gly Asp Gly Ile
    50                  55


<210> SEQ ID NO 72
<211> LENGTH: 56
<212> TYPE: PRT
<213> ORGANISM: Morus notabilis

<400> SEQUENCE: 72

Arg Asp Arg Leu Met Glu Ser Phe Phe Trp Val Ala Phe Ile Thr Val
1               5                   10                  15

Ile Asp Asp Val Tyr Asp Phe Ser Ser Ser Phe Arg Leu Val Asn Asp
            20                  25                  30

Leu Ala Thr Ser Thr Ala Glu Leu Glu Arg Gly Glu Thr Asn Asn Ser
        35                  40                  45

Ile Tyr Gln His Gly Asp Gly His
    50                  55


<210> SEQ ID NO 73
<211> LENGTH: 56
<212> TYPE: PRT
<213> ORGANISM: Elaeocarpus sp.

<400> SEQUENCE: 73
```

```
Arg Asp Arg Leu Met Glu Ser Phe Phe Trp Phe Ala Leu Ile Thr Thr
1               5                   10                  15

Ile Asp Asp Val Tyr Asp Phe Ser Val Ser Phe Arg Leu Cys Asn Asp
            20                  25                  30

Leu Gly Thr Ser Ser Ala Glu Leu Glu Arg Gly Glu Leu Ala Asn Ser
        35                  40                  45

Ile Tyr Gln Tyr Gly Asp Ala His
    50                  55


<210> SEQ ID NO 74
<211> LENGTH: 56
<212> TYPE: PRT
<213> ORGANISM: Elaeocarpus photiniifolius

<400> SEQUENCE: 74

Arg Asp Arg Leu Met Glu Ser Phe Phe Trp Phe Ala Leu Ile Thr Thr
1               5                   10                  15

Ile Asp Asp Val Tyr Asp Phe Ser Val Ser Phe Arg Leu Cys Asn Asp
            20                  25                  30

Leu Gly Thr Ser Ser Ala Glu Leu Glu Arg Gly Glu Leu Ala Asn Ser
        35                  40                  45

Ile Tyr Gln Tyr Gly Asp Ala His
    50                  55


<210> SEQ ID NO 75
<211> LENGTH: 56
<212> TYPE: PRT
<213> ORGANISM: Populus trichocarpa

<400> SEQUENCE: 75

Arg Asp Arg Leu Met Glu Cys Phe Phe Trp Thr Ser Phe Ile Thr Thr
1               5                   10                  15

Ile Asp Asp Val Tyr Asp Phe Ser Val Ser Phe Arg Leu Ser Asn Asp
            20                  25                  30

Leu Ala Thr Ser Ser Ala Glu Ile Ala Arg Gly Glu Thr Ala Asn Ser
        35                  40                  45

Ile Tyr Gln His Gly Asp Gly His
    50                  55


<210> SEQ ID NO 76
<211> LENGTH: 56
<212> TYPE: PRT
<213> ORGANISM: Vitis vinifera

<400> SEQUENCE: 76

Arg Asp Arg Leu Met Glu Cys Phe Phe Trp Thr Ser Phe Ile Thr Thr
1               5                   10                  15

Ile Asp Asp Val Tyr Asp Phe Ser Val Ser Phe Arg Leu Cys Asn Asp
            20                  25                  30

Leu Ala Thr Ser Lys Ala Glu Leu Glu Arg Gly Glu Ser Ala Asn Ser
        35                  40                  45

Ile Tyr Gln Tyr Gly Asp Ser His
    50                  55


<210> SEQ ID NO 77
<211> LENGTH: 56
<212> TYPE: PRT
<213> ORGANISM: Populus alba

<400> SEQUENCE: 77
```

```
Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55


<210> SEQ ID NO 78
<211> LENGTH: 56
<212> TYPE: PRT
<213> ORGANISM: Populus canescens

<400> SEQUENCE: 78

Lys Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55


<210> SEQ ID NO 79
<211> LENGTH: 56
<212> TYPE: PRT
<213> ORGANISM: Salix sp.

<400> SEQUENCE: 79

Arg Asp Arg Leu Ile Glu Ser Phe Tyr Trp Phe Ser Phe Val Thr Ile
1               5                   10                  15

Ile Asp Asp Ile Tyr Asp Phe Ser Ser Ser Phe Arg Leu Cys Asn Asp
            20                  25                  30

Leu Ala Ser Ala Ser Ala Glu Ile Ala Arg Gly Glu Thr Ala Asn Ser
        35                  40                  45

Val Tyr His Asn Gly Asp Ala His
    50                  55


<210> SEQ ID NO 80
<211> LENGTH: 56
<212> TYPE: PRT
<213> ORGANISM: Malternifolia sp.

<400> SEQUENCE: 80

Arg Asp Arg Leu Met Glu Cys Phe Phe Trp Phe Ser Leu Ile Leu Val
1               5                   10                  15

Leu Asp Asp Val Tyr Asp Phe Ser Ser Ser Phe Arg Leu Thr Asn Asp
            20                  25                  30

Leu Ala Thr Ser Ser Ala Glu Leu Gly Arg Gly Glu Thr Thr Asn Ser
        35                  40                  45

Ile Tyr Gln Asp Gly Asp Ala Ile
    50                  55


<210> SEQ ID NO 81
<211> LENGTH: 56
<212> TYPE: PRT
<213> ORGANISM: Eglobulus sp.
```

<400> SEQUENCE: 81

```
Arg Asp Arg Leu Ile Glu Cys Phe Phe Trp Phe Ala Leu Ile Leu Val
1               5                   10                  15

Leu Asp Asp Val Tyr Asp Phe Ser Ser Ser Phe Arg Leu Thr Asn Asp
            20                  25                  30

Ile Ala Ser Ser Ser Ala Glu Leu Glu Arg Gly Glu Thr Thr Asn Ser
        35                  40                  45

Ile Tyr Gln Asp Gly Asp Ala Ile
    50                  55
```

<210> SEQ ID NO 82
<211> LENGTH: 56
<212> TYPE: PRT
<213> ORGANISM: Eucalyptus grandis

<400> SEQUENCE: 82

```
Arg Asp Arg Leu Thr Glu Cys Phe Phe Trp Thr Ser Leu Ile Thr Ile
1               5                   10                  15

Met Asp Asp Val Tyr Asp Phe Ser Ser Ser Phe Arg Leu Thr Asn Asp
            20                  25                  30

Leu Val Thr Leu Ser Ala Glu Leu Glu Arg Gly Glu Thr Thr Asn Ser
        35                  40                  45

Ile Tyr Gln Asp Gly Asp Ala His
    50                  55
```

<210> SEQ ID NO 83
<211> LENGTH: 56
<212> TYPE: PRT
<213> ORGANISM: Wisteria sp.

<400> SEQUENCE: 83

```
Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln His Gly Asp Gly Leu
    50                  55
```

<210> SEQ ID NO 84
<211> LENGTH: 56
<212> TYPE: PRT
<213> ORGANISM: Robinia pseudoacacia

<400> SEQUENCE: 84

```
Arg Asp Arg Leu Val Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 85
<211> LENGTH: 56
<212> TYPE: PRT
<213> ORGANISM: Arachis hypogaea

<400> SEQUENCE: 85

```
Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 86
<211> LENGTH: 56
<212> TYPE: PRT
<213> ORGANISM: Glycine max

<400> SEQUENCE: 86

```
Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Thr Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 87
<211> LENGTH: 56
<212> TYPE: PRT
<213> ORGANISM: Pueraria montana var. lobata

<400> SEQUENCE: 87

```
Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 88
<211> LENGTH: 56
<212> TYPE: PRT
<213> ORGANISM: Mucuna pruriens

<400> SEQUENCE: 88

```
Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Arg Gly Glu Thr Thr Asn Ser
        35                  40                  45

Ile Tyr Gln Tyr Gly Asp Gly Leu
    50                  55
```

<210> SEQ ID NO 89
<211> LENGTH: 56
<212> TYPE: PRT

<213> ORGANISM: Glycine max

<400> SEQUENCE: 89

```
Arg Asp Arg Leu Met Glu Val Tyr Phe Trp Phe Ala Leu Ile Gly Ile
1               5                   10                  15

Ile Asp Asp Val Tyr Asp Phe Ser Ser Ser Phe Arg Leu Cys Asn Asp
            20                  25                  30

Leu Ala Thr Ser Ala Ala Glu Leu Glu Thr Gly Glu Thr Ala Asn Ser
        35                  40                  45

Ile Tyr Gln Tyr Glu Asp Gly Leu
    50                  55
```

<210> SEQ ID NO 90
<211> LENGTH: 56
<212> TYPE: PRT
<213> ORGANISM: Cajanus cajan

<400> SEQUENCE: 90

```
Arg Asp Arg Leu Met Glu Val Tyr Phe Trp Phe Gly Leu Val Thr Ile
1               5                   10                  15

Ile Asp Asp Val Tyr Asp Phe Ser Ser Ser Phe Arg Leu Tyr Asn Asp
            20                  25                  30

Leu Ala Thr Ser Ala Ala Glu Leu Glu Arg Asp Glu Thr Thr Asn Ser
        35                  40                  45

Met Tyr Gln His Gly Asp Gly Leu
    50                  55
```

<210> SEQ ID NO 91
<211> LENGTH: 56
<212> TYPE: PRT
<213> ORGANISM: Mangifera indica

<400> SEQUENCE: 91

```
Arg Asp Arg Leu Met Glu Cys Tyr Phe Trp Phe Ala Phe Val Thr Thr
1               5                   10                  15

Ile Asp Asp Ile Tyr Asp Phe Ser Ser Ser Phe Arg Leu Cys Asn Asp
            20                  25                  30

Leu Ser Thr Ser Lys Asp Glu Leu Glu Arg Gly Glu Thr Ala Ser Ser
        35                  40                  45

Ile Tyr Gln His Gly Asp Gly His
    50                  55
```

<210> SEQ ID NO 92
<211> LENGTH: 56
<212> TYPE: PRT
<213> ORGANISM: Ipomoea batatas

<400> SEQUENCE: 92

```
Arg Asp Arg Leu Met Glu Ser Phe Phe Trp Phe Lys Leu Val Thr Val
1               5                   10                  15

Leu Asp Asp Val Tyr Asp Phe Ser Val Ser Phe Arg Leu Ala Asn Asp
            20                  25                  30

Leu Ser Ser Ser Lys Ala Glu Ile Glu Arg Gly Glu Thr Ala Asn Ser
        35                  40                  45

Ile Tyr Gln Tyr Gly Asp Ala His
    50                  55
```

<210> SEQ ID NO 93
<211> LENGTH: 56

```
<212> TYPE: PRT
<213> ORGANISM: Sesamum indicum

<400> SEQUENCE: 93

Arg Asp Arg Leu Met Glu Ser Phe Phe Trp Val Asn Leu Ile Thr Val
1               5                   10                  15

Leu Asp Asp Ile Tyr Asp Phe Ser Ser Ser Phe Arg Leu Ala Asn Asp
            20                  25                  30

Leu Ser Ser Ser Lys Asp Asp Val Gly Arg Gly Glu Thr Ala Lys Ala
        35                  40                  45

Val Tyr Gln His Gly Asp Ala His
    50                  55


<210> SEQ ID NO 94
<211> LENGTH: 56
<212> TYPE: PRT
<213> ORGANISM: Humulus lupulus

<400> SEQUENCE: 94

Arg Asp Arg Leu Met Glu Ala Phe Leu Trp Phe Val Leu Ile Thr Ile
1               5                   10                  15

Ile Asp Asp Ile Tyr Asp Tyr Ser Ile Gly Val Arg Leu Ala Asp Asp
            20                  25                  30

Phe Gly Thr Phe Ser Asp Glu Leu Asn Arg Gly Asp Val Pro Lys Ser
        35                  40                  45

Ile Tyr Gln Tyr Gly Asp Gly His
    50                  55


<210> SEQ ID NO 95
<211> LENGTH: 56
<212> TYPE: PRT
<213> ORGANISM: Matricaria recutita

<400> SEQUENCE: 95

Arg Asp Arg Leu Met Glu Cys Phe Phe Trp Ala Thr Leu Ile Thr Thr
1               5                   10                  15

Ile Asp Asp Ile Tyr Asp Phe Ser Val Ser Phe Arg Leu Tyr Asn Asp
            20                  25                  30

Leu Ala Ala Leu Ala Asp Glu Ile Asp Lys Asp Lys Ser Pro Asn Ala
        35                  40                  45

Ile Tyr Gln Tyr Gly Asp Gly Ile
    50                  55


<210> SEQ ID NO 96
<211> LENGTH: 56
<212> TYPE: PRT
<213> ORGANISM: Dahlia pinnata

<400> SEQUENCE: 96

Arg Asp Arg Leu Leu Glu Cys Phe Phe Trp Ser Thr Phe Ile Thr Ile
1               5                   10                  15

Leu Asp Asp Ile Tyr Asp Phe Ser Val Ser Phe Arg Leu Tyr Asn Asp
            20                  25                  30

Leu Ala Thr Ser Ser Ser Glu Ile Gln Arg Gly Lys Asn Val Asn Ala
        35                  40                  45

Val Tyr Gln Tyr Gly Asp Gly His
    50                  55
```